United States Patent
Noguchi et al.

(10) Patent No.: US 7,037,735 B2
(45) Date of Patent: May 2, 2006

(54) APPARATUS AND METHOD FOR TESTING DEFECTS

(75) Inventors: Minori Noguchi, Yokohama (JP); Yoshimasa Ohshima, Yokohama (JP); Hidetoshi Nishiyama, Fujisawa (JP); Shunichi Matsumoto, Yokohama (JP); Yukio Kembo, Shakujii-machi (JP); Ryouji Matsunaga, Chigasaki (JP); Keiji Sakai, Tokyo (JP); Takanori Ninomiya, Hiratsuka (JP); Tetsuya Watanabe, Honjo (JP); Hisato Nakamura, Kamisato-machi (JP); Takahiro Jingu, Takasaki (JP); Yoshio Morishige, Honjo (JP); Shuichi Chikamatsu, Kounosu (JP)

(73) Assignees: Hitachi, Ltd., Tokyo (JP); Hitachi High-Technologies Corporation, Tokyo (JP)

( * ) Notice: Subject to any disclaimer, the term of this patent is extended or adjusted under 35 U.S.C. 154(b) by 153 days.

(21) Appl. No.: 10/170,378

(22) Filed: Jun. 14, 2002

(65) Prior Publication Data

US 2002/0168787 A1 Nov. 14, 2002

Related U.S. Application Data

(63) Continuation of application No. 09/362,135, filed on Jul. 28, 1999, now Pat. No. 6,411,377, which is a continuation-in-part of application No. 08/535,577, filed on Sep. 28, 1995, which is a continuation of application No. 08/046,720, filed on Apr. 16, 1993, now Pat. No. 5,463,459, which is a continuation-in-part of application No. 07/778,363, filed on Oct. 17, 1991, now Pat. No. 5,274,434, which is a continuation-in-part of application No. 07/679,317, filed on Apr. 2, 1991, now Pat. No. 5,233,191.

(30) Foreign Application Priority Data

Jul. 28, 1998 (JP) ............................... P10-213056

(51) Int. Cl.
*H01L 21/66* (2006.01)
*G01R 31/26* (2006.01)

(52) U.S. Cl. .................. 438/18; 438/16; 250/492.1; 250/492.2; 356/237.1

(58) Field of Classification Search .. 356/237.1–237.5; 438/16; 250/492.1, 492.2
See application file for complete search history.

(56) References Cited

U.S. PATENT DOCUMENTS 3,790,287 A * 2/1974 Cuthbert et al. ............ 356/446

(Continued)

FOREIGN PATENT DOCUMENTS

EP 000294643 A2 12/1988

(Continued)

*Primary Examiner*—Thanh Nguyen
(74) *Attorney, Agent, or Firm*—Antonelli, Terry, Stout and Kraus, LLP.

(57) ABSTRACT

A defect inspection method includes radiating an illumination slit-shaped beam having lights substantially parallel to a longitudinal direction to a substrate having circuit patterns in a direction inclined at a predetermined gradient relative to the direction of a line normal to the substrate and inclined at a predetermined gradient on a surface with respect to a group of main straight lines of the circuit patterns with its longitudinal direction oriented almost perpendicularly to a direction of a movement of the substrate. Scattered light reflected by a defect such as a foreign particle existing on the illuminated substrate is received and converted into a detection signal by using an image sensor, and defect judging is effected of an extracted a signal indicating a defect such as a foreign particle on the basis of the detection signal output.

18 Claims, 36 Drawing Sheets

U.S. PATENT DOCUMENTS

| | | | |
|---|---|---|---|
| 4,153,336 A * | 5/1979 | Minami et al. ............... 349/17 |
| 4,330,205 A * | 5/1982 | Murakami et al. ....... 356/237.1 |
| 4,468,120 A | 8/1984 | Tanimoto et al. |
| 4,877,326 A | 10/1989 | Chadwick et al. |
| 4,898,471 A | 2/1990 | Vaught et al. |
| 4,929,081 A | 5/1990 | Yamamoto et al. |
| 4,936,664 A | 6/1990 | Haraguchi et al. |
| 5,162,867 A | 11/1992 | Kohno |
| 5,177,559 A | 1/1993 | Batchelder et al. |
| 5,233,191 A | 8/1993 | Noguchi et al. |
| 5,410,400 A | 4/1995 | Shishido et al. |
| 5,461,474 A | 10/1995 | Yoshii et al. |
| 5,463,459 A | 10/1995 | Morioka et al. |
| 5,486,919 A | 1/1996 | Tsuji et al. |
| 5,565,979 A | 10/1996 | Gross |
| 5,604,585 A | 2/1997 | Johnson et al. |
| 5,726,740 A | 3/1998 | Shiozawa et al. |
| 5,774,575 A | 6/1998 | Tanaka et al. |
| 5,777,729 A | 7/1998 | Aiyer et al. |
| 5,801,824 A | 9/1998 | Henley |
| 5,805,278 A | 9/1998 | Danko |
| 5,912,735 A | 6/1999 | Xu |
| 5,923,461 A | 7/1999 | Allen et al. |
| 5,963,314 A | 10/1999 | Worster et al. |
| 6,020,957 A * | 2/2000 | Rosengaus et al. ...... 356/237.4 |
| 6,052,478 A | 4/2000 | Wihl et al. |
| 6,608,676 B1 | 8/2003 | Zhao et al. |

FOREIGN PATENT DOCUMENTS

| | | |
|---|---|---|
| JP | 59-934 | 1/1986 |
| JP | 62-89336 | 4/1987 |
| JP | 63-029238 | 2/1988 |
| JP | 63-135848 | 6/1988 |
| JP | 64-53132 | 3/1989 |
| JP | 64-88237 | 4/1989 |
| JP | 1-117024 | 5/1989 |
| JP | 1-250847 | 10/1989 |
| JP | 2-223845 | 9/1990 |
| JP | 5-129397 | 5/1993 |
| JP | 5-218163 | 8/1993 |
| JP | 5-036016 | 2/1994 |
| JP | 6-160062 | 6/1994 |
| JP | 6-258047 | 9/1994 |
| JP | 6-258239 | 9/1994 |
| JP | 6-324003 | 11/1994 |
| JP | 7-190739 | 7/1995 |
| JP | 7-294449 | 11/1995 |
| JP | 7-318504 | 12/1995 |
| JP | 8-210989 | 8/1996 |
| JP | 8-271437 | 10/1996 |
| JP | 8-293533 | 11/1996 |
| JP | 9-210919 | 8/1997 |
| JP | 9-243546 | 9/1997 |

* cited by examiner

SURFACE-RADIATION
TDI IMAGE SENSOR

BACK-PLANE-RADIATION
TDI IMAGE SENSOR (TDI : Time Delay & Integration)

STANDARD PARTICLE DIAMETER [MICRONS]
STANDARD PARTICLE DATA/MIRROR SURFACE WAFER

APPARATUS AND METHOD FOR TESTING DEFECTS

CROSS-REFERENCE TO RELATED APPLICATIONS

This is a continuation of U.S. application Ser. No. 09/362,135, filed Jul. 28, 1999, now U.S. Pat. No. 6,411,377, which is a continuation-in-part of U.S. application Ser. No. 08/535,577, filed Sep. 28, 1995, which is a continuation application of U.S. application Ser. No. 08/046,720, filed Apr. 16, 1993, now U.S. Pat. No. 5,463,459, which is a continuation-in-part of U.S. application Ser. No. 07/679,317, filed Apr. 2, 1991, now U.S. Pat. No. 5,233,191 and U.S. application Ser. No. 07/778,363, filed Oct. 17, 1991, now U.S. Pat. No. 5,274,434.

BACKGROUND OF THE INVENTION

The present invention relates to a defect testing apparatus and a defect testing method for inspecting a state of generation of defects such as foreign particles in a fabrication process such as a semiconductor fabrication process, a liquid-crystal-display fabrication process and a print-board fabrication process wherein a defect such as a foreign particle generated in a process to create a pattern on a substrate to produce an object is detected and analyzed in order to determine a countermeasure.

In the conventional semiconductor fabrication method, a foreign particle existing on a semiconductor substrate also known as a wafer causes a defect such as poor insulation of a wire or a short circuit. Furthermore, in the case of a miniaturized semiconductor device, an infinitesimal foreign particle existing in a semiconductor substrate results in poor insulation of a capacitor or destruction of typically a gate oxide film. These foreign particles are introduced to get mixed with a semiconductor material in a variety of states due to a variety of causes For example, a foreign particle is generated by a movable part of a transportation apparatus or a human body A foreign particle can also be generated as a result of a chemical reaction in processing equipment using a process gas or mixed with chemicals or a raw material.

Likewise, if a foreign particle is introduced to get mixed with a pattern, causing some defects in a process to fabricate a liquid-crystal display device, the resulting display device is not usable. The process to fabricate a print board is in the same situation, That is to say, a mixed foreign particle causes a poor connection and a short circuit in a pattern.

One of publications for detecting a foreign particle on a semiconductor substrate of this type is disclosed in Japanese Patent Laid-open No. Sho 62-89336 and referred to hereafter as publication 1. According to this prior art, a laser beam is radiated to a semiconductor substrate. If a foreign particle is stuck to the semiconductor substrate, the foreign particle will generate scattered beams which can then be detected and compared with a result of inspection for a semiconductor substrate of the same type inspected immediately before. In this way, a difference in inspection result can be detected and used to eliminate a pattern defect. As a result, a foreign particle and a defect can be detected with a high degree of sensitivity and a high degree of reliability. Another publication referred to hereafter as publication 2 is disclosed in Japanese Patent Laid-open No. Sho 63-135848. According to this publication, a laser beam is radiated to a semiconductor substrate. If a foreign particle is stuck to the semiconductor substrate, the foreign particle will generate scattered beams which can then be detected. A detected beam generated by a foreign particle is analyzed by using an analysis technique such as laser photo luminescence or a secondary X-ray analysis (XMR).

In addition, as a technology for detecting a foreign particle, there is also known a technique whereby a coherent beam is radiated to a wafer, and the beam reflected by repetitive patterns on the wafer is removed by~ a spatial filter to emphasize light components generated by a foreign particle or a defect which does not exhibit repetitiveness. In this way,' a foreign particle or a defect can be detected.

A technology disclosed in Japanese Patent Laid-open No. Hei 1-117024 is referred to hereafter as publication 3. According to this publication, in a foreign particle inspecting apparatus, a beam is radiated to a circuit pattern on a wafer in a direction forming an angle of 45 degrees with respect to a group of main straight lines of the circuit pattern and a 0th-order diffracted beam from the group of main straight lines is introduced into the aperture of an objective lens. The disclosure also includes a description which states that, according to publication 3, a beam from any group of straight lines other than the group of main straight lines is shielded by a spatial filter.

In addition, other publications related to apparatuses and methods for detecting defects such as foreign particles are disclosed in Japanese Patent Laid-open No. Hei 1-250847, Japanese Patent Laid-open No. Hei 6-258239, Japanese Patent Laid-open No. Hei 6-324003, Japanese Patent Laid-open No. Hei 8-210989 and Japanese Patent Laid-open No. Hei 8-271437 and referred to as publications 4, 5, 6 ,7 and 8 respectively.

With publications 1 to 8 mentioned above, however, it is impossible to detect a defect such as an infinitesimal foreign particle on a substrate, on which repetitive patterns coexist with non-repetitive patterns, at a high speed, with ease and with a high degree of sensitivity.

To put it in detail, publications 1 to 8 have a problem of a substantially reduced sensitivity (increased minimum dimensions of a detected foreign particle) in the case of a part of the substrate other than the repetitive portion such as memory cells.

In addition, publications 1 to 8 also have a problem of a substantially reduced sensitivity in the case of an oxide film which passes a radiation beam.

Moreover, publications 1 to 8 also have a problem of inability to detect a defect such as an infinitesimal foreign particle.

Furthermore, in the case of publications 1 to 8, a mass-production build-up line or a pilot line and a mass-production line of a semiconductor production process are not distinguished from each other. That is to say, inspection equipment used in the mass-production build-up work is also used in a mass-production line without change in spite of the fact that it is necessary to early detect generation of a foreign particle on the mass-production line and determine a countermeasure for the detected foreign particle.

At any rate, the conventional defect inspecting apparatus is large in size and has such a configuration that the apparatus must be installed independently. For this reason, in order to inspect a foreign particle and a defect, it is necessary to transport a semiconductor substrate, a liquid-crystal-display substrate or a print substrate which has been processed along the mass-production line to a place at which the defect inspecting apparatus is installed. That is to say, it takes time to transport the substrate and to inspect the substrate for a foreign particle and a defect. As a result, complete inspection is difficult. In addition, it is hard to carry out such sampling inspection at a sufficiently high frequency.

Further, a defect inspecting apparatus with such a configuration requires an operator.

SUMMARY OF THE INVENTION

It is thus an object of the present invention addressing the problems described above to provide a defect inspecting apparatus and a defect inspection method capable of inspecting a defect such as an infinitesimal foreign particle on an inspected substrate containing repetitive patterns, non-repetitive patterns and non-patterns which coexist with each other at a high speed and with a high degree of precision.

It is another object of the present invention to provide a defect inspecting apparatus and a defect inspection method which allow a high-efficiency substrate fabrication line to be constructed by implementation of complete inspection and sampling inspection at a sufficiently high frequency.

It is still another object of the present invention to provide a defect inspecting apparatus and a defect inspection method which are capable of inspecting also a defect such as an extremely infinitesimal foreign particle having a size of the order of 0.1 μm or smaller at a high speed and with a high degree of sensitivity by effectively utilizing the light quantity of a Gaussian beam generated by an ordinary inexpensive light source such as a laser-beam source.

It is a further object of the present invention to provide a defect inspecting apparatus and a defect inspection method which are capable of inspecting also a defect such as an extremely infinitesimal foreign particle having a size of the order of 0.1 μm or smaller at a high speed and with a high degree of sensitivity by effectively utilizing the light quantity of a Gaussian beam generated by typically a laser-beam source and by resolving a problem of a lack of illumination at regions surrounding an area on a substrate being inspected due to a decrease in MTF at locations separated away from an optical axis in a detection optical system.

It is a still further object of the present invention to provide a defect inspecting apparatus capable of inspecting a defect such as a real foreign particle by setting the level of a threshold value at a proper degree of sensitivity without substantially increasing the amount of generated false information wherein the threshold value is used as a criterion as to whether or not a defect exists in a variety of circuit-pattern areas in the device structure laid out on a substrate being inspected.

It is a still further object of the present invention to provide a defect inspecting apparatus capable of inspecting a defect such as a foreign particle with a specified size to be detected by setting the level of a threshold value used as a criterion as to whether or not a defect exists for the size of the defect to be detected in a variety of circuit-pattern areas in the device structure laid out on a substrate being inspected.

It is a still further object of the present invention to provide a defect inspecting apparatus capable of inspecting a defect such as a foreign particle by allowing the size of the defect existing in a variety of circuit-pattern areas in the device structure laid out on a substrate being inspected to be inferred.

It is a still further object of the present invention to provide a semiconductor-substrate fabricating method for fabricating a semiconductor substrate at a high efficiency and, hence, at a high yield.

In order to achieve the objects described above, the present invention provides a defect inspecting apparatus and a defect inspection method adopted by the defect inspecting apparatus comprising: a stage for mounting and moving an inspected substrate with a circuit pattern created thereon; an illumination optical system for illuminating the substrate by forming a beam radiated by a light source into a slit-shaped beam and directing the beam toward the substrate being inspected at a predetermined gradient of $(\pi/2-\alpha 1)$ with respect to the direction of a line normal to the substrate and a predetermined gradient of $\Phi I$ with respect to a group of main straight lines of the circuit pattern on the surface of the substrate wherein the longitudinal direction is almost perpendicular to a direction of the y axis of the movement of the stage; a detection optical system including an image sensor for receiving scattered beams reflected by a defect such as a foreign particle existing on the inspected substrate illuminated by the slit-shaped beam radiated by the illumination optical system and for converting the scattered beams into a detection signal representing a result of detection of the defect; and an image-signal processing unit for extracting a signal showing the defect such as a foreign particle on the basis of the detection signal output by the image sensor employed in the detection optical system.

In addition, in order to achieve the objects described above, the present invention also provides a defect inspecting apparatus and a defect inspection method adopted by the defect inspecting apparatus comprising: a stage for mounting and moving an inspected substrate with circuit patterns created thereon; an illumination optical system for illuminating the substrate by forming a beam radiated by a light source into a slit-shaped beam and directing the beam toward the substrate being inspected at a predetermined gradient of $(\pi/2-\alpha 1)$ with respect to the direction of a line normal to the substrate and a predetermined gradient of $\Phi 1$ with respect to a group of main straight lines of the circuit pattern on the surface of the substrate wherein the longitudinal direction is almost perpendicular to a direction of the y axis of the movement of the stage; a detection optical system including an image sensor for receiving scattered beams reflected by a defect such as a foreign particle existing on the inspected substrate illuminated by the slit-shaped beam radiated by the illumination optical system and for converting the scattered beams into a detection signal representing a result of detection of the defect; and an image processing unit having: a criterion setting means which calculates a variation of the detection signal output by the image sensor of the detection optical system to represent a variation of a scattered beam reflected by areas on the surface of the substrate in which the naturally identical circuit patterns are created or regions in close proximity to the areas and which sets a criterion (threshold value) based on the calculated variation; and a signal extracting means which extracts a signal showing the defect such as a foreign particle from the detection signal output by the image sensor employed in the detection optical system on the basis of the criterion set by the criterion setting means.

Furthermore, the present invention also provides a defect inspecting apparatus and a defect inspection method adopted by the defect inspecting apparatus comprising: a stage unit for mounting and moving an inspected substrate with a circuit pattern created thereon; an illumination optical system for illuminating the substrate by forming a beam radiated by a light source into a slit-shaped beam and directing the beam toward the substrate being inspected at a predetermined gradient with respect to the direction of a line normal to the substrate and a predetermined gradient with respect to a group of main straight lines of the circuit pattern on the surface of the substrate wherein the longitudinal direction is almost perpendicular to a y direction of the movement of the stage; a detection optical system including an image sensor for receiving scattered beams reflected by a defect such as a foreign particle existing on the inspected substrate illuminated by the slit-shaped beam radiated by the illumination optical system and for converting the scattered beams into a detection signal representing a result of detection of the defect; and an image-signal processing unit for extracting a signal showing the defect such as a foreign particle from the detection signal output by the image sensor employed in the detection optical system on the basis of a criterion (threshold value) set for each of a variety of areas composing the circuit pattern.

Moreover, in the defect inspecting apparatuses and the defect inspection methods provided by the present invention, the predetermined gradient of $\Phi 1$ of the slit-shaped beams with respect to a group of main straight lines of the circuit pattern on the surface of the substrate is about 45 degrees.

Further, in the defect inspecting apparatuses and the defect inspection methods provided by the present invention, the optical axis of the detection optical system is substantially perpendicular to the substrate being inspected.

In addition, in the defect inspecting apparatuses and the defect inspection methods provided by the present invention, the optical axis of the detection optical system is inclined with respect to the line normal to the substrate being inspected.

Furthermore, in the defect inspecting apparatus provided by the present invention, the light source employed in the illumination optical system is a laser-beam source.

Moreover, in the defect inspecting apparatus provided by the present invention, the illumination optical system has an optical element of a shape resembling a cone for generating a converged light.

Further, in the defect inspecting apparatus provided by the present invention, the illumination optical system is provided with an optical system for radiating a white light in a direction inclined with respect to a normal line to a substrate being inspected.

In addition, in the defect inspecting apparatus provided by the present invention, the illumination optical system is provided with a space filter.

Furthermore, in the defect inspecting apparatus provided by the present invention, the image sensor employed in the detection optical system is a TDI (Time Delay Integration) image sensor.

Moreover, the present invention provides a defect inspecting apparatus comprising: an illumination optical system having an optical element of a shape resembling a cone for radiating an illumination light beam in a direction at a predetermined gradient with respect to a line normal to the surface of an object of inspection and for converging the illumination light beam in at least one direction on the surface of the object of inspection; a detection optical system including an image sensor which receives a light reflected by the object of inspection and converts the received light into a detection signal; and an image-signal processing unit for processing the detection signal output by the detection optical system.

Further, the detection optical system employed in the defect inspecting apparatus provided by the present invention has: a beam splitting optical system for splitting a light beam reflected by the object of inspection into reflected beams with one of the reflected beams having an intensity of about $\frac{1}{100}$ of that of another; and a plurality of image sensors for receiving each of the reflected beams split by the beam splitting optical system.

In addition, the present invention provides a defect inspecting apparatus comprising: an illumination optical system for radiating an illumination light to a surface of an object of inspection on which a plurality of circuit patterns with substantially identical shapes are laid out; a detection optical system including an image sensor for receiving a light reflected by the object of inspection and for converting the received light into a detected image signal; and an image-signal processing unit for processing the detected image signal and being provided with: a criterion setting means which calculates a variation of an image signal among pixels which correspond to the circuit patterns with identical shapes or pixels in close proximity thereto on the basis of the image signal detected by the detection optical system and which sets a threshold value to serve as a criterion as to whether or not a defect such as a foreign particle exists on the basis of the calculated variation of the image signal; and a judgment means which forms a judgment as to whether or not a defect exists from the image signal detected by the detection optical system on the basis of the criterion set by the criterion setting means.

Furthermore, the present invention provides a defect inspecting apparatus comprising: an illumination optical system for radiating an illumination light to a surface of an object of inspection on which a plurality of patterns with substantially identical shapes are laid out; a detection optical system including an image sensor for receiving a light reflected by the object of inspection and for converting the received light into a detected image signal; and an image-signal processing unit for processing the detected image signal and being provided with: a difference computing means which computes differences in image signal among pixels corresponding to the patterns having identical shapes on the basis of an image signal detected by the detection optical system; a criterion setting means which calculates a variation of the differences computed by the difference computing means at a plurality of for pixels adjacent to pixels used for forming a judgment as to whether or not a defect such as a foreign particle exists and which sets a criterion of the level of a pixel signal used for determining whether or not the defect such as the foreign particle exists on the basis of the calculated variation; and a judgment means which forms a judgment as to whether or not the defect exists from the image signal detected by the detection optical system on the basis of the criterion set by the criterion setting means.

Moreover, in the defect inspecting apparatus provided by the present invention, the image-signal processing unit has an output means which outputs pieces of a result of defect inspection produced by the judgment means and data representing the criterion set by the criterion setting means.

Further, the present invention provides a defect inspecting apparatus comprising: an illumination optical system for radiating an illumination light to a surface of an object of inspection on which a plurality of patterns with substantially identical shapes are laid out; a detection optical system including an image sensor for receiving a light reflected by the object of inspection and for converting the received light into a detected image signal; and an image-signal processing unit having: a judgment means which forms a judgment as to whether or not a defect exists by comparison of the image signal output by the detection optical system with a criterion; and a display means which displays map information or images on the patterns having identical shapes to be used as the criterion by the judgment means, or which displays relations between criteria (or sensitivities) and indicators of inspection area for them, or which displays sensitivity information on circuit patterns having identical shapes corresponding to criteria.

In addition, the image-signal processing unit employed in the defect inspecting apparatus provided by the present invention has an area priority mode, a standard mode and a sensitivity priority mode as condition specifying modes.

Furthermore, the present invention provides a defect inspecting apparatus comprising: an illumination optical system for radiating an illumination light to a surface of an object of inspection on which a plurality of patterns with substantially identical shapes are laid out; a detection optical system including an image sensor for receiving a light reflected by the object of inspection and for converting the received light into a detected image signal; and an image-signal processing unit for processing the detected image signal and being provided with: a criterion setting means which sets a criterion by varying the criterion in accordance with a state of an underlying layer in the patterns with identical shapes; and a judgment means which forms a judgment as to whether or not a defect exists by comparison of the image signal output by the detection optical system with the criterion set by the criterion setting means.

Moreover, the present invention provides a defect inspecting apparatus comprising: an illumination optical system for radiating an illumination light to a surface of an object of inspection on which a plurality of patterns with substantially identical shapes are laid out; a detection optical system including an image sensor for receiving a light reflected by the object of inspection and for converting the received light into a detected image signal; and an image-signal processing unit for processing the detected image signal output by the detection optical system and being provided with: a size specifying means which specifies a size of a defect; a criterion setting means which sets a criterion by varying the criterion in accordance with the defect size specified by the size specifying means; and a judgment means which forms a judgment as to whether or not a defect exists by comparison of the image signal output by the detection optical system with the criterion set by the criterion setting means.

Further, the present invention provides a defect inspecting apparatus comprising: an illumination optical system for radiating an illumination light to a surface of an object of inspection on which a plurality of patterns with substantially identical shapes are laid out; a detection optical system including an image sensor for receiving a light reflected by the object of inspection and for converting the received light into a detected image signal; and an image-signal processing unit for processing the detected image signal output by the detection optical system and being provided with: a size specifying means which specifies a size of a defect; and a control means which controls the power of the illumination light radiated by the illumination optical system in accordance with the defect size specified by the size specifying means.

In addition, the present invention provides a defect inspecting apparatus comprising: an image-pickup optical system having: an illumination optical subsystem for radiating an illumination light to a surface of an object of inspection mounted on a stage with the object having a plurality of patterns having substantially identical shapes laid out on the object of inspection; and a detection optical subsystem including an image sensor for receiving a light reflected by the object of inspection and for converting the received light into a detected image signal; an image-signal processing unit including a judgment means which forms a judgment as to whether or not a defect exists by comparison of the image signal output by the detection optical subsystem employed in the image-pickup optical system with a criterion; and an optical observation microscope provided along with the image-pickup optical system and used for observation of an optical object on the object of inspection.

Furthermore, in the defect inspecting apparatus provided by the present invention, the optical observation microscope is implemented by an ultraviolet-ray optical observation microscope.

Moreover, the present invention provides a defect inspecting apparatus comprising: an illumination optical system for radiating an illumination light to a surface of an object of inspection; a detection optical system including a photo-electrical conversion means which receives a light reflected by the object of inspection and converts the received light into a detected signal; and an image-signal processing unit including a means which detects a defect by processing the signal detected by the detection optical system and outputs a result of the defect detection including pattern information indicating existence of a defect.

Further, in the defect inspecting apparatus provided by the present invention, the pattern information output by the means employed in the image-signal processing unit is information obtained from design data of patterns.

In addition, the present invention provides a defect inspecting apparatus comprising: an illumination optical system for radiating an illumination light to a surface of an object of inspection; a detection optical system including a photo-electrical conversion means which receives a light reflected by the object of inspection and converts the received light into a detected signal; and an image-signal processing unit including a means which extracts a signal level of a defect by processing the signal detected by the detection optical system, and which corrects the extracted defect signal level so as to make the signal level indicate the size of the defect, and which outputs the corrected defect signal level.

Furthermore, the means employed in the image-signal processing unit of the defect inspecting apparatus provided by the present invention corrects the signal level of the defect on the basis of the intensity of the illumination light or data representing the reflectance of the surface of a pattern.

Moreover, the illumination optical system employed in the defect inspecting apparatus provided by the present invention is configured so that a light source thereof radiates a slit-shaped beam to a detection area on a substrate serving as an object of inspection wherein the slit-shaped beam is formed into a slit-shaped Gaussian beam exhibiting a Gaussian illumination distribution having a standard deviation substantially equal to a distance from an optical axis of the detection area to a periphery.

Further, the illumination optical system employed in the defect inspecting apparatus provided by the present invention is configured to have a light source thereof radiate a slit-shaped beam to a detection area on a substrate serving as an object of inspection wherein the slit-shaped beam is formed into a slit-shaped Gaussian beam by properly adjusting a diameter or a major-axis length of the beam to a distance between peripheries having the center thereof coinciding with an optical axis of the detection area so that a ratio of an illumination at the peripheries of the detection area to an illumination at the center of the detection area has a value in the range 0.46 to 0.73.

In addition, in the defect inspecting apparatus provided by the present invention, the slit-shaped Gaussian beam radiated by the illumination optical system is a DUV (Deep Ultra-Violet) beam.

In the configurations described above, it is possible to detect a defect such as an infinitesimal foreign particle on an inspected substrate, on which repetitive patterns, non-repetitive patterns and non-patterns coexist with each other, at a high speed and with a high degree of precision.

In addition, in the configurations described above, by effectively utilizing the light quantity of a Gaussian beam radiated by an ordinary inexpensive light source such as a laser-beam source, it is possible to detect also a defect such as an infinitesimal foreign particle with a size of the order of 0.1 μm or smaller at a high speed and with a high degree of sensitivity.

Furthermore, in the configurations described above, by effectively utilizing the light quantity of a Gaussian beam radiated by typically a laser-beam source, it is possible to detect also a defect such as an infinitesimal foreign particle with a size of the order of 0.1 μm or smaller at a high speed and with a high degree of sensitivity by resolving a problem of a lack of illumination at regions surrounding an area on a substrate being inspected due to a decrease in MTF at locations separated away from an optical axis in a detection optical system.

Moreover, in the configurations described above, it is possible to detect a defect such as a real foreign particle by setting the level of a threshold value at a proper degree of sensitivity without substantially increasing the amount of generated false information wherein the threshold value is used as a criterion as to whether or not a defect exists in a variety of circuit-pattern areas in the device structure laid out on a substrate being inspected.

Further, in the configurations described above, it is possible to detect a defect such as a foreign particle with a size to be detected by setting the level of a threshold value used as a criterion as to whether or not a defect exists for the size of the defect to be detected in a variety of circuit-pattern areas in the device structure laid out on a substrate being inspected.

In addition, in the configurations described above, it is possible to detect a defect such as a foreign particle by allowing the size of the defect existing in a variety of circuit-pattern areas in the device structure laid out on a substrate being inspected to be inferred.

Furthermore, in the configurations described above, it is possible to construct a high-efficiency substrate fabrication line by implementation of complete inspection and sampling inspection at a sufficiently high frequency.

BRIEF DESCRIPTION OF THE DRAWINGS

FIG. 11(a) is a diagram showing a birds eye view of radiation and detection directions according to the present invention whereas

FIG. 21 is a diagram showing a relation between: a state of generation of a 0th-order diffraction-light pattern by radiation of a slit-shaped beam in a direction parallel to a group of main straight lines of a circuit pattern according to the present invention; and an aperture of an objective lens of a detection optical system with the 0th-order diffraction-light pattern not getting in;

DETAILED DESCRIPTION OF THE PREFERRED EMBODIMENTS

Some preferred embodiments of the present invention are explained by referring to diagrams as follows.

Figure 1:
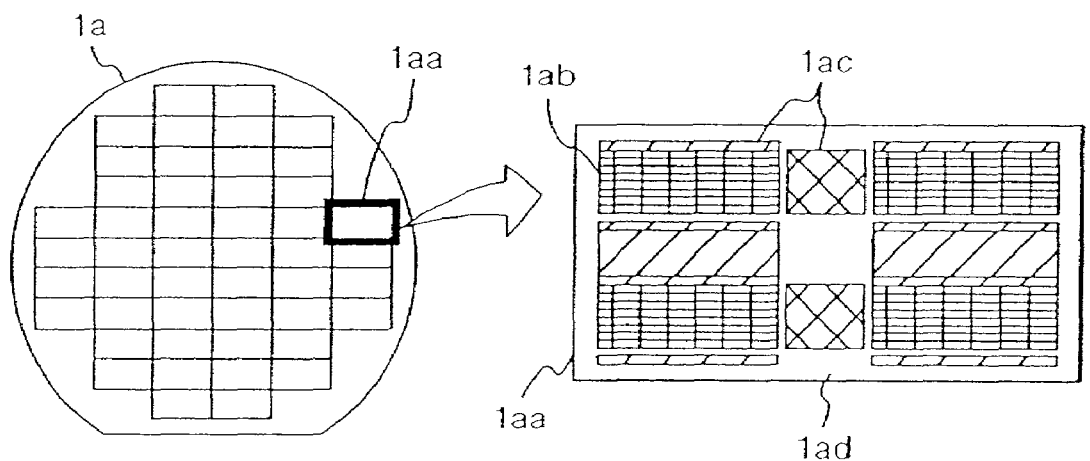
FIG. 1 is a diagram showing a semiconductor wafer serving as a substrate which has memory LSIs laid thereon and is to be inspected by a defect inspecting apparatus implemented by an embodiment of the present invention.
Figure 2:
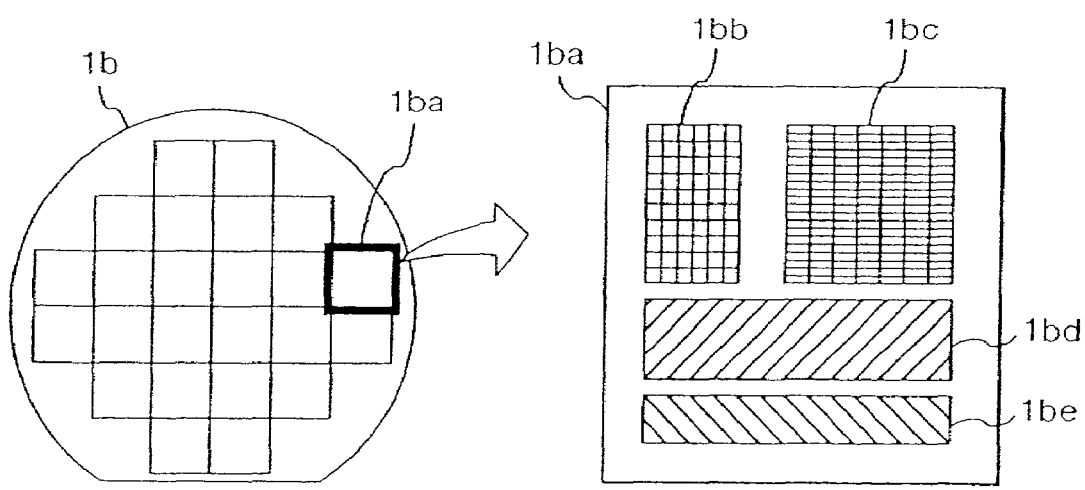
FIG. 2 is a diagram showing a semiconductor wafer serving as a substrate which has LSIs such as microcomputers laid thereon and is to be inspected by the defect inspecting apparatus implemented by another embodiment of the present invention.

First of all, an inspection object 1 including a defect such as a foreign particle to be inspected is explained by referring to FIGS. 1 and 2.

A typical inspection object 1 including a defect such as a foreign particle to be detected is a semiconductor wafer 1a on which chips 1aa each to be produced as a memory LSI are laid out 2-dimensionally at predetermined intervals as shown in FIG. 1. Each of the memory chips 1aa each to be produced as a memory LSI includes memory-cell areas 1ab which occupy a largest region, peripheral-circuit areas 1ac each including a decoder and a control circuit and other areas 1ad. In each of the memory-cell area 1ab, a repetitive pattern of memory cells with a minimum line width of typically about 0.1 to 0.3 µm are laid out regularly in 2 dimensions. In a peripheral-circuit area 1ac, on the other hand, a non-repetitive pattern of memory cells with a minimum line width of typically about 0.2 to 0.4 µm are laid out irregularly in 2 dimensions. An example of the other areas 1ad is a bonding area with a minimum line width of typically about 10 µm including substantially no pattern.

Another typical inspection object 1 including a defect such as a foreign particle to be detected is a semiconductor wafer 1b on which chips 1ba each to be produced typically as a microcomputer LSI are laid out 2-dimensionally at predetermined intervals as shown in FIG. 2. Each of the chips 1ba each to be produced typically as a microcomputer LSI includes main areas such as a register-set area 1bb, a memory-unit area 1bc, a CPU-core area 1bd and an input/output-unit area 1be. It should be noted that FIG. 2 conceptually shows the memory-unit area 1bc and the register-set area 1bb each as a matrix to indicate a repetitive matrix but shows the CPU-core area 1bd and the input/output-unit area 1be each as a hatched area to represent a non-repetitive pattern. In the register-set area 1bb and the memory-unit area 1bc, a repetitive pattern of elements with a minimum line width of typically about 0.1 to 0.3 µm are laid out regularly in 2 dimensions. In the CPU-core area 1bd and the input/output-unit area 1be, on the other hand, a non-repetitive pattern of elements with a minimum line width of typically about 0.1 to 0.3 µm are laid out irregularly in 2 dimensions.

As described above, on a semiconductor wafer used as an inspection object 1 including a defect such as a foreign particle to be detected, chips are laid out regularly. However, a chip has a minimum line width which varies from area to area. In addition, elements in a chip may form a repetitive pattern, a non-repetitive pattern or no pattern. Thus, the inspection object 1 can have a variety of possible forms.

Figure 12:
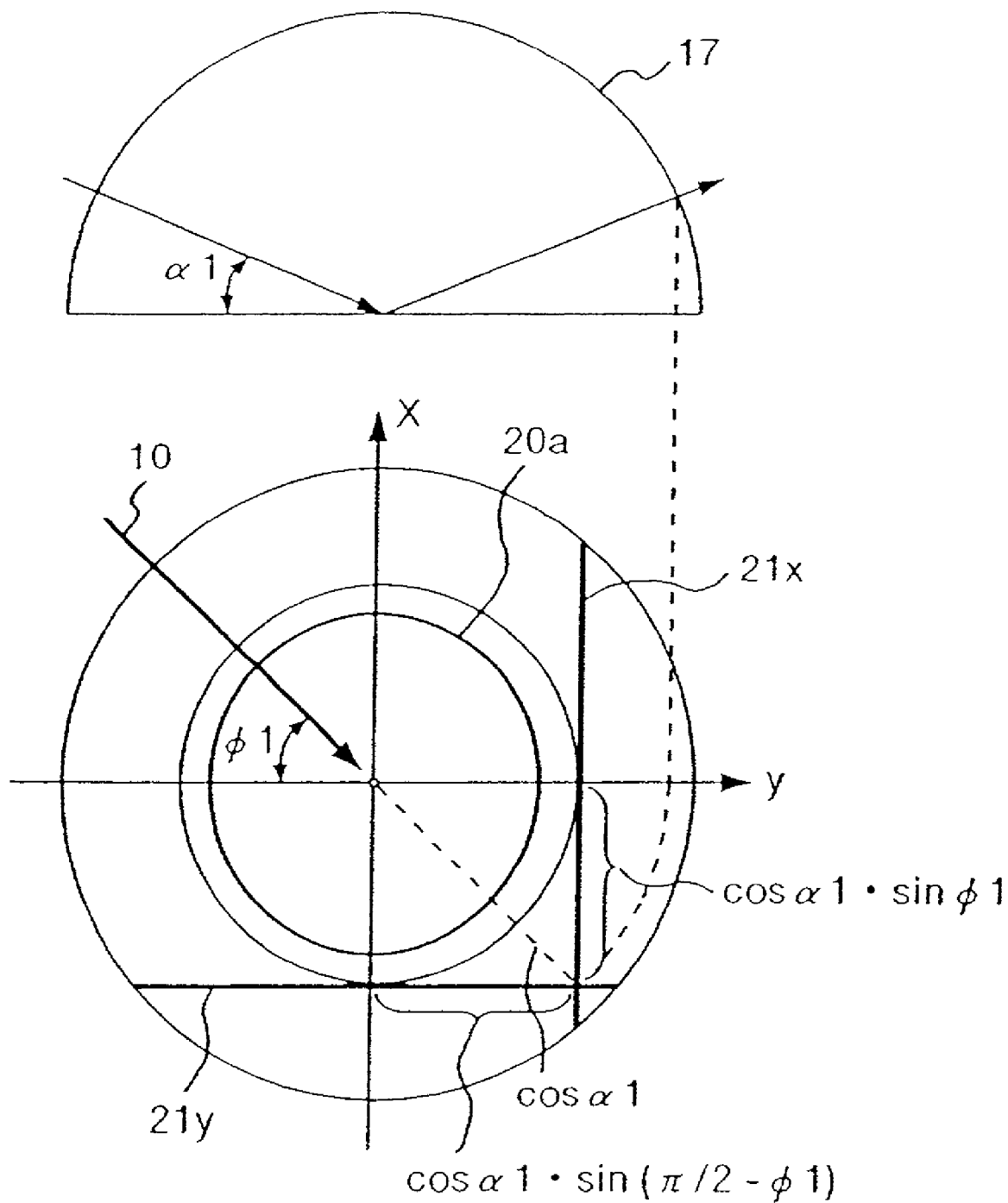
FIG. 12 is a diagram showing a relation between: a state of generation of a 0th-order diffraction-light pattern by radiation of a slit-shaped beam in a direction forming an angle of 45 degrees with a group of main straight lines of a circuit pattern according to the present invention; and an aperture of an objective lens employed in a detection optical system with an optical axis thereof oriented in a vertical direction.
Figure 21:
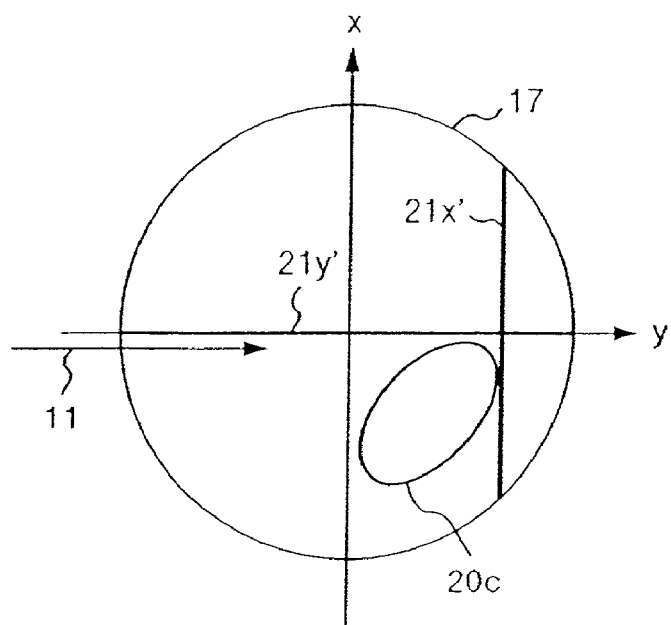

With the defect inspecting apparatus and the defect inspection method provided by the present invention to detect a defect such as a foreign particle, a 0th-order diffraction light coming from a line-shaped pattern comprising a group of straight lines in a non-repetitive-pattern area in a chip on such an inspection object 1 is prevented from hitting incidence eyes 20a and 20c of an objective lens as shown in FIGS. 12 and 21. At the same time, scattered lights coming from a defect such as a foreign particle existing in the non-repetitive-pattern area are received as a detection signal from the defect such as a foreign particle so that the coordinates of the position of the defect can be determined.

In addition, while there may be variations in background signal caused by subtle differences among processes, which do not indicate a defect, and noise observed in the detection, with the defect inspecting apparatus and the defect inspection method provided by the present invention to detect a defect such as a foreign particle, it is possible to improve the sensitivity to detect a defect such as a foreign particle and the throughput by setting a threshold value used as a criterion in the extraction of such a defect.

Figure 3:
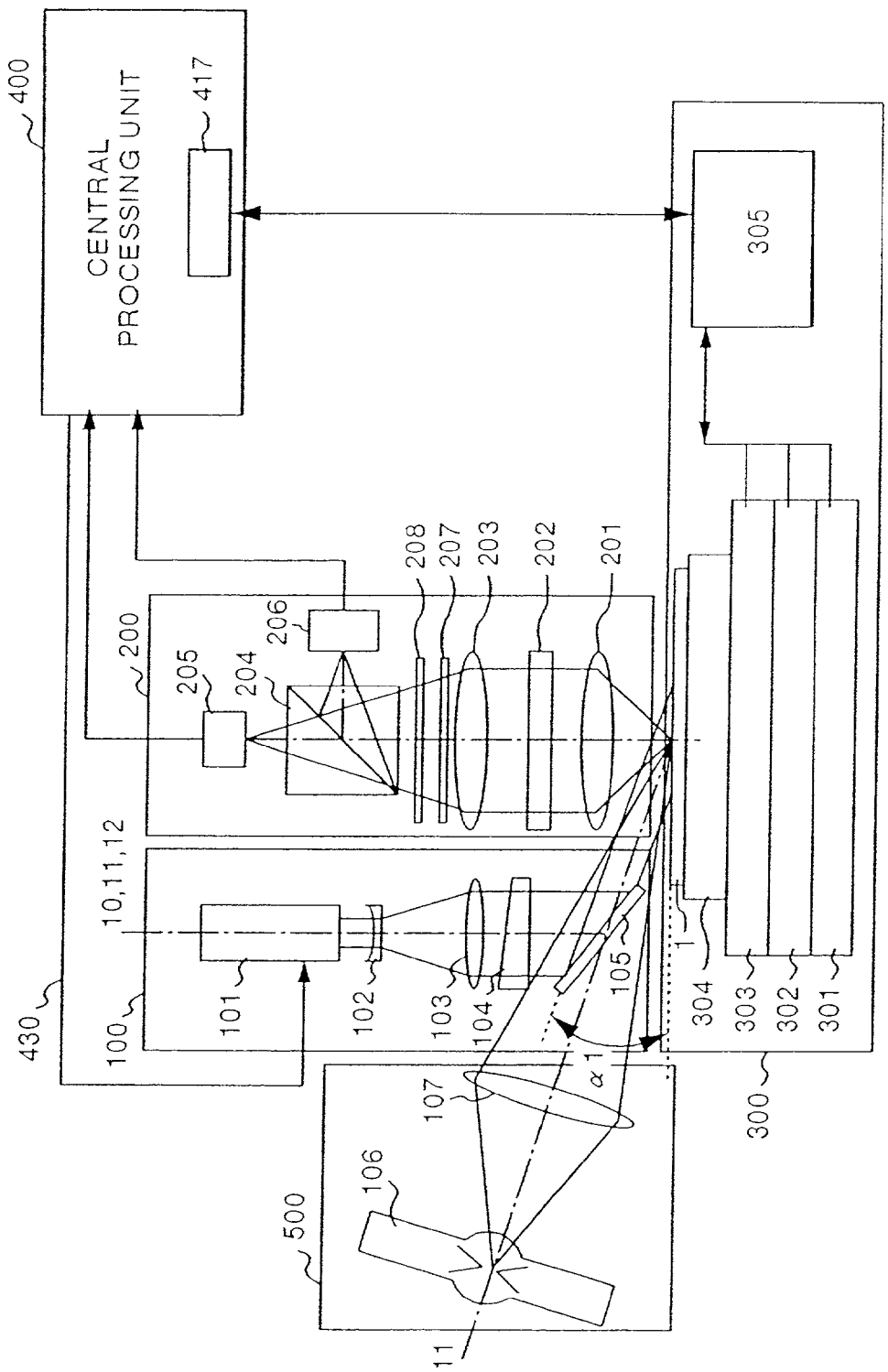
FIG. 3 is a diagram showing the configuration of a first embodiment implementing a defect inspecting apparatus provided by the present invention in a simple and plain manner.
Figure 4:
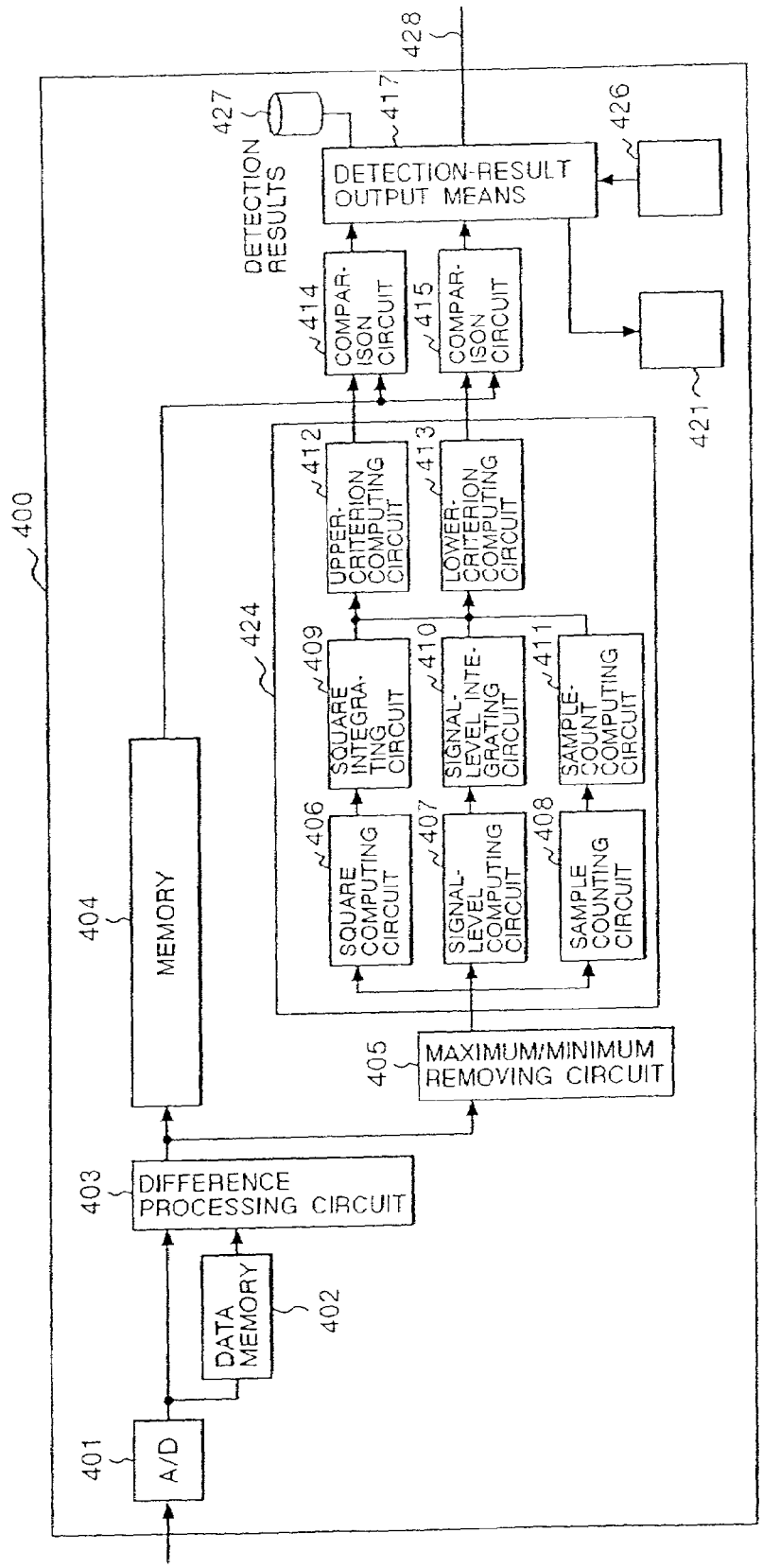
FIG. 4 is a block diagram showing the configuration of a second embodiment implementing an image-signal processing unit employed in the defect inspecting apparatus shown in FIG. 3.

The following description explains a first embodiment implementing a defect inspecting apparatus provided by the present invention to detect a defect such as a foreign particle by referring to FIGS. 3 and 4.

As shown in FIG. 3, the first embodiment implementing a defect inspecting apparatus for detecting a defect such as a foreign particle comprises: a stage unit 300 comprising a substrate mounting base 304, x, y and z stages 301, 302 and 303 and a stage controller 305; 3 illumination optical systems 100 having a laser-beam source 101, a beam splitter comprising a concave lens 102 and a convex lens 103 and an illumination lens 104 having a conical surface; a detection optical system 200 including a detection lens 201, a spatial filter 202, an image formation lens 203, an ND (Neutral Density) filter 207, a beam splitter 204, a polarization device 208 and one-dimensional detectors (image sensors) 205 and 206 which are each implemented typically by a TDI image sensor; an image-signal processing unit 400 shown in detail in FIG. 4; and a white-color optical system 500 comprising a white-color light source 106 and an illumination lens 107.

In particular, it is desirable to employ a TDI image sensor of an anti-blooming type. By employing a TDI image sensor of an anti-blooming type, inspection of a substrate for a defect such as a foreign particle in an area in close proximity to a saturation zone becomes possible.

As shown in FIG. 4, the image-signal processing unit 400 includes: an A/D converter 401; a data memory 402 for delaying a signal by a time to inspect 1 chip of typically a substrate on which chips are always laid out as a repetitive pattern; a difference processing circuit 403 finding a difference between signals coming from chips; a difference memory 404 for temporarily storing differences in signal between chips; a maximum/minimum removing circuit 405 for removing signals representing an abnormal maximum and an abnormal minimum of the differences in signal; a square computing circuit 406 for computing the square of a signal level s; a signal-level computing circuit 407 for computing the signal level s; a sample counting circuit 408 for counting the number of samples; a square integrating circuit 409 for integrating the square of the signal level s; a signal-level integrating circuit 410 for integrating the signal level s; a sample-count computing circuit 411 for computing a sample count n for finding a variation; an upper-criterion computing circuit (a positive-threshold-value computing circuit) 412; a lower-criterion computing circuit (a negative-threshold-value computing circuit) 413; a comparison circuit 414 for the upper-criterion computing circuit 412; a comparison circuit 415 for the lower-criterion computing circuit 413; and a detection-result output means 417 for storing and outputting a result of detection of a defect such as a foreign particle.

The image-signal processing unit 400 will be described in detail later.

Figure 5:
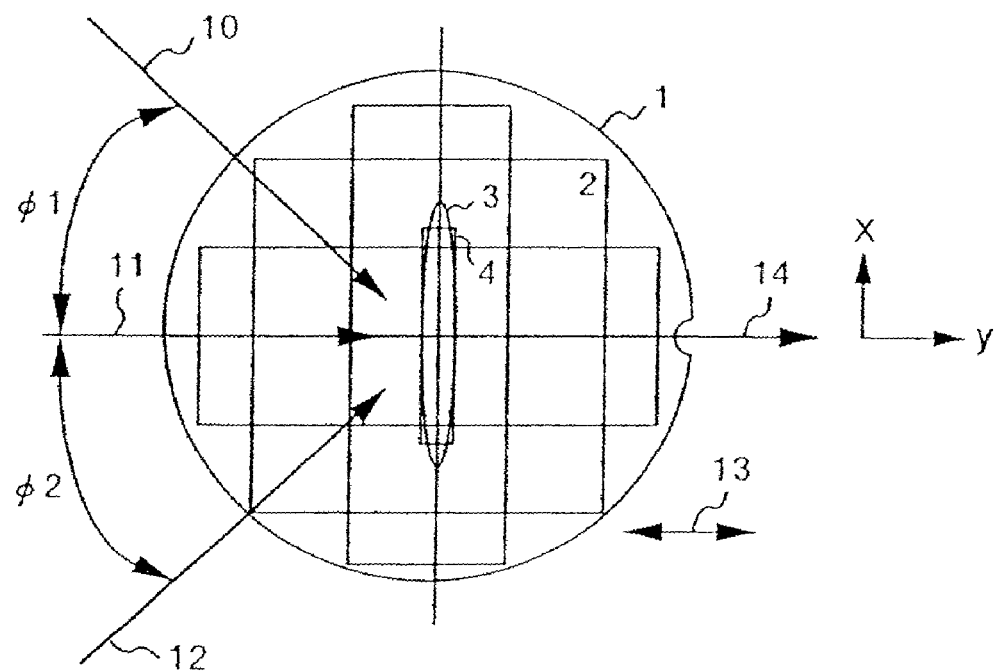
FIG. 5 is an explanatory diagram used for describing a method provided by the present invention to radiate a slit-shaped beam to a substrate being inspected such as a semiconductor wafer and a method provided by the present invention to detect a beam reflected by the substrate.

The 3 illumination optical systems 100 have such a configuration that a light emitted by the laser-beam source 101 passes through the beam splitter comprising the concave lens 102 and the convex lens 103 and then the illumination lens 104 having a conical surface, being converted into slit-shaped beams 3 which are radiated to a wafer 1 or an inspected substrate 1 mounted on the substrate mounting base 304 from 3 directions 10, 11 and 12 on a plane as shown in FIG. 5 with the longitudinal directions of the slit-shaped beams 3 oriented to the layout directions of the chips. It should be noted that the reason why the light emitted by the laser-beam source 101 is converted into the slit-shaped beams 3 is to realize inspection of a substrate for a defect such as a foreign particle at a high speed. That is to say, the slit-shaped beams 3 radiated in the x-axis scanning direction of the x-axis stage 301 and the y-axis scanning direction of the y-axis stage 302 to the surface of the wafer 1 on which chips 2 are laid out each have a shape resembling a slit which is narrow in the y-axis scanning direction of the y-axis stage 302 but wide in the vertical direction, that is, the x-axis scanning direction of the x-axis stage 301 as shown in FIG. 5. In this way, the slit-shaped beams 3 are radiated to form an image of the laser-beam source 101 in the direction of the y axis but radiated as parallel beams in the direction of the x axis. It should be noted that the slit-shaped beams 3 can be radiated from the 3 directions 10, 11 and 12 individually or radiated in such a way that those from the 2 directions 10 and 12 are radiated at the same time.

Figure 14:
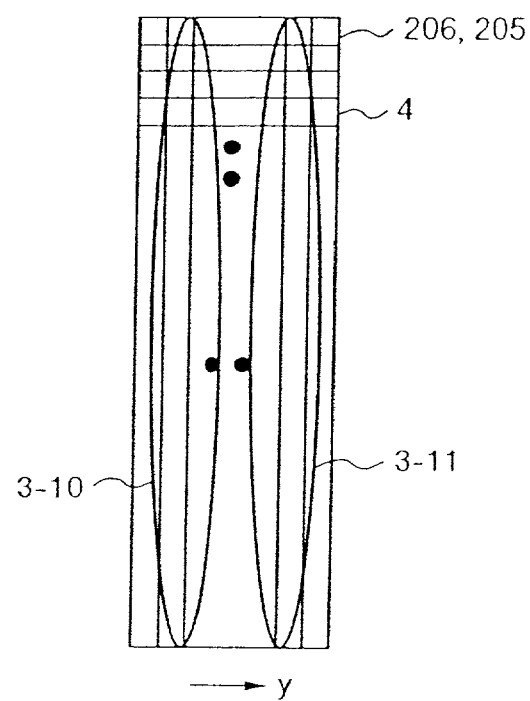
FIG. 14 is a diagram showing a relation between: slit-shaped beams radiated in 3 different directions each forming an angle of 45 degrees with a group of main straight lines of a circuit pattern according to the present invention; and a detection area detected by a TDI image sensor.

By the way, the reason why the longitudinal directions of the slit-shaped beams 3 radiated to the wafer (inspected substrate) 1 are oriented in the layout direction of the chips on the wafer 1 perpendicularly to the y-axis scanning direction of the y-axis stage 302 is to sustain an integration direction of the TDI image sensors 205 and 206 in an orientation parallel to the scanning direction of the stage. In this way, as shown in FIG. 14, an ordinary TDI image sensor can be employed and, in addition, image signals coming from different chips can be compared with each other in a simple way. At the same time, coordinates of the position of a detected defect can be found with ease. As a result, is possible to realize inspection of a substrate for a defect such as a foreign particle at a high speed. In particular, the illumination lens 104 having a conical surface is required in order to orient the slit-shaped beams 3 radiated to the wafer (inspected substrate) 1 from the directions 10 and 12 in the layout direction of chips on the wafer 1 perpendicularly to the y-axis scanning direction of the y-axis stage 302.

Figure 6:
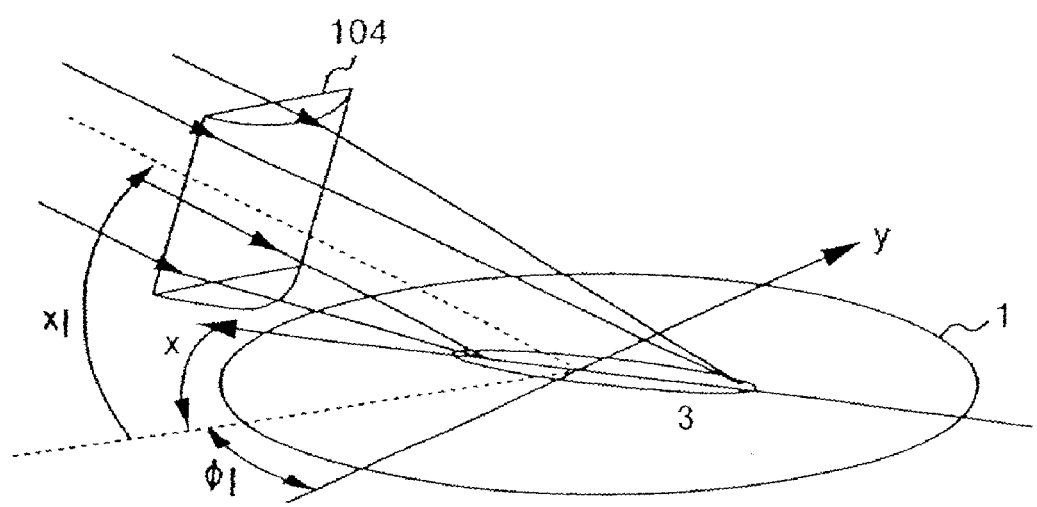
FIG. 6 is a diagram showing a squint view of a light beam radiated by an illumination lens with a conical surface provided by the present invention.
Figure 9A:
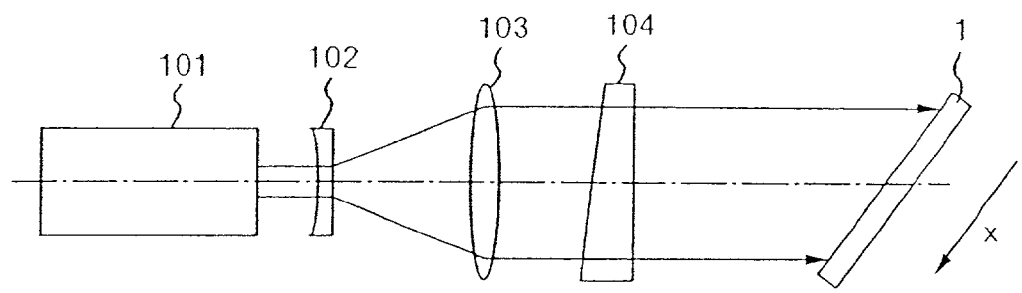
FIG. 9(a) is a diagram showing a side view in the direction of the y axis of an illumination optical system provided by the present invention and FIG. 9(b) is a diagram showing a side view in the direction of the x axis of the illumination optical system provided by the present invention.

FIG. 6 is a diagram showing the illumination lens 104 having a conical surface. The illumination lens 104 has a cylindrical shape with focal distances varying at locations along the longitudinal direction of the cylindrical shape. That is to say, the illumination lens 104 is a lens with a linearly varying focal distance. Even if beams are radiated in a slanting direction at gradients φ1 and α as shown in FIG. 6, it is possible to convert the beams into a slit-shaped beam 3 which is converged in the direction of the y axis and collimated in the direction of the x axis. That is to say, by using the illumination lens 104, it is possible to radiate parallel beams in the direction of the x axis as shown in FIG. 9(a) at a gradient φ1 of approximately 45 degrees. By radiating the parallel slit-shaped beams 3 in the direction of the x axis as shown in FIG. 9(a), a diffraction-light pattern can be obtained from a circuit pattern with its group of main straight lines oriented in the directions of the x and y axes, allowing the beams 3 to be shielded by the spatial filter 202.

Figure 7:
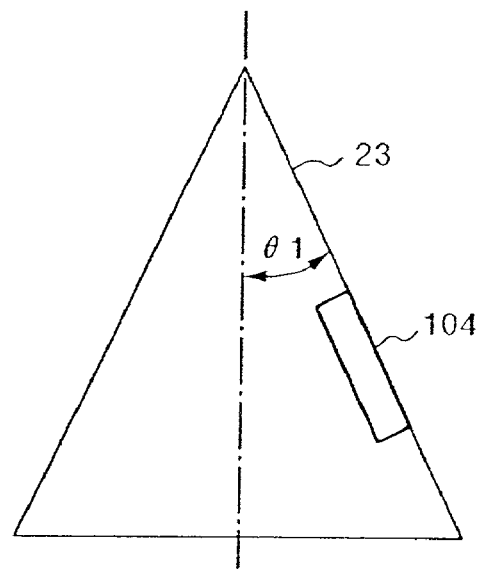
FIG. 7 is an explanatory diagram used for describing a first embodiment implementing a method to manufacture an illumination lens with a conical surface provided by the present invention.
Figure 8:
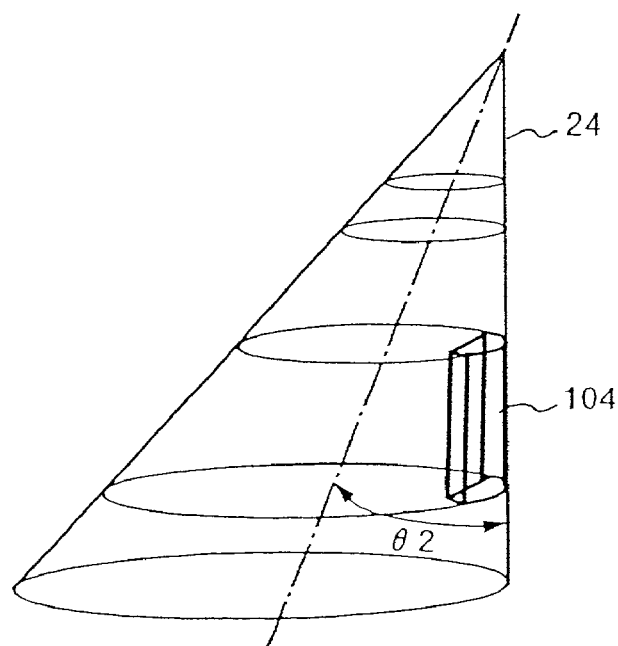
FIG. 8 is an explanatory diagram used for describing a second embodiment implementing a method to manufacture an illumination lens with a conical surface provided by the present invention.

Next, a method to manufacture the illumination lens 104 having a conical surface is explained by referring to FIGS. 7 and 8. Made of a material such as glass or quartz, a cone 23 having a predetermined bottom area and a predetermined height is created in a polishing process. Then, a lens is cut out from the cone 23 at a predetermined cross section to make the lens 104 having a conical surface. A curved surface of a lens naturally required in the present invention like the one shown in FIG. 6 is actually not a conical surface but must be a curved surface 24 like one shown in FIG. 8. Since the cubic body shown in FIG. 8 is not a not a body symmetrical with respect to an axis of rotation, however, it is difficult to polish such a body. For this reason, the lens 104 is approximated by the cone 23 shown in FIG. 7. There will be no problem in practical use provided that the lens has an N. A. in the range 0.02 to 0.2.

For the shape of the surface of the cone 23 shown in FIG. 7, Eq. (1) given below holds true:

$$x^2+y^2=(z \times \tan \theta 1)^2 \qquad (1)$$

where the symbol θ1 is the vertical angle with the vertex of the cone 23 positioned at the origin.

As for the curved surface 24 shown in FIG. 8, Eq. (2) given below holds true:

$$(x-z \times \tan \theta 2)^2+y^2=(z \times \tan \theta 2)^2 \qquad (2)$$

where the symbol θ2 is likewise the vertical angle with the vertex of the cone 23 positioned at the origin.

It should be noted that the method of making the conical lens 104 is not limited to what is described above. For example, it is also possible to adopt another technique such as an injection molding technique whereby a material such as plastic is flowed into a mold with a conical surface made in advance. As another method, there is also known a technique whereby a glass substrate is mounted on a conical surface made in advance and the substrate is then melted.

Figure 9B:
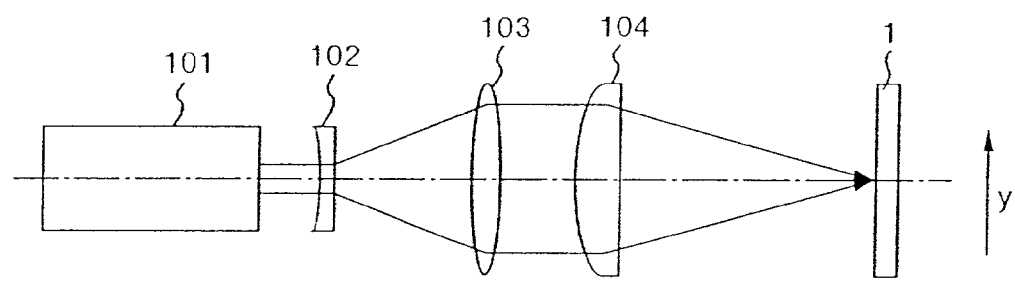

The conical lens 104 provided by the present invention implements illumination which is critical in the direction of the y axis and collimated in the direction of the x axis. Configurations for such implementation are shown in FIGS. 9(a) and 9(b). A light emitted by the laser-beam source 101 is radiated to the conical lens 104 by way of a beam expander comprising the concave lens 102 and the convex lens 103. In the conical lens 104, the light is radiated in a collimated form due to the fact that there is no lens effect in the direction of the x axis. In addition, since the curvature at one edge of the conical lens 104 is different from the curvature at the other edge, the conical lens 104 has different focal distances. At the same time, the light is focused on the surface of the wafer 1 by the curvatures of the conical lenses in the direction of the y axis.

Figure 10:
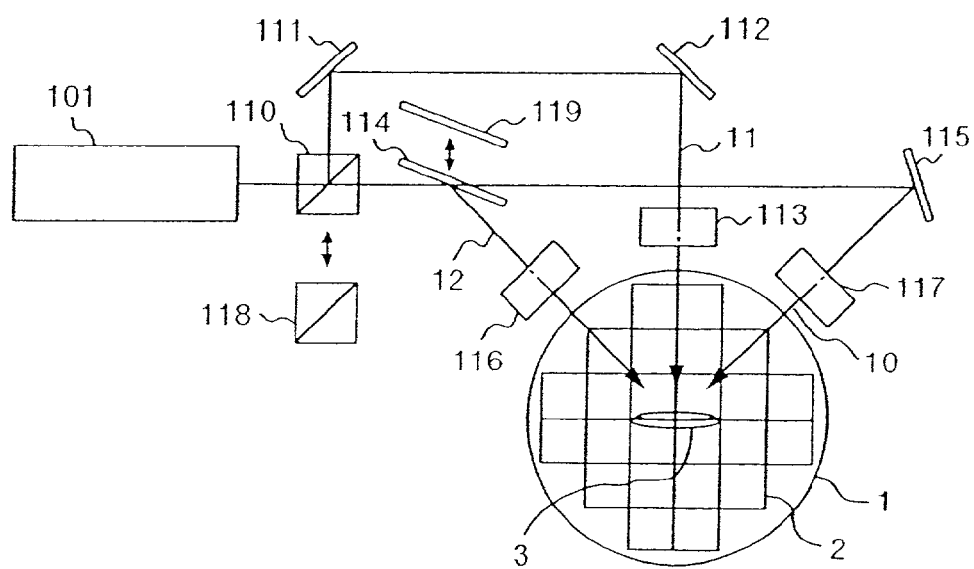
FIG. 10 is a diagram showing a top view of an optical subsystem for radiating slit-shaped beams generated by a single laser-beam source in 3 directions to a substrate being inspected such as a semiconductor wafer in the illumination optical system provided by the present invention.

FIG. 10 shows a top view of the 3 illumination optical systems 100 which employ a single laser-beam source 101. A laser beam emitted by the laser-beam source 101 is split by an optical splitting element 110 implemented typically by a half mirror into 2 paths. A laser beam along one of the optical paths is reflected by mirrors 111 and 112 before being directed by a mirror 113 downward toward the concave lens 102. As a result, an illumination beam from a direction 11 is obtained. A laser beam along the other optical path travels to an optical splitting element 114 also implemented typically by a half mirror. At the optical splitting element 114, the laser beam is further split into to two paths. A laser beam along one of the optical paths is reflected by a mirror 115 before being directed by a mirror 117 downward toward the concave lens 102. As a result, an illumination beam from a direction 10 is obtained. A laser beam along the other optical path is directed by a mirror 116 downward toward the concave lens 102. As a result, an illumination beam from a direction 10 is obtained.

When it is desired to radiate a laser beam to the concave lens 102 only from the direction 11, by the way, the optical splitting element 110 can be replaced by a mirror element 118. When it is desire to radiate laser beams to the concave lens 102 only from the directions 10 and 12, on the other hand, the optical splitting element 110 is just removed from the optical paths or replaced with a proper optical device. Likewise, when it is desired to radiate a laser beam to the concave lens 102 only from the direction 12 without the laser beam from the direction 10, the optical splitting element 114 can be replaced by a mirror element 119.

It should be noted that, as the laser-beam source 101, it is possible to employ a high-output YAG laser SHG for generating a second harmonic wave with a wavelength of 532 nm for a splitting reason even though the wavelength does not have to be 532 nm. In addition, the laser-beam source does not have to be a YAG laser SHG. That is to say, as the laser-beam source 101, it possible to use a source of another kind such as an Ar laser, a nitrogen laser, an He—Cd laser or an exima laser.

In the detection optical system 200, a light emitted by the wafer 1 passes through the detection lens (objective lens) 201, the spatial filter 202, the image formation lens 203, the ND filter 207, the polarization device 208 and the beam splitter 204 before being inspected by the detectors 205 and 206 which are each implemented typically by a TDI image sensor. The spatial filter 202 shield s a Fourier-transformation image formed by a diffraction light reflected by a repetitive pattern. The ND filter 207 adjusts the quantity of light without regard to wavelength bands. The spatial filter 202 is placed in a spatial-frequency area of the objective lens 201 at which a Fourier-transformation image formed by a diffraction light reflected by a repetitive pattern is to be shielded. That is to say, the spatial filter 202 is placed at an image formation position of the Fourier transformation which corresponds to an emission eye. The polarization device 208 shields polarization components of reflected scattered lights which are generated by an edge of a circuit pattern when the illumination optical system 100 radiates a polarization light. However, the polarization device 208 passes some polarization components of reflected scattered lights which are generated by a defect such as a foreign particle. Thus, the polarization device 208 is not necessarily required by the present invention. In the detection optical system 200, an image of an illuminated area 4 on the wafer 1 shown in FIG. 5 is formed on the detectors 205 and 206 by the image formation lens 203 and the objective lens 201 serving as a relay lens. That is to say, reference numeral 4 also denotes a photo-sensitive area on the detectors 205 and 206 which are each implemented by typically a TDI image sensor as described above.

When slit-shaped beams 3 are radiated to the wafer (substrate) 1 having a variety of circuit patterns formed thereon, reflected diffraction lights or scattered lights are emitted from the surface of the wafer 1, the circuit patterns and defects such as foreign particles. Each of the emitted lights travels to the detectors 205 and 206 by way of the detection lens 201, the spatial filter 202, the image formation lens 203, the ND filter 207, the polarization device 208 and the beam splitter 204. In the detectors 205 and 206, the light is converted into an electrical signal.

It should be noted that the shown order in which the ND filter 207, the polarization device 208 and the beam splitter 204 are placed along the optical path is typical. In particular, if the ND filter 207 is placed behind the beam splitter 204, the intensities of light beams arriving at the detectors 205 and 206 can be controlled independently of each other.

In addition, the transmittance and reflectance rates of the beam splitter 204 do not have to be 50%. For example, the transmittance rate and the reflectance rate can be set at 1% and 99% respectively. By setting the transmittance and reflectance of the beam splitter 204 at such values that the intensity of the beam hitting one of the detectors 205 and 206 is about 1/100 of the intensity of the beam hitting one of the other detector in this way, signals will be generated by the 2 detectors 205 and 206 which receive beams having different intensities. Thus, the dynamic range of the detectors 205 and 206 appears improved. As a result, the image-signal processing unit 400 is capable of obtaining a detection signal of a defect such as a foreign particle with an improved dynamic range from signals generated by the detectors 205 and 206. In particular, a signal generated by one of the detectors 205 and 206 as a result of a photo-electrical conversion of a light with a large intensity has its a large-intensity component indicating a defect emphasized. On the other hand, a signal generated by the other detector as a result of a photo-electrical conversion of a light with a small intensity has its a small-intensity component close to the background also emphasized. Accordingly, by identifying a correlation between the 2 emphasized signals such as the ratio of the signal to the other, the dynamic range of a signal representing a defect can be enhanced.

By adjusting the illumination (power) of a beam radiated by the laser-beam source 101 employed in the illumination optical systems 100, the dynamic range can also be changed. Thus, the beam splitter 204 and one of the detectors 206 can be eliminated.

The following description explains a relation between the slit-shaped beam 3 radiated by the illumination optical system 100 provided by the present invention to the wafer 1 and the detection optical system 200 also provided by the present invention in concrete terms. FIG. 5 is a diagram showing a top view of directions of illumination by the slit-shaped beam 3 and a direction of detection by the one-dimensional detectors 205 and 206 which are each implemented typically by a TDI image sensor as described earlier. In the example shown in the figure, the slit-shaped beam 3 illuminates the wafer 1 on which a pattern 2 is formed. Reference numeral 4 denotes an image formed by the one-dimensional detectors 205 and 206 employed in the detection optical system 200. Slit-shaped beams 3 are radiated to the wafer 1 from directions 10, 11 and 12 on a plane.

Figure 11A:
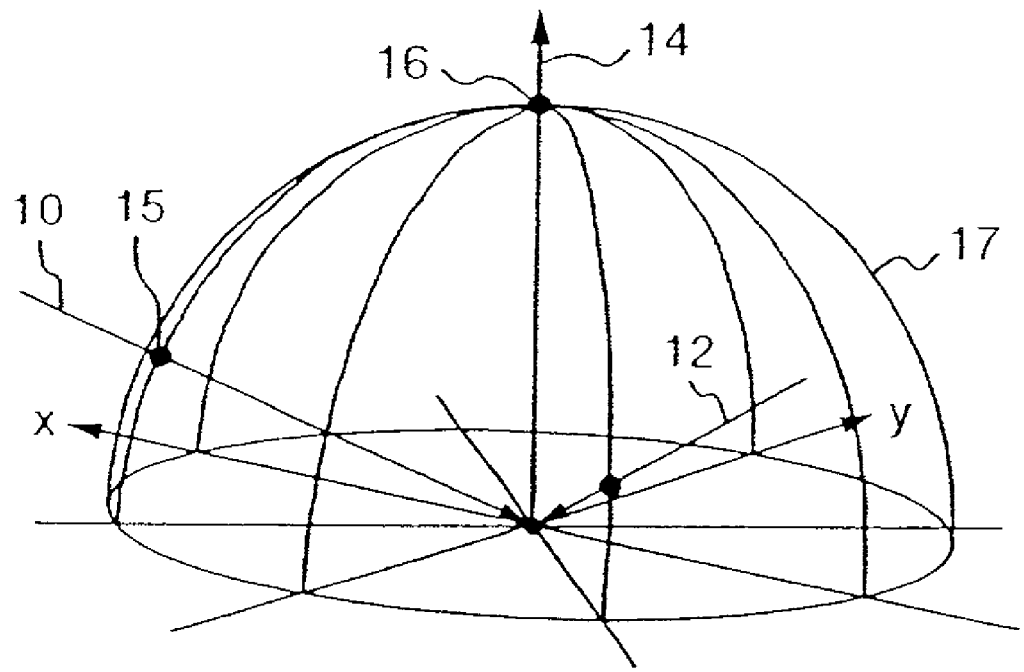

FIG. 11(a) is an explanatory diagram for supplementing FIG. 5. In FIG. 11(a), reference numeral 10 denotes an illumination direction and reference numeral 14 denotes a detection direction perpendicular to the surface of a wafer 1 on which the axes x and y are laid. A spherical surface 17 is an imaginary surface assumed in thinking of an aperture position of the objective lens 201 employed in the detection optical system 100 shown in FIG. 5. An illumination light traveling in the direction 10 and a detection light traveling in the direction 14 intersect the spherical surface 17 at cross points 15 and 16 respectively.

Figure 11B:
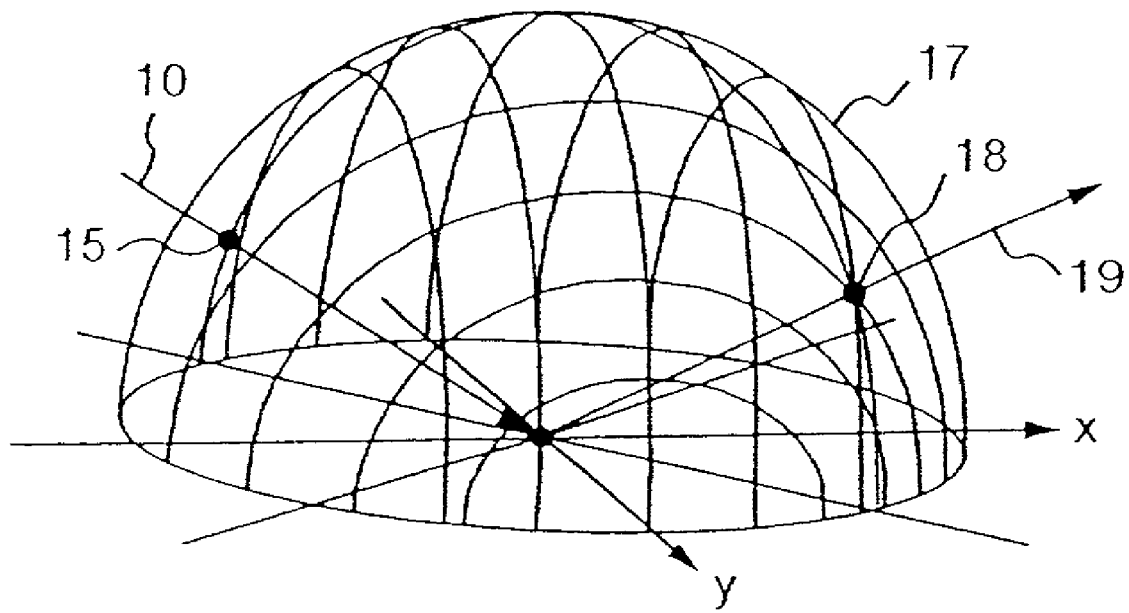
FIG. 11(b) is a diagram showing a birds eye view of a diffraction light obtained as a result of reflection of a light radiated in the radiation direction by a pattern.

On the other hand, FIG. 11(b) is a diagram showing the state of emission of a diffraction light which is obtained as a result of an illumination in the direction 10. A light resulting from true reflection of the illumination light in the direction 10 travels in an emission direction 19, intersecting the spherical surface 17 at a cross point 18. This light traveling in the emission direction 19 is referred to as a 0-order light. Imagine a cone oriented upside down perpendicularly to the plane of the x and y axes with the vertex thereof coinciding with a point of illumination on the plane as shown in FIG. 7(b). The beam 3 traveling in the illumination direction 10 and the reflected 0th-order light traveling in the emission direction 19 form the sides of a longitudinal cross section of the cone. That is to say, a locus of the intersection point of the reflected 0th-order light traveling in the emission direction 19 and the imaginary spherical surface 17 form the circumference of the bottom of the cone.

Thus, when seen from the direction of the normal line, the locus is a straight line parallel to the x and y axes.

Figure 13:
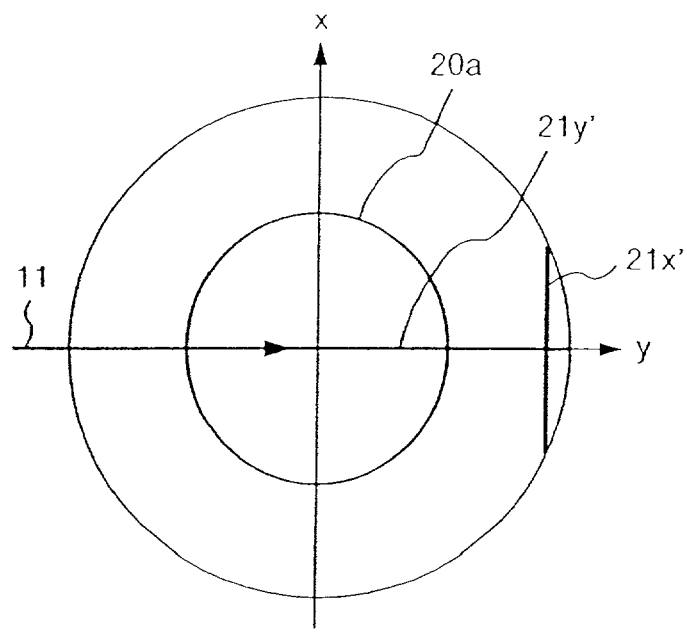
FIG. 13 is a diagram showing a relation between: a state of generation of a 0th-order diffraction-light pattern by radiation of a slit-shaped beam in a direction parallel to a group of main straight lines of a circuit pattern according to the present invention; and an aperture of an objective lens, employed in a detection optical system with an optical axis thereof oriented in a vertical direction.

By the way, reference numeral 20a shown in FIGS. 12 and 13 denotes the aperture of the objective lens 201 employed in the detection optical system 200 which is not inclined or has a gradient β1 of 0.

In this case, assume that angles φ1 and φ2 formed by the illumination directions 10 and 12 with the y axis respectively are both set at a typical value of about 45 degrees. With the optical axis of the detection optical system 200 oriented perpendicularly to the surface of the wafer 1, that is, with the gradient β1 set at 0, as shown in FIG. 3, the numerical aperture (N.A.) of the detection lens (objective lens) 201 and the angle α1 of the illumination light shown in FIG. 3 should be set in a range defined by relations (3) shown below with a condition that the 0th-order diffraction lights 21x and 21y generated by a circuit pattern with its group of main lines thereof oriented in the directions of the x and y axes respectively are guided not to enter the eye of the detection lens 201 as shown in FIG. 12. That is to say, by setting the angles φ1 and φ2 formed by the illumination directions 10 and 12 with the y axis respectively both at a typical value of about 45 degrees and by setting the numerical aperture (N.A.) of the detection lens (objective lens) 201 and the angle α1 of the illumination light shown in FIG. 3 in a range satisfying relations (3) shown below, the 0th-order diffraction lights 21x and 21y generated by a circuit pattern with its group of main lines thereof oriented in the directions of the x and y axes respectively can be prevented from entering the aperture 20a of the detection lens 201 even if the circuit pattern is a non-repetitive pattern.

$$N.A. < \cos \alpha1 \times \sin \phi1 \text{ and}$$

$$N.A. < \cos \alpha1 \times \sin(\pi/2 - \phi1) \quad (3)$$

It should be noted that, for α1 equal to or smaller than 30 degrees, the numerical aperture (N.A.) of the objective lens 201 can be set at a value equal to about 0.4 or smaller.

These conditions are specially effective for products such as a peripheral-circuit area 1ac having a non-repetitive pattern on a memory LSI 1aa, an input/output-unit area 1be and a CPU-core area 1bd having a non-repetitive pattern on an LSI 1ba such as a microcomputer and a logic LSI having a non repetitive pattern.

In many cases, LSI patterns are each created in a perpendicular-parallel posture, that is, to contain a group of parallel and perpendicular main straight lines. Thus, 0th-order lights are emitted by these patterns in a specific direction. For this reason, by preventing the 0th-order lights emitted by these patterns from hitting the objective lens 201, diffraction lights emitted by most of these patterns can be eliminated, making it possible to detect only a diffraction light reflected by a defect such as a foreign particle with ease. To put it concretely, there are an increased number of areas which contain a defect such as a foreign particle detectable with a high degree of sensitivity due to the fact that the level of a detection signal generated by the circuit pattern is lowered.

As a mater of course, in the case of a non-repetitive pattern, higher-order (such as the first order, the second order and so on) diffraction lights enter the aperture 20a of the objective lens 201. Thus, higher-order diffraction lights appear as a group of straight lines parallel to the 0th-order diffraction lights 21x and 21y shown in FIG. 12. However, the higher-order diffraction lights can also be eliminated by shielding the lights by using the spatial filter 202 which has a fine band shape.

In addition, it is necessary to inspect the substrate (wafer) 1 for things such as a foreign particle or a defect caught in a dent between protrusions like wires or an etching remnant. As described above, however, it is also necessary to radiate slit-shaped beams 3 having their longitudinal directions oriented in the direction of the x axis to the substrate 1 being inspected from the directions 10 and 12 each forming an angle of about 45 degrees with the y axis in order to prevent a 0th-order diffraction light generated by a non-repetitive pattern existing on the substrate 1 from entering the objective lens 201. In this case, things such as protruding wires serve as a disturbance, making it difficult to provide sufficient illumination.

For the reason described above, in most cases, LSI patterns are each created in a perpendicular-parallel posture, that is, to contain a group of parallel and perpendicular main straight lines as described above so that, by radiating a slit-shaped beam 3 to the substrate 1 from the direction 11 parallel to the y axis, a dent between things such as wires can be illuminated sufficiently. In particular, a wiring pattern of a memory LSI is a straight-line pattern with a length of several mm in many cases so that most inspections can be done by illumination from this direction 11. In addition, in the case of a 90-degree direction for some patterns, an inspection can be done by rotating the wafer by 90 degrees or by orienting the illumination direction in the direction of the x axis.

When radiating the slit-shaped beam 3 from the direction 11, however, the 0th-degree diffraction light 21y' enters the aperture 20a of the objective lens 201 but the 0th-degree diffraction light 21x' does not as shown in FIG. 13. It is thus necessary to eliminate this 0th-degree diffraction light 21y' by shielding the light 21y' using the spatial filter 202. At that time, as a matter of course, the higher-order diffraction lights can also be eliminated by shielding the light 21y' using the spatial filter 202.

The above description explains how to eliminate particularly a 0th-order diffraction light reflected by a non-repetitive pattern in the case of a non-repetitive pattern existing in a chip 2 on the substrate 1 being inspected. However, the chip 2 may be a memory LSI 1*aa* including a memory-cell area 1*ab* or an LSI 1*ba* such a microcomputer including a register-set area 1*bb* and a memory-unit area 1*bc*. Since the memory-cell area 1*ab*, the register-set area 1*bb* and the memory-unit area 1*bc* are repetitive patterns, it is necessary to shield diffraction lights (or diffracted interference light beams) generated by these repetitive patterns by using the spatial filter 202. In a word, a repetitive pattern, a non-repetitive pattern and a non pattern coexist with each other in the chip 2 and, further, the line width varies from pattern to pattern. For this reason, a shielding pattern of the spatial filter 202 is normally set to eliminate a diffraction light generated typically by a repetitive pattern having a high degree of repetitiveness. In addition, in the case of a detection optical system 200 employing a spatial filter 202 with a variable shielding pattern such as ones disclosed in Japanese Patent Laid-open No. Hei 5-218163 (U.S. Pat. No. 5,463,459) and Japanese Patent Laid-open No. Hei 6-258239, the shielding pattern is changed in accordance with a circuit pattern of the chip 2. As an alternative, a plurality of spatial filters 202 with different shielding patterns are provided in advance and one of them appropriate for the circuit pattern in the chip 2 is selected.

The following description explains how to adjust the detection sensitivity in accordance with the size of a defect such as a foreign particle to be detected. That is to say, the detection sensitivity is expected to increase even at the expense of a lower throughput by reducing the size of the detection pixel on the inspection object 1 of the one-dimensional detectors (image sensors) 205 and 206 which are each implemented by typically a TDI image sensor as described above. Thus, when detecting a defect such as a foreign particle with a dimension not exceeding 0.1 µm, the defect inspecting apparatus is switched to a detection optical system 200 which decreases the pixel size. To put it concretely, it is desirable to provide 3 detection optical systems of different types typically appropriate for respectively images with sizes of 2 µm, 1 µm and 0.5 µm on the wafer 1 for pixels such as those of the TDI image sensors. As a technique of implementation of the detection optical system 200, the entire optical system 200 can be replaced by another one, or only the lens (group of lenses) 203 or the lens (group of lenses) 201 is replaced. In this case, the configurations of the lenses may be designed so that the switching can be done without changing the lengths of the optical paths between the wafer 1 and the one-dimensional detectors 205 and 206 which are each implemented by typically a TDI image sensor as described above. If the design is difficult, it is also possible to use a mechanism which tolerates changes in distances to the sensors accompanying switching of the detection optical system 200 from one lens to another. As another alternative, the detection optical system 200 can also be switched from one lens to another with a different pixel size of the sensor itself.

The following description explains a concrete embodiment of a relation between the slit-shaped beams 3 radiated from the 3 directions and the TDI image sensors 205 and 206 by referring to FIG. 14. FIG. 14 is a diagram showing a relation between a TDI image 4 on the wafer 1 and slit-shaped beams 3-10 and 3-12 radiated from the directions 10 and 12 respectively. When beams obtained as a result of splitting a laser beam generated by a single laser-beam source 101 are radiated from the directions 10 and 12 as shown in FIG. 10, the beams interfere each other, resulting in variations in intensity in the illumination zone. In order to solve this problem, the beams 3-10 and 3-12 are radiated in such a way that they do not interfere each other in the zone of the TDI image 4 as shown in FIG. 14 in order to eliminate effects of the interference. When the TDI image sensors 205 and 206 are used, the problem caused by such a positional shift does not arise since detection outputs in the zone of the image 4 are integrated in the direction of the y axis in the zone in synchronization with the movement of the y-axis stage. Also when the slit-shaped beam 3-11 radiated from the direction 11 is used, the beams 3-10, 3-11 and 3-12 are similarly radiated so that they do not interfere each other in the zone, causing a problem of an overlap of the 3 beams. It is needless to say that the problem of interference can be avoided in the same way for any 2 of the 3 slit-shaped beams 3-10, 3-11 and 3-12 radiated from the directions 10, 11 and 12 respectively.

As shown explicitly in none of the figures, when the slit-shaped beams 3-10 and 3-12 are radiated from the directions 10 and 12 respectively to the same location, they will interfere each other. Since the interfering beams are inclined in the direction of the y axis, however, variations in illumination intensity caused by the interference are reduced by an effect of an integration carried out by the TDI image sensors 205 and 206. It is thus not necessary to radiate the slit-shaped beams 10 and 12 so that they do not interfere each other as shown in FIG. 14.

Figure 15:
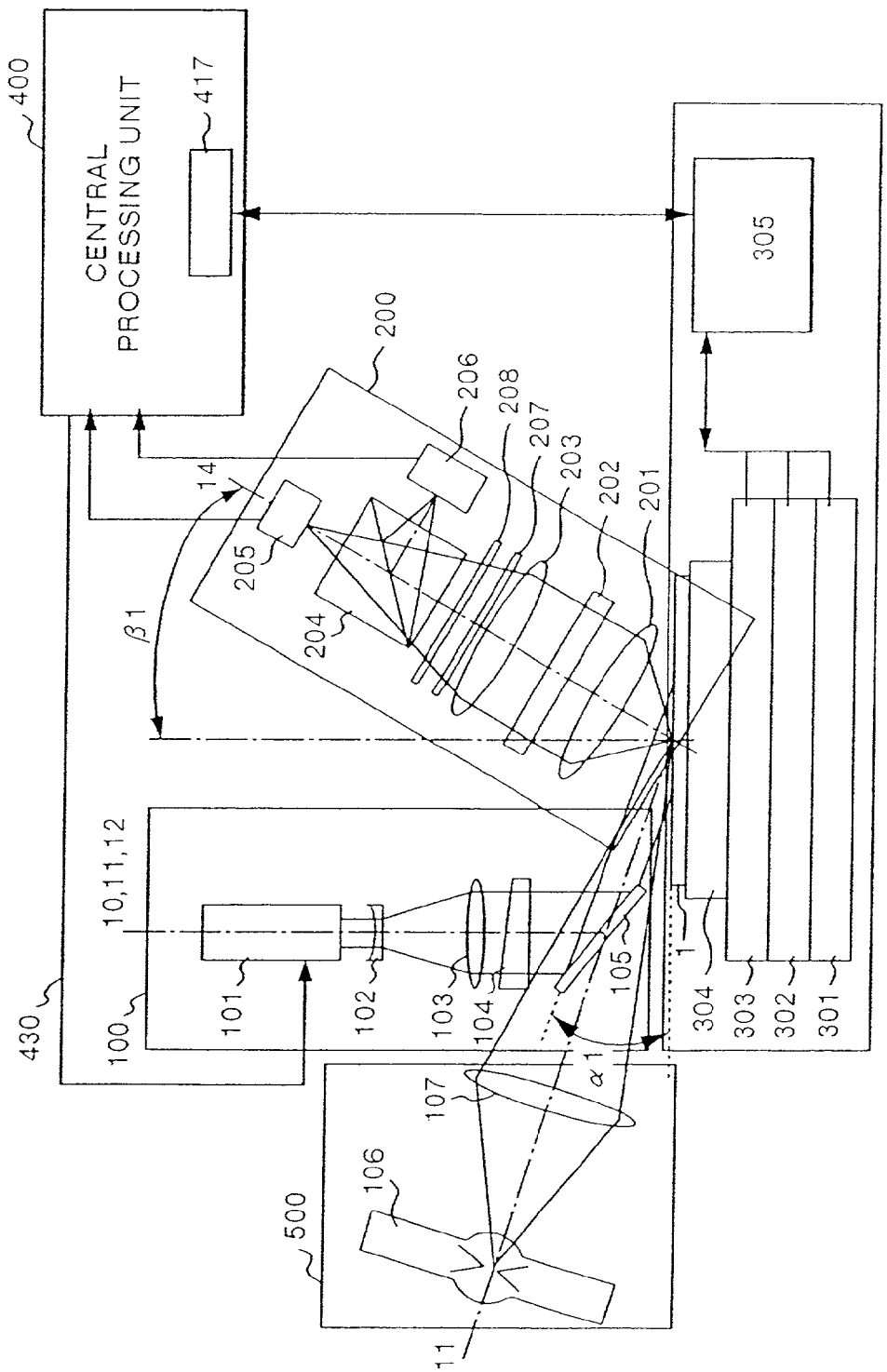
FIG. 15 is a diagram showing the configuration of a second embodiment implementing a defect inspecting apparatus provided by the present invention in a simple and plain manner.

The following description explains a second embodiment implementing a defect inspecting apparatus provided by the present invention for detecting a defect such as a foreign particle by referring to FIG. 15. As shown in the figure, in order to increase the intensity of a scattered light coming from a defect such as a foreign particle, the optical axis of the detection optical system 200 is inclined by an angle β1 from the vertical direction. The rest of the configuration is the same as the first embodiment shown in FIG. 3.

Figure 16:
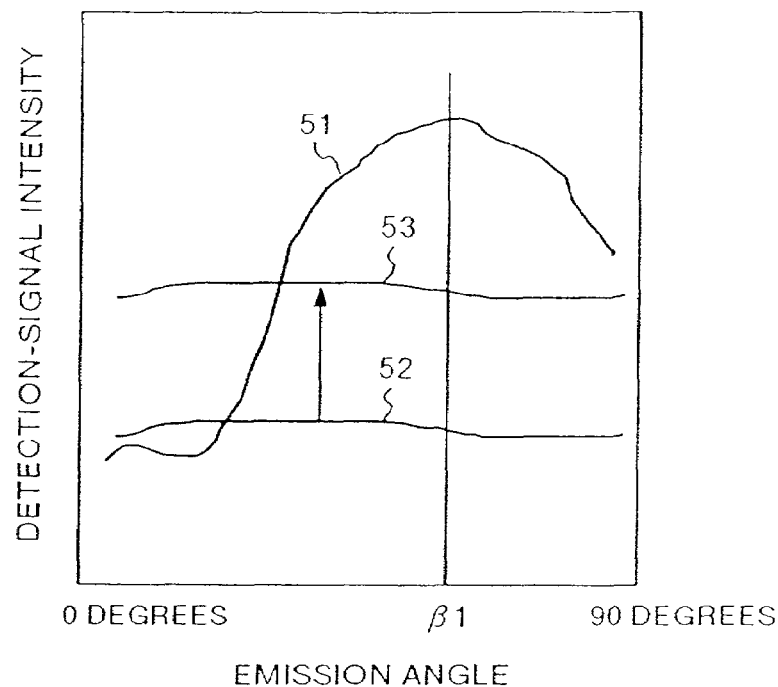
FIG. 16 is a diagram showing graphs each representing a relation between an angle of emission from a foreign particle and the intensity of a detection signal.

The reason why the optical axis of the detection optical system 200 is inclined by an angle β1 from the vertical direction is to increase the intensity of a scattered light coming from a defect such as a foreign particle as shown in FIG. 16 and, hence, to increase the detection sensitivity. The increase in light intensity is attributed to the following cause. A particle or a foreign particle larger in size than a fraction of the illumination wavelength generates a light 51 with a high intensity scattered in the forward direction. On the other hand, a light 52 generated by an area such as a dry spot with a size close to 1/10 of the wavelength or smaller is scattered almost in the forward direction so that the intensity of the scattered light from the infinitesimal particle in the forward direction is relatively high. As a result, if there are a plurality of dry spots on the surface of a circuit pattern among detection pixels, the total intensity is represented by a curve 53 shown in FIG. 16. Thus, by taking the scattered lights traveling in the forward direction, an infinitesimal particle or a defect can be detected from a surface dry spot.

Figure 17:
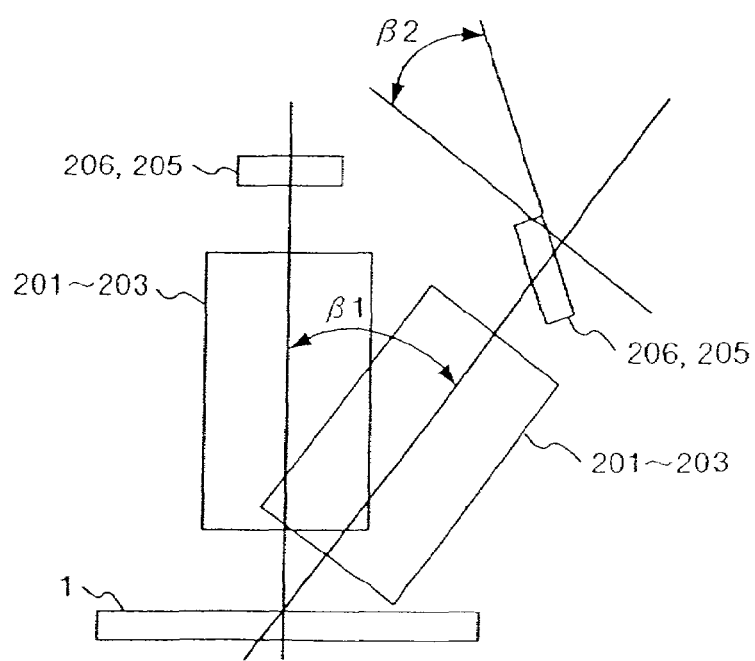
FIG. 17 is a diagram showing an embodiment wherein an optical axis of a detection optical system is inclined at a gradient and photo sensitive surface of a TDI image sensor is inclined at a slope adjusted to the gradient.

If TDI (Time Delay Integration) sensors are used as the detectors 205 and 206, however, the optical axis of the detection optical system 200 can not be inclined due to a focal depth. Thus, in the case of the second embodiment, one-dimensional sensors are employed. As an alternative, the magnification of a set comprising the detection lens 201, the spatial filter 202 and the image formation lens 203 employed in the detection optical system 200 is doubled or increased by several times and, as shown in FIG. 17, the TDI image sensors 205 and 206 are inclined at a gradient β2 expressed by Eq. (4) below. In this way, the magnification can be adjusted for the entire surface.

$$\tan \beta_2 = M \times \tan \beta_1 \quad (4)$$

where the symbol M denotes the magnification of the set comprising the detection lens 201, the spatial filter 202 and the image formation lens 203.

It should be noted that, if one-dimensional sensors are employed, the inclination at the gradient $\beta_2$ is not required.

Figure 18:
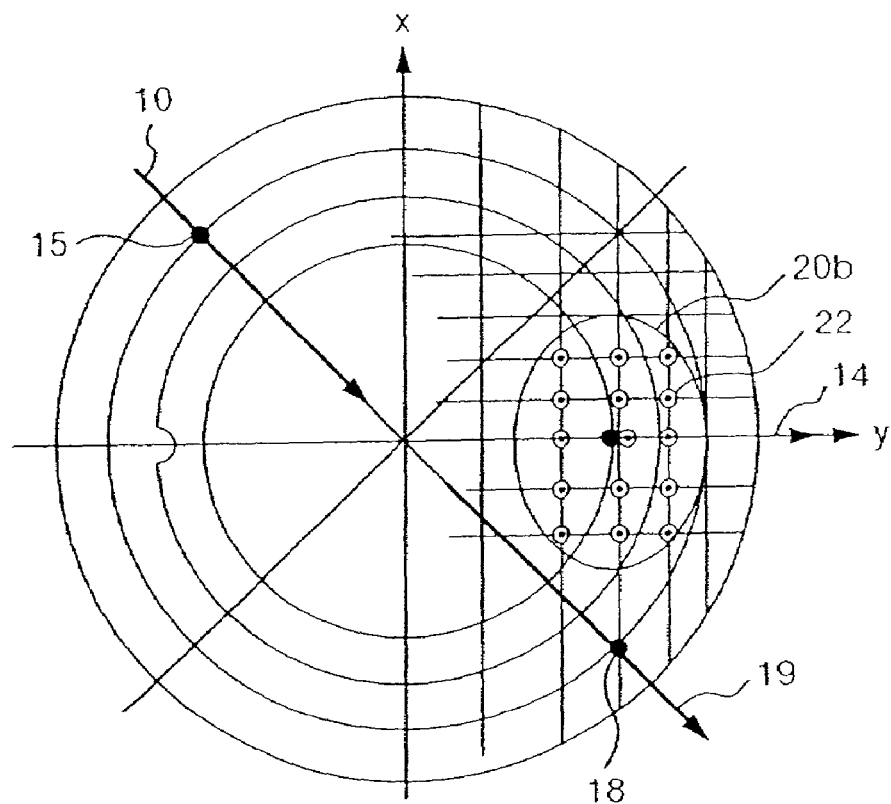
FIG. 18 is a diagram showing a state of projection of a diffraction light beam which is generated by a repetitive pattern when a slit-shaped beam is radiated in a direction forming an angle of 45 degrees with a group of main straight lines of a circuit pattern according to the present invention.

The next description explains detection of scattered lights generated by a defect such as a foreign particle using the one-dimensional detectors 205 and 206 each implemented typically by a TDI image sensor by elimination of diffraction lights generated by a non-repetitive pattern and a repetitive pattern in the second embodiment. Also in the case of the second embodiment, slit-shaped beams 3 are radiated to the substrate (or wafer) 1 being inspected in the same way as that shown in FIG. 5. When a slit-shaped beam 3 is radiated from the direction 10 as shown in FIG. 11(a), the state of emission of a diffraction light generated by the substrate 1 is shown in FIG. 11(b) as is the case with the first embodiment. That is to say, a light resulting from true reflection of the illumination light in the direction 10 travels in the emission direction 19, intersecting the virtual spherical surface 17 at the cross point 18, and the light traveling in the emission direction 19 is referred to as a 0th-order light. The beam 3 traveling in the illumination direction 10 and the reflected 0th-order light traveling in the emission direction 19 form the sides of a longitudinal cross section of an imaginary cone oriented upside down perpendicularly to the plane of the x and y axes with the vertex of the cone coinciding with a point of illumination on the plane. Thus, a locus of the intersection point of the reflected 0th-order light traveling in the emission direction 19 and the imaginary spherical surface 17 form the circumference of the bottom of the cone as shown in FIG. 18. Accordingly, in the case of a repetitive pattern, when seen from the direction of the normal line, the locus of the 0th-order light is a straight line parallel to the x and y axes.

Figure 19A:
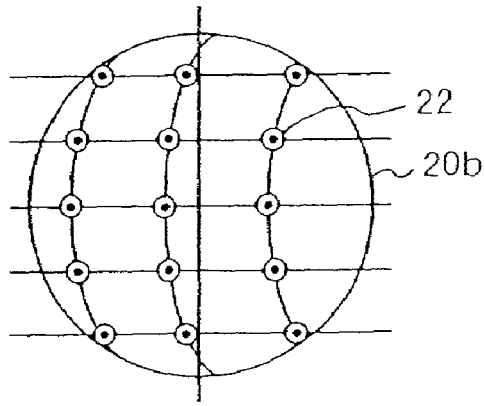
FIG. 19(a) is a diagram showing a top view of diffraction light beams generated by repetitive patterns on a Fourier transformation plane of a detection optical system provided by the present invention.

In particular, in the case of a repetitive pattern, the local maximum of the 0th-order diffraction light is located at an intersection point 22 of the group of straight lines. Thus, the aperture 20b of the objective lens 201 employed in the detection optical system 200 inclined at a gradient $\beta_1$ is like one shown in FIG. 18. When the aperture 20b is seen from a direction 14, that is, the direction of the optical axis, the 0th-order diffraction light 22 appears to be emitted to an intersection point of a curve and a straight line shown in FIG. 19(a).

Figure 19B:
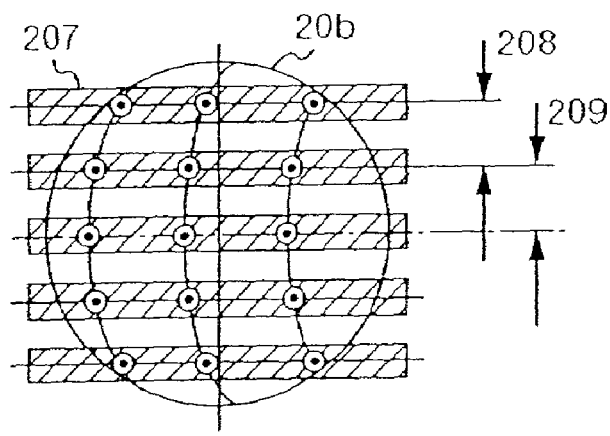
FIG. 19(b) is a diagram showing a relation between the positions of diffraction light beams and a spatial filter.

Then, by shield ing these diffraction lights by means of a shielding portion 207 having a straight-line shape like one shown in FIG. 19(b) in the spatial filter 202, a signal generated by a pattern can be removed. In addition, if the shape and the pitch of a repetitive pattern on the wafer 1 change, the pitch of the locus of the directions of the x and y axes changes, centering at an emission point 18 shown in FIG. 18. Thus, in the aperture 20b, the pitch and the phase of the diffraction light 22 change. In order to shield these diffraction lights, it is necessary to change the pitch and the phase of the straight-line-shaped shielding portion 207.

As described above, a diffraction light generated by a repetitive pattern can be shielded by the spatial filter 202.

Figure 20:
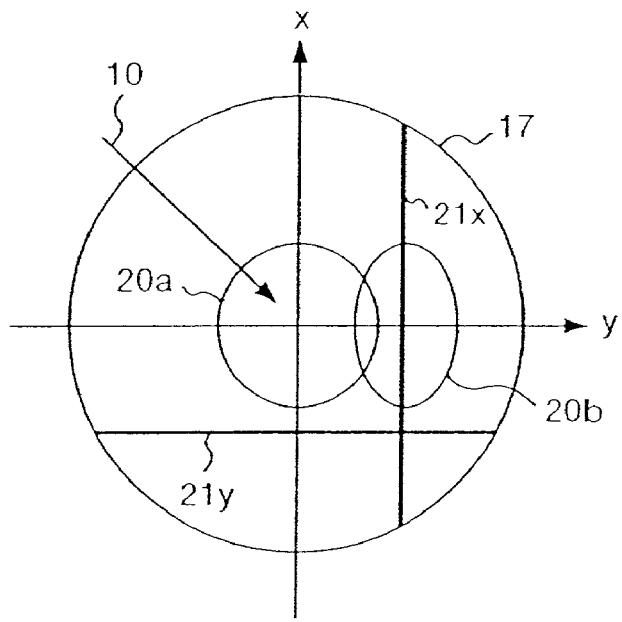
FIG. 20 is a diagram showing relations between: a state of generation of a 0th-order diffraction-light pattern by radiation of a slit-shaped beam in a direction forming an angle of 45 degrees with a group of main straight lines of a circuit pattern according to the present invention; and an aperture of an objective lens of a detection optical system with an optical axis thereof oriented in a vertical direction and the direction of the y axis.

The next description explains elimination of diffraction lights generated by a non-repetitive pattern. In general, a non-repetitive pattern is a straight-line pattern oriented in the directions of the x and y axes. Thus, when a slit-shaped beam 3 is radiated from the direction 10, 0th-order diffraction lights 21x and 21y in the directions of the x and y axes respectively shown in FIG. 20 are generated as is the case shown in FIG. 12. Since the optical axis 200 of the detection optical system 200 is inclined at the gradient $\beta_1$, however, the intensity of a light scattered by an infinitesimal particle is high but the 0th-order diffraction light 21x emitted in the direction of the y axis enters the aperture 20b of the objective lens 201. Thus, also in the case of a non repetitive pattern, it becomes necessary to shield the 0th-order diffraction light 21x by using the spatial filter 202.

Since a diffraction light beam generated by a repetitive pattern is different from a 0th-order diffraction light pattern for a non-repetitive pattern as described above, it is necessary to provide both the diffraction-light patterns to the spatial filter 202. If an attempt is made to shield both the diffraction-light patterns by using the spatial filter 202, however, the intensity of a scattered light passing through the spatial filter 202 is attenuated, causing the sensitivity to deteriorate.

In order to solve the problem described above, the optical axis of the detection optical system 200 is erected to position the aperture of the objective lens 201 at a location 20a and to radiate slit-shaped beams 3 to a non-repetitive pattern from the directions 10 and 12 as is the case with the first embodiment. In this way, 0th-order light patterns 21x and 21y can be prevented from entering the aperture 20a of the objective lens 201, making it possible to detect a defect such as a foreign particle existing on a non-repetitive pattern.

As is obvious from the description of the first embodiment given earlier, however, it is necessary to radiate a slit-shaped beam 3 from the direction of the y axis 11 as shown in FIG. 13 in an attempt to detect a defect such as a foreign particle existing in a dent between wires. In this case, however, a 0th-order diffraction light 21y' enters the aperture 20a of the objective lens 201 as shown in FIG. 13, making it necessary to shield the light 21y' by means of the spatial filter 202. Nevertheless, the detection of a defect such as a foreign particle existing in a dent between wires is not the principal part of the detection of defect in general including foreign particles. Since a pattern being inspected is identified, a measure can be taken during the image processing.

If the conditions described above are configured in a way described below, the conditions can be satisfied. To put it in detail, the illuminations from the directions 10 and 12 each forming an angle of 45 degrees with the y axis are given up and only a slit-shaped beam 3 is radiated from the direction of the y axis 11. The optical axis of the detection optical system 200 is inclined from the vertical direction toward the directions of the x and y axes to place the aperture of the objective lens 201 at a position denoted by reference numeral 20c in FIG. 21. In this way, 0th-order light patterns 21x' and 21y' can be prevented from entering the aperture 20c of the objective lens 201. In this configuration, the spatial filter 202 can be designed to shield only a diffraction light beam generated by a repetitive pattern. In addition, it is possible to prevent deterioration of the intensity of a scattered light passing through the spatial filter 202 from a defect such as a foreign particle.

In this case, however, it is necessary to decrease the N.A. of the objective lens 201.

The problem is the focuses of the detectors 205 and 206. As shown in FIG. 17, the configuration with the inclined detectors 205 and 206 allows the focuses to be adjusted in the entire image formation area. In this case, it will be insufficient to merely incline the detectors 205 and 206 at a gradient $\beta_2$. Instead, it is necessary to incline them at the gradient β2 and in a direction perpendicular to the direction 14. In addition, since the detection optical system 200 employs a telecentric optical system, the horizontal magnification by no means changes at a portion where the focal positions are different from each other.

Next, the following description explains a third embodiment implementing a defect inspection apparatus provided by the present invention for detecting a defect such as a foreign particle. The third embodiment is inferior to the first and second embodiments.

Figure 22:
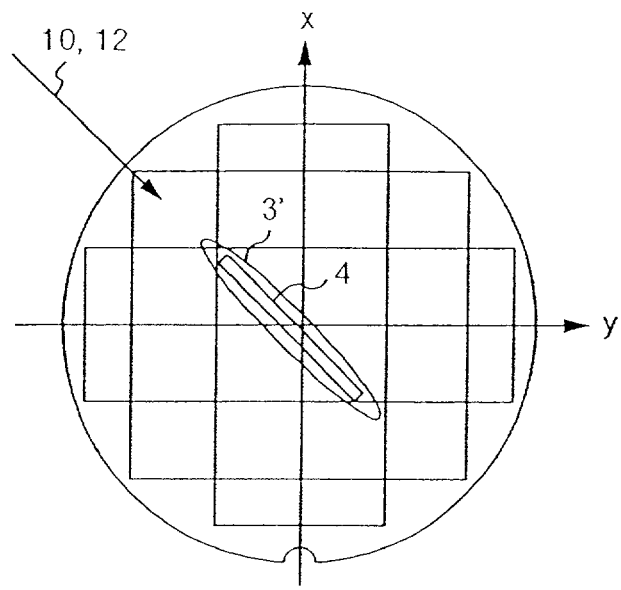
FIG. 22 is a diagram showing an embodiment of the present invention wherein a slit-shaped beam with its longitudinal direction oriented in the direction of radiation is radiated to a substrate in a direction forming an angle of 45 degrees with a group of main straight lines of a circuit pattern on the substrate according to the present invention.

In the case of the third embodiment, a cylindrical lens 104' is employed in place of the conical lens 104 as shown in FIG. 22. By using the cylindrical lens 104', slit-shaped beams 3' with the longitudinal directions thereof oriented to the illumination directions 10 and 12 are radiated to the surface of the wafer 1. The illumination directions 10 and 12 are inclined from the layout direction of chips created on the wafer 1 by an angle of about 45 degrees. The slit shapes of the beams are parallel to the incidence plane of the illumination. As a matter of course, since the slit-shaped beams 3' are beams parallel to each other in their longitudinal direction, they do not intercept each other in the transversal direction. It should be noted that diffraction lights generated by repetitive and non-repetitive patterns created on chips 2 on the wafer 1 are handled in the same way as the first and second embodiments.

In the case of the third embodiment, it is necessary to set the y-axis scanning direction of the stage in an orientation perpendicular or parallel to the chips in order to make chip comparison simple. In addition, since the integration direction of the TDI image sensors is not parallel to the y-axis scanning direction of the stage in the third embodiment, TDI image sensors can not be used as the detectors 205 and 206. It is thus necessary to employ one-dimensional linear sensors as the detectors 205 and 206. In the case of a linear sensor, since an optical signal from an area narrower than the width of the illumination beam is detected, it is desired to squeeze the illumination beam 3' to a width close to the image 4 of the sensor in order to utilize the illumination beam 3' with a high degree of efficiency. To put it concretely, assume that the pixel size of the sensor is 13 μm and the magnification of the optical system is 6.5 times. In this case, the pixel size of the image of the sensor formed on the wafer 1 is 2 μm. Let the wavelength of the used laser be 532 nm. In this case, it is desirable to set the N.A. (numerical aperture) of the lens 104' employed in a direction perpendicular to the longitudinal direction of the sensor at about 0.5 in Eq. (5) given below. Of course, this value is selected only in order to increase the efficiency of the illumination. If it is not necessary to increase the efficiency of the illumination, a smaller N.A. can be used.

$$d=1.22\times \lambda/N.A. \quad (5)$$

where the symbol d denotes the half band width and the symbol λ denotes the wavelength of the illumination beam.

Figure 23:
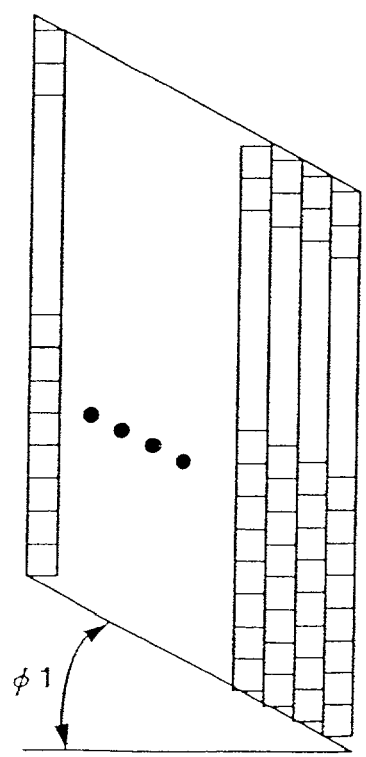
FIG. 23 is a diagram showing a special TDI image sensor which is required when the slit-shaped beam shown in FIG. 22 is radiated.

When TDI image sensors are used as the detectors 205 and 206 in the method of illumination shown in FIG. 22, the sensors must be special, having a shape like one shown in FIG. 23. That is to say, the special TDI image sensors have a pixel configuration with an integration direction inclined at a gradient φ1.

The following description explains detection of a defect such as a foreign particle existing on an insulation film such as an oxide film with no pattern used as an object of inspection.

Figure 24:
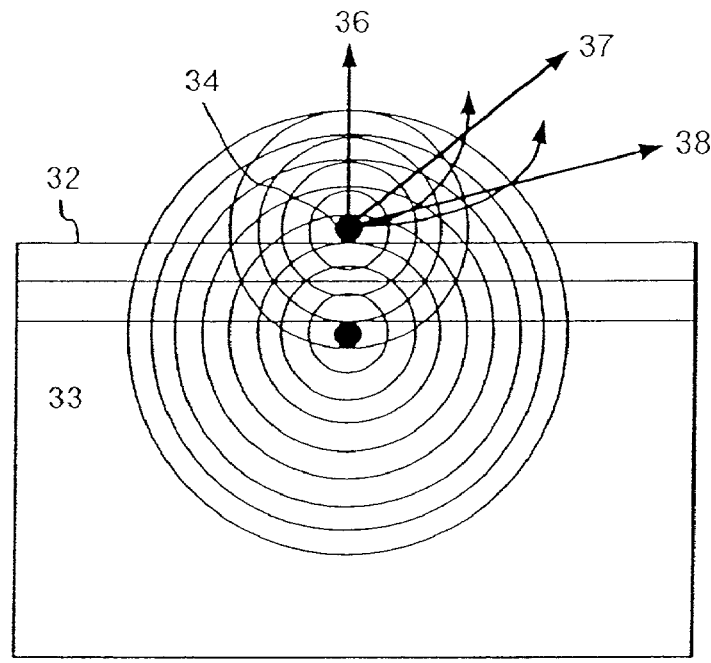
FIG. 24 is a diagram showing a side view of an interference model of lights scattered by a foreign particle existing on an insulation film such as an oxide film being inspected in accordance with the present invention.

FIG. 24 is a diagram showing a state of scattering of lights by a transparent film such as an oxide film. Assume that a very small infinitesimal particle or a foreign particle 34 with a size equal to a fraction of the wavelength of the illumination beam exists on the surface of an oxide film 32 on a substrate 33. In this case, the particle generates a beam having a spherical polarization plane. That is to say, a beam is radiated to the surface of the oxide film 32 and to the detectors at the same time. The beam emitted by a particle with such a polarization plane is a result of reflection of the beam radiated to the oxide film 32 by a boundary surface between the oxide film 32 and an underlying layer 33. The reflected beam interferes the beam radiated directly to the defector, resulting in strength in the emission direction. As a result, outputs of the detection in directions 36, 37 and 38 are different from each other. The intensity distribution changes in dependence on the thickness of the oxide film and the refractive index. As a result, the intensity of a detection beam detected from the same direction changes, causing the sensitivity to also vary as well.

According to consideration based on this model, however, the output of a detected light remains unchanged without regard to the direction of the illumination. In addition, experiments have proven that the output of a detected beam does not change even if the angle of incidence of the illumination light is changed.

However, optical interference can be eliminated by radiation of a white light. As a matter of fact, the first and second embodiments are provided with a white-illumination optical system 500 for detecting a foreign particle on the insulation film 32 such as an oxide film. Thus, in order to detect a foreign particle on the insulation film 32, the white-color light source 106 is turned on while the laser-beam source 101 is turned off. In addition, white-color illumination is also adopted for an object of inspection affected by the wavelength of the illumination light.

In the case of white-color illumination, the resulting illumination spot is bigger in size than the visual field of the TDI image sensors.

In addition, when the laser-beam source 101 is used for generating an illumination light, it is necessary to employ an objective lens 201 with a large numerical aperture in order to stabilize the detection output on the oxide film 32. This is because such an objective lens 201 is capable of detecting most lights emitted from the surface of the wafer 1. If an objective lens 201 with a small numerical aperture is used, on the other hand, a plurality of such lenses 201 are required. In this case, detection outputs of the lenses 201 are integrated. As an alternative, a plurality illumination lights with different wavelengths are used and their results of detection are integrated.

In this case, absorption or attenuation of a scattered light generated by a foreign particle on the film can be assumed to be substantially non-existent. In the case of a non-existing foreign particle, lights are emitted in one direction so that, the output in this direction varies due to interference. If a foreign particle exists, on the other hand, the emitted light is spread in a plurality of emission directions since interference occurs in the form of intensity distribution among the emission directions.

Figure 25:
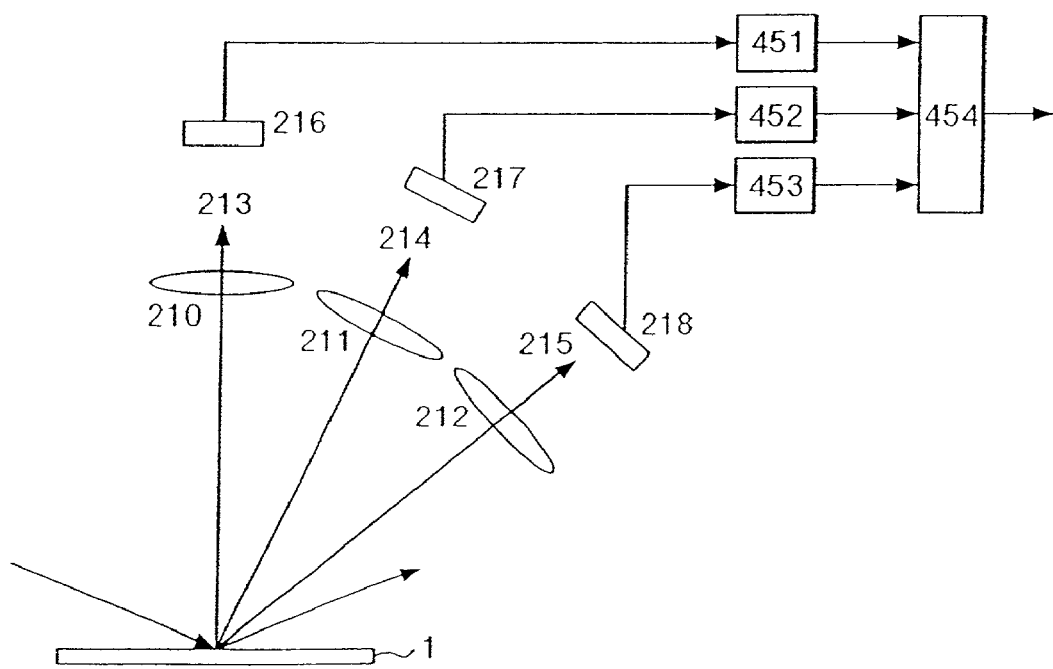
FIG. 25 is an explanatory diagram used for describing an embodiment for detecting lights scattered by a foreign particle existing on an insulation film such as an oxide film in a plurality of detection directions in order to detect the foreign particle.

FIG. 25 is a diagram showing the configuration of an embodiment for detection from a plurality of directions. From lights emitted in directions 213, 214 and 215, detection lenses 210, 211 and 212 form images which are detected by detectors 213, 214 and 215 respectively. Analog electrical signals obtained as results of photo-electrical conversions carried out by the detectors 213, 214 and 215 are converted into digital data by A/D converters 451, 452 and 453 respectively. The digital data is then integrated by an integration means 454 and converted into binary data representing a result of detection by using a proper threshold value.

It should be noted that the number of detection systems including the detection lenses 210, 211 and 212 does not have to be 3. For example, 2 detection systems gare OK. In addition, the detection systems in this embodiment are each implemented by the detection optical system 200 shown in FIG. 3. In this case, each of the detection optical systems 200 is inclined by a gradient β. Examples of the gradient are β1=0 degrees and β1=45 degrees.

Figure 26A:
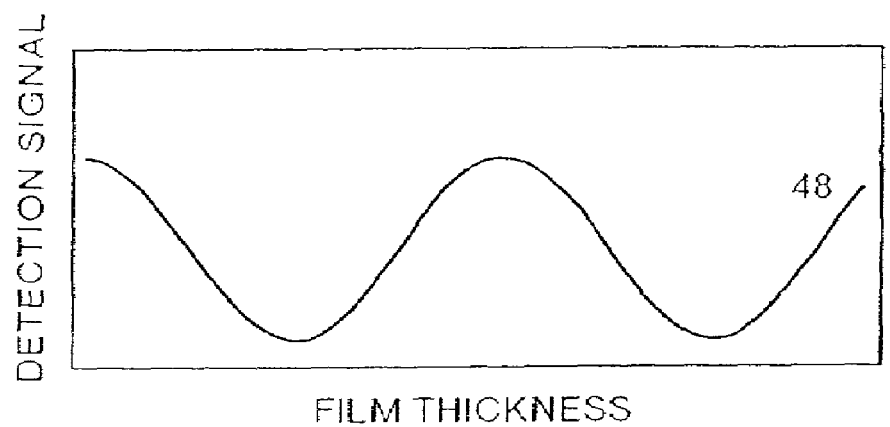
FIG. 26(a) is a diagram showing a relation between the thickness change of an insulation film such as an oxide film and a detection signal for an illumination light having a certain wavelength.
Figure 26B:
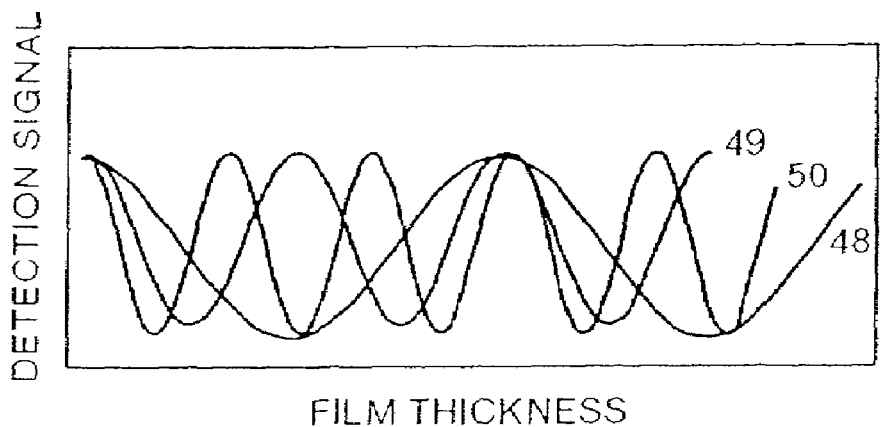
FIG. 26(b) is a diagram showing a relation between the thickness change of an insulation film such as an oxide film and a detection signal for illumination lights having 3 different wavelengths.

FIG. 26 is diagrams showing changes in detection signal with variations in oxide-film thickness. To be more specific, FIG. 26(*a*) is a diagram showing an intensity-variation change 48 of a light with a certain wavelength. On the other hand, FIG. 26(*b*) is a diagram showing intensity-variation curves 48, 49 and 50 of 3 lights with different wavelengths. By integrating results of detection for the lights with different wavelengths shown in FIG. 26(*b*), variations in integration result will be smaller than variations in intensity shown in FIG. 26(*a*) as is obvious from the figures.

In this case, since we know that the intensity of a detected signal is not dependent on the angle of incidence of the illumination light, lights with different wavelengths can be radiated at different angles of incidence or from different directions determined by the angle φ. That is to say, by setting the wavelengths of the slit-shaped beams 3 radiated from the directions 10, 11 and 12 at values different from each other, it is possible to detect a signal indicating a foreign particle on an insulation film such as an oxide film by means of a single detection optical system 200. The reason why it is possible to detect a signal indicating a foreign particle on an insulation film such as an oxide film by means of a single detection optical system 200 by setting the wavelengths of the slit-shaped beams 3 radiated from the directions 10, 11 and 12 at values different from each other is that there is no mutual interference. As a result, it is possible to avoid an increase in cost caused by a need to prepare a plurality of detection optical systems 200. With at least 2 beams having different wavelengths, the detection optical system 200 is capable of correcting color aberration (and a focal distance) with ease. As a result, there is no difficulty in the implementation as long as 2 beams having different wavelengths are used.

The next description explains a fourth embodiment implementing a defect inspecting apparatus provided by the present invention for detecting a defect such as a foreign particle. By the way, with semiconductor devices miniaturized more and more, a further increase in yield is also required. To put it in detail, a circuit pattern created on a semiconductor substrate such as a semiconductor wafer for making such semiconductor devices is subjected to super miniaturization with a design rule of 0.3 to 0.2 µm or even smaller. For this reason, a foreign particle existing on the semiconductor substrate causes a semiconductor device created on the substrate to operate abnormally even if the foreign particle is an infinitesimal molecule with a size of about 0.1 µm or smaller or a particle with a size close to that at an atomic level.

In such a state of the art to fabricate a semiconductor device, the defect inspecting apparatus provided by the present invention for detecting a defect such as a foreign particle is required to have a capability of inspecting a defect such as an infinitesimal foreign particle existing on a semiconductor substrate such as a semiconductor wafer, on which a circuit pattern undergoing a super-miniaturization by a design rule of 0.3 to 0.2 µm or even smaller exists, with a high degree of sensitivity at a high speed.

Figure 35:
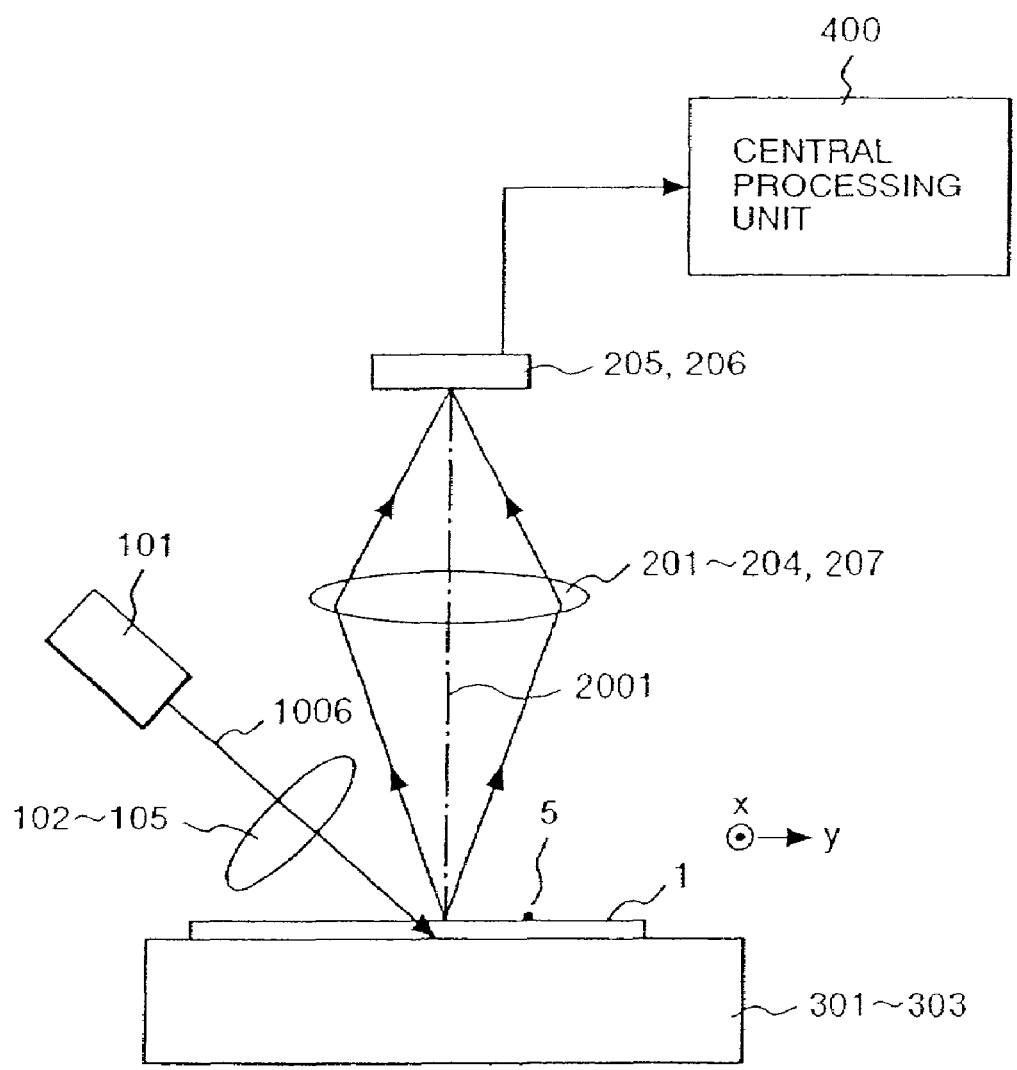
FIG. 35 is a diagram showing the configuration of a fourth embodiment implementing a defect inspecting apparatus provided by the present invention in a simple and plain manner.
Figure 36A:
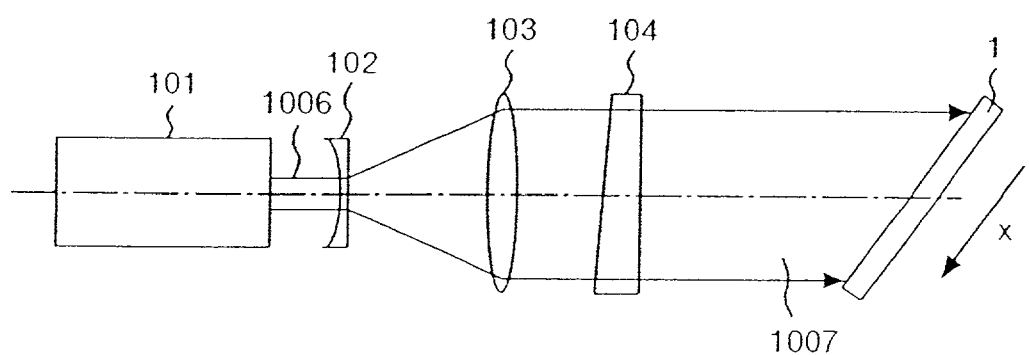
FIG. 36(a) is a diagram showing an embodiment implementing an illumination optical system employed in the fourth embodiment implementing a defect inspecting apparatus of FIG. 35 in concrete terms as seen from a position on the y axis.
Figure 36B:
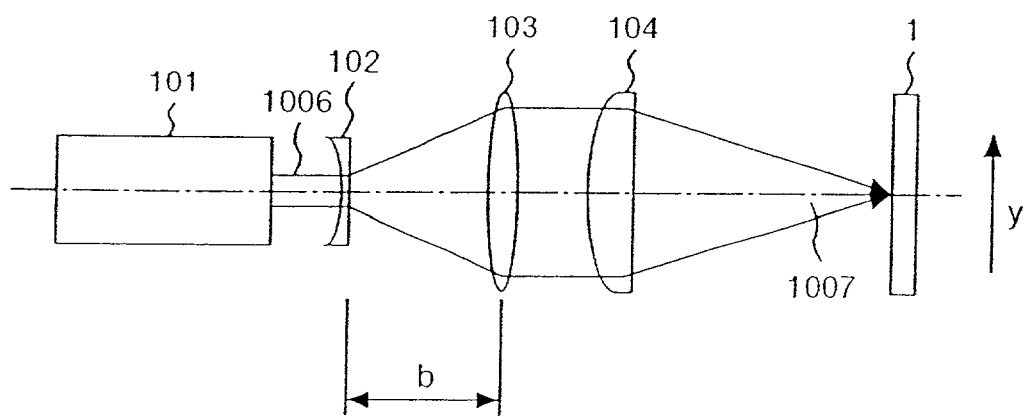
FIG. 36(b) is a diagram showing the same in concrete terms as seen from a position on the x axis.

FIG. 35 is a diagram showing the fourth embodiment implementing a defect inspecting apparatus provided by the present invention for detecting a defect such as a foreign particle in a simple and plain manner. FIG. 36 is a diagram showing an embodiment implementing an illumination optical system employed in the defect inspecting apparatus.

Figure 37:
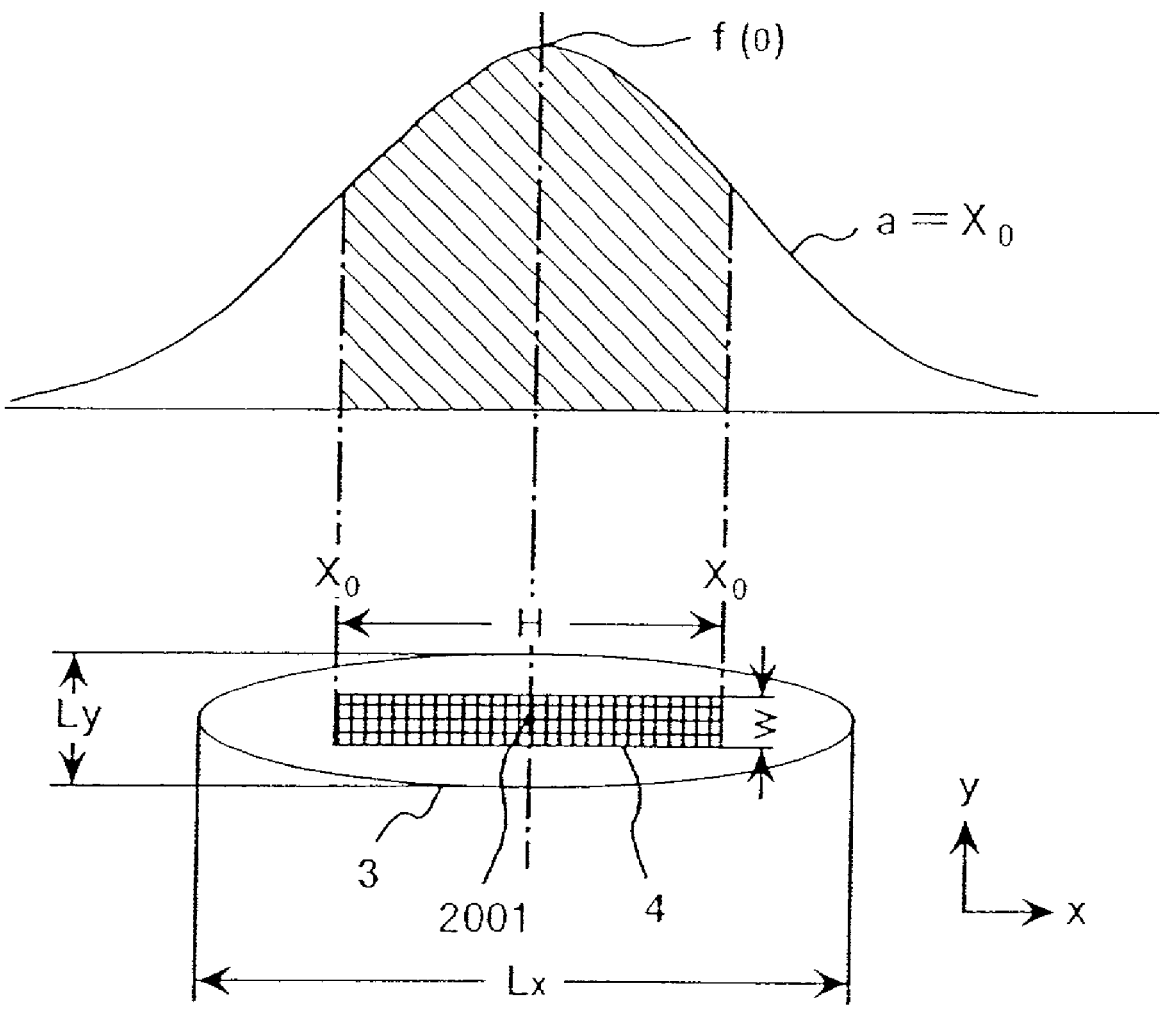
FIG. 37 is an explanatory diagram used for describing a basic concept of shaping a slit-shaped Gaussian beam by means of an illumination optical system to increase the illumination efficiency.

As shown in FIG. 35, the defect inspecting apparatus for detecting a defect such as a foreign particle comprises: stages 301, 302 and 303 for mounting an inspection object 1 such as a semiconductor device or a semiconductor wafer on which a super-miniaturized circuit pattern with a defect thereof to be detected has been created; an illumination-light source 101 implemented by a laser-beam source such as a semiconductor laser, an argon laser, a YAG-SHG laser or an exima laser; an illumination optical system comprising the components 102 to 105 for radiating a high-luminance light emitted by the illumination-light source (laser source) 101 to an illumination area 3 on the inspection object 1 from a slanting direction as a slit-shaped Gaussian beam 107 having a illumination distribution close to the Gaussian distribution as shown in FIG. 37; a detection optical system 200 including a detection lens (objective lens) 201, a spatial filter 202, an image formation lens 203, an ND filter 207 and a beam splitter 204 which are used for forming an image from diffraction lights (or scattered lights) reflected by a detection area 4 to pass through the detection optical system 200; detectors 205 and 206 each implemented typically by a TDI image sensor or a CCD image sensor having a photo-sensitive surface corresponding to the detection area 4; and an image-signal processing unit 400 for detecting a defect such as a foreign particle from an image signal output by the detectors 205 and 206.

It should be noted that the defect inspecting apparatus also has an automatic focus control system for controlling formation of an image of the surface of the inspection object 1 on the photo-sensitive surface of the detectors 205 and 206.

The actual configuration of the illumination-light optical source 101 and the illumination optical systems comprising the components 102 to 105 is shown in FIG. 36. In the figure, reference numeral 102 denotes a concave or convex lens for enlarging the diameter of a laser beam 1006 emitted by the illumination-light source 101. Reference numeral 103 denotes a collimate lens for converting a laser beam output by the concave or convex lens 102 with an expanding diameter into substantially parallel beams. Reference numeral 104 denotes an illumination lens with a conical surface for converging the substantially parallel beams obtained as a result of the conversion in the collimate lens 103 in the direction of the y axis and for radiating the converged beams to an illumination area 3 on the inspection object 1 as a slit-shaped Gaussian beam 1007 having an illumination distribution close to the Gaussian distribution as shown in FIG. 37. The illumination lens 104 serves as an optical system having a converging function in the direction of the y axis.

It should be noted that the concave or convex lens 102 and the collimate lens 103 constitute a beam expander for enlarging the diameter of the laser beam 1006. Thus, the illumination optical system including the components 102 to 104 can be regarded as a system comprising the beam expander, the conical lens 104 and a mirror. The beam expander typically comprises a collimate lens, a concave lens and a receiver lens. As described above, the conical lens 104 is used for converging the substantially parallel beams obtained as a result of the conversion in the beam expander in the direction of the y axis and for radiating the converged beams to an illumination area 3 on the inspection object 1 as a slit-shaped Gaussian beam 1007 having an illumination distribution close to the Gaussian distribution as shown in FIG. 36. The mirror reflects the slit-shaped Gaussian beam 1007 output by the conical lens 104 and radiates the beam 1007 to the inspection object 1 in a slanting direction.

By the way, by changing the distance b between the concave or convex lens 102 and the collimate lens 103 or the distance between the concave lens and the receiver lens in the configuration described above, the x-direction width of the luminance beam having an illumination distribution substantially resembling the Gaussian distribution can be altered. That is to say, by adjusting the beam expander, the x-direction length Lx of the illumination area 3 (or the slit-shaped beam 1007) having an illumination distribution substantially resembling the Gaussian distribution can be changed. In addition, by varying the distance between the conical lens 104 and the inspection object 1, the y-direction length Ly of the illumination area 3 (or the slit-shaped beam 1007) having an illumination distribution substantially resembling the Gaussian distribution can also be changed.

Figure 38A:
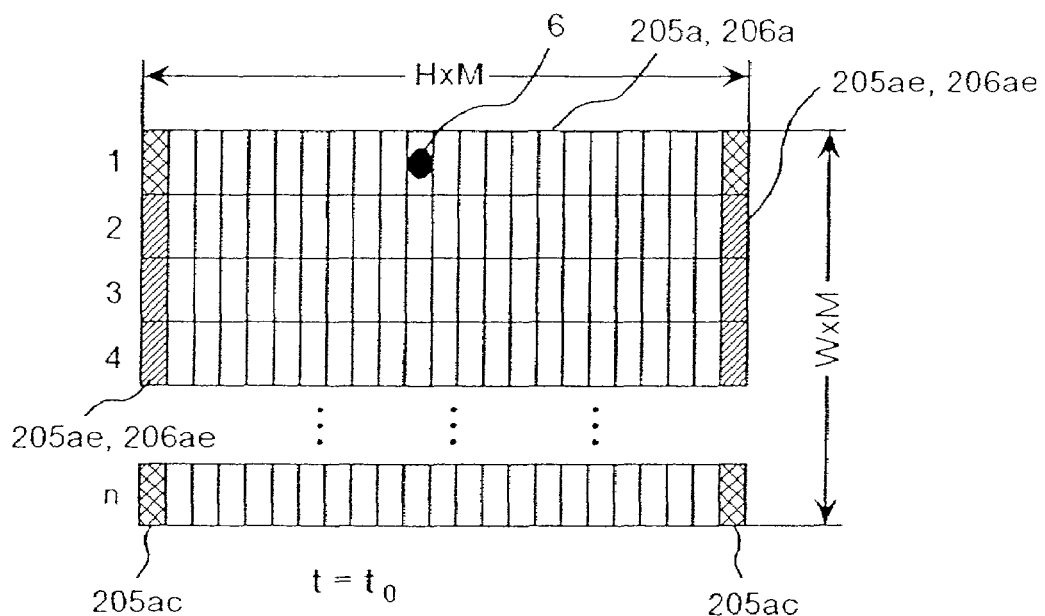
FIGS. 38(a) and 38(b) are explanatory diagrams used for describing an image-pickup method to receive a light representing an optical image in an area of detection on a substrate being inspected by using a TDI image sensor as a detector.
Figure 38B:
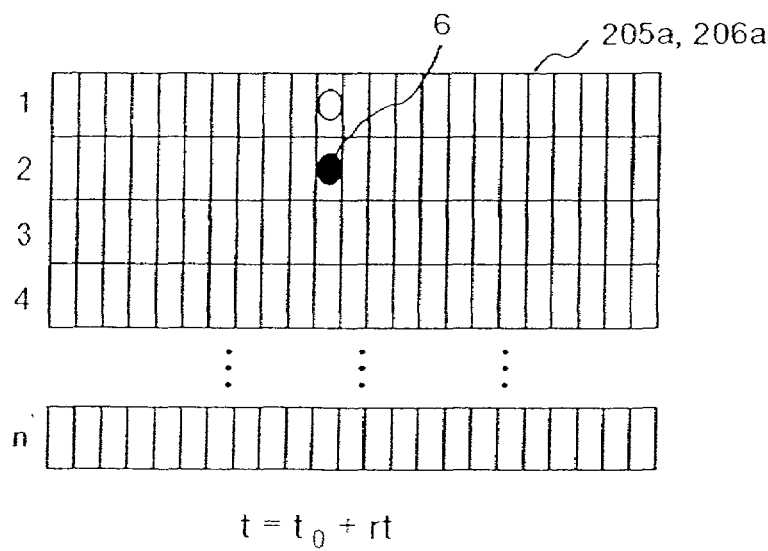

A detection area 4 shown in FIG. 37 is an area on the inspection object 1 to be inspected by using a TDI image sensor or a CCD image sensor. In the case of a TDI image sensor, for example, the dimensions of each pixel are typically 27 µm×27 µm. The TDI image sensor is typically a 64×4,096 CCD image-pickup sensor which comprises 64 rows in the TDI (Time Delay Integration) direction and 4,096 columns in the MUX direction, and operates in a TDI mode. That is to say, the TDI image sensors 205a and 206a have a configuration comprising n stages of line sensors as shown in FIG. 38 where n is typically 64. A line rate rt is the amount of information output by the sensor which is the line sensors in this case. At a line rate rt, accumulated charge is transferred through lines 1, 2 and so on, from one line to another. By synchronizing the movement speed of the y-axis stage 302 for moving the inspection object 1 in the direction of the y axis with the line rate rt, an image 6 based on a scattered light and a diffraction light generated by typically an infinitesimal foreign particle 5 is accumulated for a long time it takes to transfer the charge to the line n so that a defect such as an infinitesimal foreign particle can be detected with a high degree of sensitivity. In this image sensor, the image of a defect such as an infinitesimal foreign particle is detected as a sum of intensities of a scattered light and a diffraction light traveling from the line 1 to the line n. However, a scattered light or a diffraction light coming from the same point on the object of inspection and reaching the lines is timewise entirely incoherent.

As described above, a beam emitted by the illumination-light source 101 is converted by the illumination optical system (or the radiation optical system) comprising the components 102 to 104 into a slit-shaped Gaussian beam 1007 which is radiated to the surface of the inspected substrate 1 on the stages 301 to 303 typically in a slanting direction to form an illumination area 3 on the surface. While the inspected substrate 1 is being moved in the direction of the y axis by moving the y-axis stage 302 in the direction of the y axis, the detectors 205a and 206a each implemented typically by a TDI image sensor transfers electric charge accumulated in each pixel from one line to another at a line rate rt synchronized with the movement speed of the y-axis stage 302. In this way, while an optical image of the detection area 4 on the inspected substrate 1 formed by the detection optical system comprising the components 201 to 204 is being picked up, each pixel (or each device) along the width H of the detection area 4 is scanned to generate a detection signal which is then supplied to the image-signal processing unit 400. By processing the detection signal in the image-signal processing unit 400, it is possible to detect a defect such as an infinitesimal foreign particle existing in the detection area 4 with a high degree of sensitivity and at a high speed.

By using the TDI image sensors 205a and 206a as described above, it is possible to compute a total of illumination values of a scattered light or a diffraction light generated by a defect such as an infinitesimal foreign particle where (quantity of light=illumination value×time) and, hence, to increase the sensitivity. In addition, once the slit-shaped beam 1007 is radiated to the radiation area 3 and, a light generated by the detection area 4 is received by the TDI image sensors 205a and 206a while the inspected substrate 1 is being moved in the direction of the y axis in synchronization with the line rate rt of the TDI image sensors so that it is possible to detect a defect such as an infinitesimal foreign particle existing in the detection area 4 with a large width H at a high speed.

The following description further describes the fourth embodiment of the present invention for detecting a defect such as an infinitesimal foreign particle with a size of about 0.1 µm or smaller with a high degree of sensitivity and at a high speed. That is to say, when it is desired to detect a defect such as an infinitesimal foreign particle with a size of about 0.1 µm or smaller with a high degree of sensitivity, it is necessary to increase the intensity of a scattered light or a diffraction light generated by a defect such as an infinitesimal foreign particle and received by pixels of a TDI image sensor 302a and also to reduce the dimensions of each pixel on the inspected substrate 1 to about 1 µm×1 µm or smaller.

It is possible to realize an implementation wherein the dimensions of each pixel on the inspected substrate 1 are reduced to about 1 µm×1 µm or smaller as described above by setting the image formation magnification M of the detection optical system comprising the components 201 to 204 including an objective lens at a value of about 27 times or larger for dimensions of each pixel on the TDI image sensors of typically 27 µm×27 µm. It should be noted that, if 26×4,096 CCD pickup sensors are used as the TDI image sensors 205a and 206a, the detection area 4 will have a width W not exceeding a value of about 26 µm and a height H not exceeding a value of about 4,096 µm.

In addition, the detection optical system comprising the components 201 to 204 for forming an image in photo-sensitive areas on the TDI image sensors 205a and 206a from an optical image formed by a scattered light or a diffraction light generated by the surface of the inspected substrate 1 includes an objective lens having a characteristic which, due to lens aberration, shows the fact that, the farther a position from the center of the lens (or the optical axis 2001), that is, the closer a position to a periphery, the smaller the MTF (Modulation Transfer Function) at the position. The MTF represents changes in contrast of an image of a sinusoidal wave pattern as a function of spatial frequency. For this reason, it is necessary to increase the intensity of a scattered light or a diffraction light generated by pixels 205ae and 206ae on the edge (or the periphery) with a smallest MTF located farthest from the optical axis 2001 on the photo-sensitive surface of the TDI image sensors 205a and 206a shown in FIG. 38(a), or generated by a defect such as an infinitesimal foreign particle located on the edge (or the periphery) with a smallest MTF farthest from the optical axis 2001 in the detection area 4 shown in FIG. 37.

By the way, the illumination of the slit-shaped Gaussian beam 1007 radiated to the radiation area 3 on the surface of the inspected substrate 1 by the illumination-light source 101 and the illumination optical system comprising the components 102 to 104 exhibits the ordinary Gaussian distribution as shown in FIG. 37, wasting illumination outside the detection area 4. On the other hand, it is necessary to illuminate the illumination area 3 which is made larger than the detection area 4.

In order to solve this problem, in this present invention, the quantity of a light emitted by the illumination-light source 101 is utilized effectively and the illumination on the edge (or the periphery) with a smallest MTF farthest from the optical axis 2001 in the detection area 4 is increased most without increasing the illumination of the light in order to detect a defect such as an infinitesimal foreign particle with a size of about 0.1 µm or smaller with a high degree of sensitivity. That is to say, by employing a low-cost illumination-light source 101 for emitting a light with a minimum required illumination, the illumination on the edge (or the periphery) with a smallest MTF farthest from the optical axis 2001 in the detection area 4 can be increased most by the illumination optical system comprising the components 102 to 104 to implement illumination with a high degree of efficiency. Examples of such a low-cost illumination-light source 101 are a laser-beam source such as a semiconductor laser, an argon laser, a YAG-SHG laser or an exima laser and a filament light source such as a canon lamp, an electric-discharge tube such as mercury lamp and a halogen lamp.

To put it concretely, in the present invention, when the illumination-light source 101 and the illumination optical system comprising the components 102 to 104 radiates a slit-shaped beam 1007 having an illumination of the Gaussian distribution to illuminate the illumination area 3 on the inspected substrate 1, the illumination optical system comprising the components 102 to 104 is adjusted (or controlled) to set such a width of the illumination that the illumination on the periphery of the detection area 4 is maximized. The Gaussian distribution of the illumination of the slit-shaped beam 1007 shown in FIG. 37 can be expressed by Eq. (6) given below. The illumination on the periphery of the detection area 4 is maximized when the expression on the right-hand side of Eq. (7) is equal to 0.

$$f(X_0) = \frac{1}{\sqrt{2\pi}\,\sigma} \exp\left(-\frac{1}{2\sigma^2} X_0^2\right) \quad (6)$$

$$\frac{\partial f(X_0)}{\partial \sigma} = \frac{1}{\sqrt{2\pi}} \left(1 - \frac{X_0}{\sigma}\right)\left(1 + \frac{X_0}{\sigma}\right) \exp\left(-\frac{1}{2\sigma^2} X_0^2\right) \quad (7)$$

The maximum illumination f(x0) on the outermost circumference (edge) of the detection area 4 in the direction of the x axis corresponding to the photo-sensitive surfaces of the TDI image sensors 205a and 206a is about 60.7% of the luminance f(0) at the center of the detection area 4. This is because equating the expression on the right-hand side of Eq. (7) to 0 yields x0=σ (for σ=1, x0=1) and substituting σ for x0 in Eq. (6) results in the maximum value f(x0)=0.607f (0). It should be noted that, for x0=0.8σ to 1.2σ in Eq. (6), f(x0)=0.49f(0) to 0.73f(0). In this case, for σ=1, x0=0.8 to 1.2 (for the Gaussian beam 1007, a reshaping error in the range ±20% caused by the illumination optical system comprising the components 102 to 104 is allowable). For σ=0.8×0 to 1.2×0 in Eq. (6) which means that, for x0=1, σ=0.8 to 1.2 (for the Gaussian beam 1007, a reshaping error in the range ±20% caused by the illumination optical system comprising the components 102 to 104 is allowable), f(x0) =0.46f(0) to 0.71f(0). Thus, if a reshaping error of the Gaussian beam 1007 in the range ±20% caused by the illumination optical system comprising the components 102 to 104 is allowable for x0=σ (for σ=1, x0=1), the ratio of the illumination f(x0) on the outermost circumference (the periphery) of the detection area 4 to the illumination f(0) at the center (the optical axis 2001) of the detection area 4 is in the range 0.46 to 0.73, or f(x0)=0.46f(0) to 0.73f(0). It should be noted that, if a reshaping error of the Gaussian beam 1007 in the range ±10% caused by the illumination optical system comprising the components 102 to 104 is allowable for x0=σ (for σ=1, x0=1), the ratio of the illumination f(x0) on the outermost circumference (the periphery) of the detection area 4 to the illumination f(0) at the center (the optical axis 2001) of the detection area 4 is in the range 0.54 to 0.67, or f(x0)=0.54f(0) to 0.67f(0).

In either case, by reshaping a Gaussian beam 1007 by means of the illumination optical system comprising the components 102 to 104 so that the ratio of the illumination f(x0) on the outermost circumference (the periphery) of the detection area 4 to the illumination f(0) at the center (the optical axis 2001) of the detection area 4 is set at a value in the range 0.46 to 0.73, the beam emitted by the illumination-light source 101 can be utilized effectively to increase the illumination on the periphery of the detection area 4 to a value close to a maximum.

Figure 39:
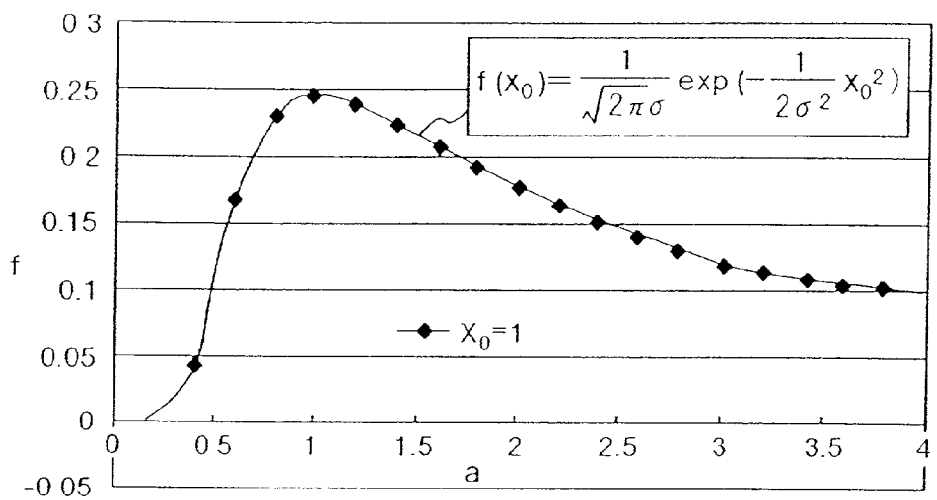
FIG. 39 is a diagram showing variations in illumination $f(x_0)$ at a periphery ($x_0=1$) of a detection area with changes in standard deviation $\sigma$ (corresponding to the width of illumination) of a Gaussian Beam.

FIG. 39 is a diagram showing a graph representing a relation between the width of illumination in the direction of the x axis or the standard deviation σ and the illumination (or the quantity of light per unit area) f(x0=1) on a circumference (x0=1) in the direction of the x axis in the detection area 4 for a fixed quantity of a light or a fixed total illumination of a light emitted by the illumination-light source 101.

Figure 40:
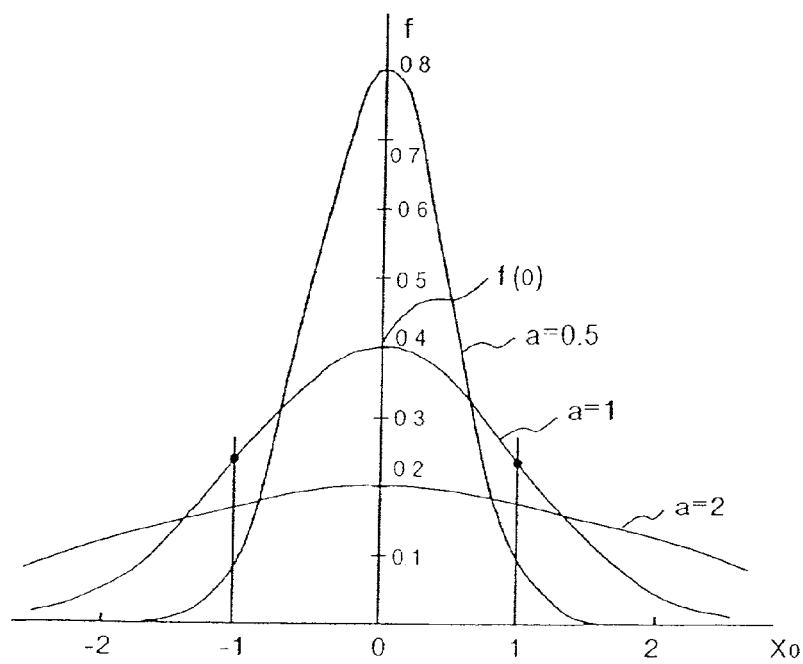
FIG. 40 is a diagram showing variations in illumination $f(x_0)$ with changes in distance $x_0$ from the optical axis of a detection area for a radiated Gaussian beam at standard deviations $\sigma$ of 0.5, 1 and 2.

FIG. 40 is a diagram showing graphs each representing a relation between the coordinate x0 in the direction of the x axis in the detection area 4 and the illumination (or the quantity of light per unit area) f(x0) for a fixed quantity of a light or a fixed total illumination of a light emitted by the illumination-light source 101 with the width of illumination or the standard deviation σ taken as a parameter. The figure shows graphs for parameter values of 0.5, 1 and 2.

As is obvious also from FIGS. 39 and 40, in order to set the illumination on a circumference (x0=1) in the direction of the x axis in the detection area 4 at a value close to a maximum, the beam is radiated with the width σ of the illumination in the direction of the x axis based on the Gaussian distribution generated by the illumination optical system comprising the components 102 to 104 set at a value of about 1 (that is, the standard deviation σ=x0). Let x0 denote the distance from the center of the detection area 4 or the optical axis to the circumference in the direction of the x axis as shown in FIG. 37. In this case, if the illumination optical system comprising the components 102 to 104 reshapes a light emitted by the illumination-light source 101 into a slit-shaped beam 1007 having an illumination of the Gaussian distribution for a standard distribution σ substantially equal to x0 (which is the distance from the center of the detection area 4 or the optical axis to the circumference in the direction of the x axis as described above) and radiates the beam 1007 to the illumination area 3 on the inspected substrate 1, the illumination on a circumference (x0=1) can be maximized. It should be noted that the illumination area 3 is an area with f equal to at least 0.2×f(0) where the symbol f denotes the illumination on the circumference indicated by Lx and Ly.

It should be noted that, in actuality, TDI image sensors or 2-dimensional linear image sensors are used as the detectors 205 and 206. In this case, a pixel with a smallest MTF separated farthest from the optical axis 2001 is located at a corner of the detection area 4. In the case of a TDI image sensor, pixels with a smallest MTF separated farthest from the optical axis 2001 are pixels 205ac and 206ac located at the corners as shown in FIG. 38. Thus, it is desirable to set x0 at the square root of $((H/2)^2+(W/2)^2)$ where the symbols H and W respectively denote the width (the length) in the direction of the x axis and the width in the direction of the y axis of the detection area 4 on the inspected substrate 1. If W can be ignored, x0=(H/2). The width in the direction of the x axis and the width in the direction of the y axis of a photo-sensitive area (an image-pickup area) on the TDI image sensor or the 2-dimensional linear image sensor are thus (H×M) and (W×M) respectively. It should be noted that the symbol M denotes the magnification of the image-formation optical system comprising the components 201 to 204.

As described above, by setting the coordinate x0 of the circumference in the direction of the x axis in the detection area 4 (or in the case of a TDI image sensor or a 2-dimensional linear image sensor, the coordinate x0 of pixels separated farthest from the optical axis 2001) at the square root of $((H/2)^2+(W/2)^2)$ or (H/2) and by having the illumination optical system comprising the components 102 to 104 reshape a light emitted by the illumination-light source 101 into a slit-shaped beam 1007 having an illumination of the Gaussian distribution for a standard distribution σ substantially equal to x0 and radiate the beam 1007 to the illumination area 3 on the inspected substrate 1 where the illumination area 3 is an area with f equal to at least 0.2×f(0) where the symbol f denotes the illumination on the circumference indicated by Lx and Ly, high-efficiency illumination can be implemented by using a low-cost ordinary illumination-light source 101 without the need to employ a special illumination-light source with a high power output. Examples of such a low-cost illumination-light source 101 are a laser-beam source such as a semiconductor laser, an argon laser, a YAG-SHG laser or an exima laser and a filament light source such as a xenon lamp, an electric-discharge tube such as mercury lamp and a halogen lamp. As a result, the detection optical system comprising the components 201 to 204 is capable of increasing the intensity of a scattered light or a diffraction light generated by a defect such as an infinitesimal foreign particle receiving a light radiated to pixels on the peripheries of the detectors 205 and 206 with a lowest MTF. Thus, a defect such as an infinitesimal foreign particle with a size in the range around 0.1 to 0.5 μm or even an infinitesimal foreign particle with a size smaller than about 0.1 μm can be detected with a high degree of sensitivity and at a high speed (or at a high throughput). It should be noted that, even though the illumination in an area in the direction of the x axis varies in dependence on the coordinate x0 as indicated by f(x0)=0.46×f(0) to 0.73×f(0), the inspection object 1 is moved in the direction of the y axis so that the image-signal processing unit 400 compares an image signal with another image signal obtained from the same pixel array in the direction of the x axis in the detection area 4 detected by the detectors 205 and 206 which are each implemented typically by a TDI image sensor. Thus, there is substantially no effect of the difference in illumination between the center and the periphery. Then, the image-signal processing unit 400 extracts a difference in image signal between chips or cells which are repeated in the same circuit pattern on the basis of image signals detected by the detectors 205 and 206 each implemented typically by a TDI image sensor while the inspection object 1 is being moved in the direction of the y axis. By comparing the extracted difference in image signal using a desired criterion, a defect such as a foreign particle can be detected during the inspection.

In this case, the fact that the illumination (or the quantity of light) on the periphery of the detection area 4 is increased to a value close to a maximum is important. In this embodiment, the illumination on the periphery of the detection area 4 is increased to a value close to a maximum by changing the width of the illumination by means of the illumination optical system comprising the components 102 to 104. As an alternative, the illumination on the periphery of the detection area 4 is increased to a value close to a maximum by changing the shape of a secondary light source of the illumination by means of the illumination optical system comprising the components 102 to 104. As another alternative, the illumination on the periphery of the detection area 4 is increased to a value close to a maximum by varying the size at the location of a Fourier transformation for forming the secondary light source.

Figure 41A:
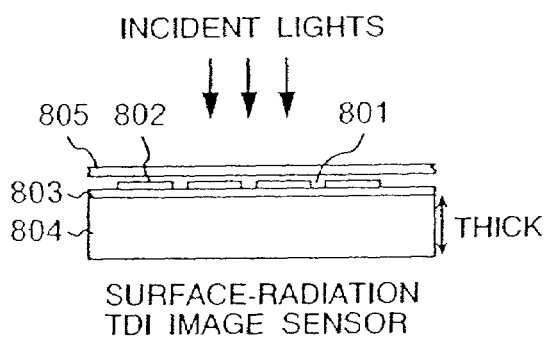
FIGS. 41(a) and 41(b) are explanatory diagrams used for describing an embodiment implementing a TDI image sensor capable of receiving a DUV light.

In addition, since a DUV (deep ultraviolet) laser source is employed as the illumination-light source 101, it is necessary to use image sensors 205 and 206 that are sensitive to a DUV laser. If surface-radiation TDI image sensors shown in FIG. 41(a) are employed as the image sensors 205 and 206, however, an incident light passes through a cover glass 805, gates 801 between metallic films 802 and an oxide film ($SiO_2$ film) 803 before hitting CCDs created on an Si substrate 804. Thus, since an incident light having a small wavelength is attenuated, the sensor becomes substantially insensitive to a light with a wavelength of 400 nm or smaller. As a result, the DUV light may not be detected. In order to make the surface-radiation TDI image sensor sensitive to a DUV light, there is provided a technique whereby the thickness of the oxide film 803 beneath the gates 801 is reduced so that the amount of attenuation of a light with a small wavelength is decreased. As another technique, the cover glass 805 is coated with an organic thin film. With such an organic thin film, a visible light is emitted in accordance with an incident DUV light. In this way, the DUV light is detected as a visible light by a sensor that is sensitive only to the visible light.

Figure 41B:
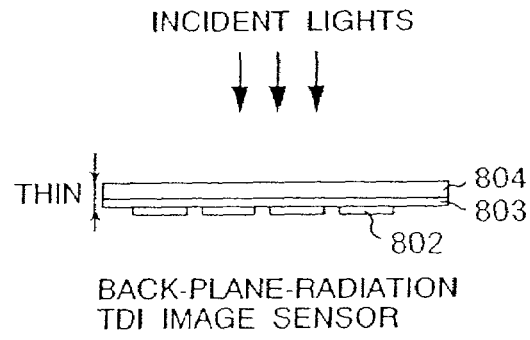

On the other hand, the thickness of the Si substrate 804 is reduced as shown in FIG. 41(b) to provide back-surface-radiation TDI image sensors which each receive an incident light hitting the thin Si substrate 804 on the rear side as the image sensors 205 and 206. Since an incident light hits the surface on the rear side including no gate structure, the DVD quantization efficiency is increased by about 10% or more to give a high quantization efficiency and a large dynamic range. As a result, the sensor becomes sensitive to a light having a wavelength of 400 nm or smaller. In addition, by having the image sensors 205 and 206 go TDI (Time Delay Integration) as described above, the sensitivity can be improved.

As described above, according to the fourth embodiment, by increasing the illumination on the periphery of the detection area 4 detected by the detectors 205 and 206 each implemented by typically a TDI image sensor to compensate for a decrease in MTF which becomes smaller as the detected position is separated away from the optical axis 2001 in the detection optical system comprising the components 201 to 204, the illumination efficiency can be increased. As a result, by employing a low-cost light source such as laser source, it is possible to detect a defect such as an infinitesimal foreign particle with a size in the range around 0.1 to 0.5 µm or even an infinitesimal foreign particle with a size smaller than about 0.1 µm on an inspected substrate such as an LSI wafer with a high degree of sensitivity and at a high throughput.

In addition, according to the fourth embodiment, an optical image based on a UVD (deep ultraviolet) laser light such as an exima laser light obtained from a substrate being inspected is made receivable by a TDI image sensor so that a defect such as an infinitesimal foreign particle with a size in the range around 0.1 to 0.5 µm or even an infinitesimal foreign particle with a size smaller than about 0.1 µm on the substrate being inspected can be detected.

The following description explains the image-signal processing unit 400 common to the first to fourth embodiments of the present invention described above.

Figure 27A:
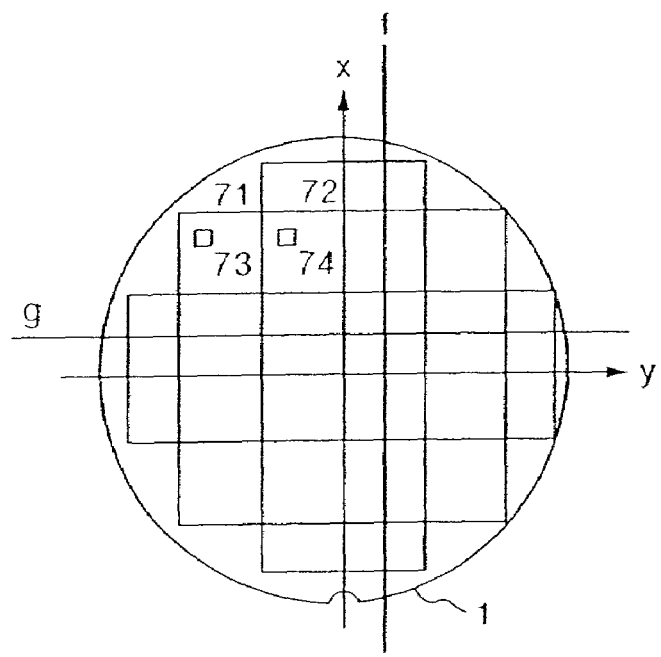
FIG. 27(a) is a diagram showing a relation between pixels and a wafer used for explaining why it is necessary to compute and set a criterion (threshold value) for extracting a defect such as a foreign particle in an image-signal processing unit provided by the present invention.
Figure 27B:
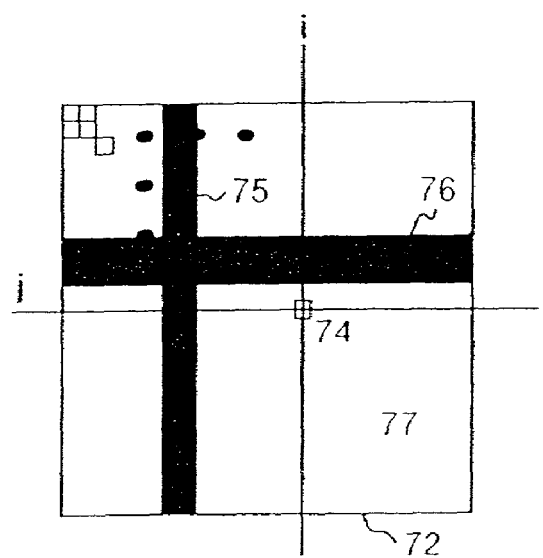
FIG. 27(b) is a diagram showing a relation between pixels and chips which each have a variety of pattern areas.

There are variations in detection signal received from the detectors 205 and 206. Such variations are caused by subtle differences in process for fabricating the device such as an LSI on the actual substrate 1 being inspected and caused by noise generated during the detection. For example, a signal level 73 for a pixel corresponding to a chip 71 is different from a signal level 74 for a pixel corresponding to a chip 72 as shown in FIG. 27(a), resulting in a variation. To put it concretely, variations in detection signal for locations 75, 76 and 77 with pattern structures different from each other are also different from each other as shown in FIG. 27(b). Examples of the locations 75, 76 and 77 with pattern structures different from each other are a memory-cell area, a peripheral-circuit area and an area of another type in the case of a memory LSI. As a result, in a portion with small variations, it is possible to detect a small defect generating relatively small signal changes. In a portion with big variations, on the other hand, it is possible to detect only a large defect generating relatively big signal changes.

In order to solve the problem described above, the present invention provides an image-signal processing unit 400 characterized in that a variation (a standard deviation) among chips is computed for each pixel in the chip and used for setting a threshold value, and a defect such as a foreign particle in an area with a small variation is detected by using a small threshold value while a defect such as a foreign particle in an area with a big variation is detected by using a large threshold value. In this way, the threshold value for an area with a small variation can be reduced without being affected by an area with a big variation. An example of an area with a small variation is the memory-cell area in the case of a memory LSI. As a result, it is possible to detect an infinitesimal foreign particle with a size not exceeding 0.1 µm.

Figure 28:
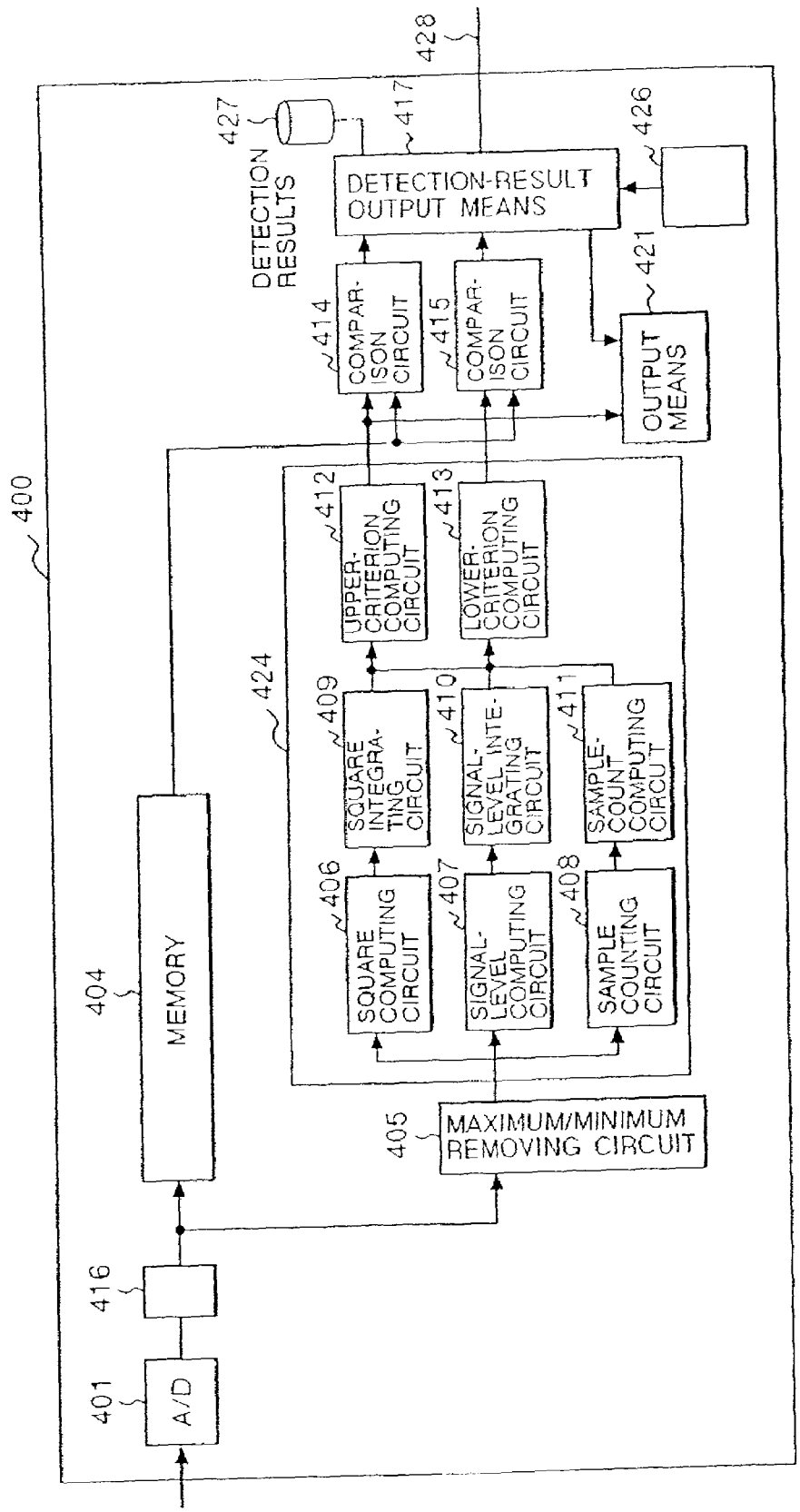
FIG. 28 is a block diagram showing a first embodiment of the image-signal processing unit provided by the present invention.

FIG. 28 is a diagram showing a first embodiment implementing the image-signal processing unit 400. As shown in the figure, the first embodiment implementing the image-signal processing unit 400 comprises: an A/D converter 401 for converting an analog image signal into digital data wherein the analog image signal represents concentration values accumulated for each array of pixels and is obtained synchronously with a movement of the inspected substrate 1 in the direction of the y axis from the image sensors 205 and 206 each implemented typically by a TDI image sensor; a start/stop command circuit 416 for establishing sampling timing; a data memory 404; a maximum/minimum removing circuit 405 for removing signals with maximum and minimum levels; a square computing circuit 406 for computing the square of a signal level s; a signal-level computing circuit 407 for computing the signal level s; a sample counting circuit 408; a square integrating circuit 409 for integrating squares of the signal level s; a signal-level integrating circuit 410 for integrating values of the signal level s; a sample-count computing circuit 411 for computing a sample count n by integration; a positive-threshold-value computing circuit (an upper-criterion computing circuit) 412; a negative-threshold-value computing circuit (a lower-criterion computing circuit) 413; a comparison circuit 414 for outputting a signal used for indicating a defect such as a foreign particle and obtained as a result of comparison of a detection signal temporarily stored in the data memory 404 with a positive threshold value computed and set by the positive-threshold-value computing circuit 412; a comparison circuit 415 for outputting a signal used for indicating a defect such as a foreign particle and obtained as a result of comparison of a detection signal temporarily stored in the data memory 404 with a negative threshold value computed and set by the negative-threshold-value computing circuit 413; and a detection-result output means 417 for outputting a result of detection comprising: the signals received from the comparison circuits 414 and 415 to indicate a defect such as a foreign particle; positional coordinates in a coordinate system established for the inspected substrate 1; and information on the inspected substrate 1. It should be noted that the maximum/minimum removing circuit 405 is not necessarily required. If the maximum/minimum removing circuit 405 is not employed, all detected pieces of image data including image data indicating a foreign particle are used in the computation of the threshold values so that the threshold values can be calculated with a high degree of accuracy and a high degree of stability. By using the computed threshold value, on the other hand, it is impossible to detect a foreign particle in an area for which the threshold value is computed. It is thus necessary to compute a threshold value for an area to be inspected from signals generated by an area corresponding to another chip array on the inspected substrate 1. In consequence, since a line for computing a threshold value is different from a line for inspection, the throughput of the inspection is reduced to a certain degree. Particularly, in the case of a low chip count, a threshold value can be computed by using image data spread over a plurality of lines. In this case, a data fetch position is specified by the start/stop command circuit 416.

The detection-result output means 417 is provided with a CPU for controlling the whole defect inspecting apparatus provided by the present invention for detecting a defect such as a foreign particle. The components 406 to 411 are used for finding a variation σ of a background signal for each predetermined area in a chip. The variation σ of a background signal for each predetermined area in a chip is then used by the positive-threshold-value computing circuit 412 and the negative-threshold-value computing circuit 413 to set a positive threshold value TH(H) and a negative threshold value TH(L) respectively which each serve as a criterion for extracting a signal indicating a defect such as a foreign particle. The components 406 to 413 constitute a threshold-value setting circuit 424. On the other hand, the data memory 404 is used for temporarily storing detected digital image signals till threshold values are set by the threshold-value setting circuit 424. Positional coordinates in a coordinate system established for the inspected substrate 1 are found on the basis of displacements of the stages measured by a measurement apparatus not shown in the figure and read signals (scanning signals) output by components such TDI image sensors with a reference mark on the inspected substrate 1 used as an origin. Reference numeral 421 denotes another output means for displaying the positive threshold value Th(H) showing a variation (a standard deviation σ) typically on a display means. By providing the display means 421, it is possible to form a judgment as to whether or not a threshold value is correct for each area in a chip while watching an output for a defect such as a foreign particle extracted from the comparison circuits 414 and 415.

The detection-result output means 417 may include a display means such as a CRT, a printing means for printing detection results as a hard copy, a recording means such as a hard disc, a floppy disc, an photo-magnetic recording medium, an optical recording medium, an LSI memory or an LSI memory card and a network connected to another inspection apparatus, an inspection system or a control system for controlling fabrication process equipment or fabrication lines. In addition, as described above, the detection-result output means 417 is provided with a CPU for controlling the whole defect inspecting apparatus provided by the present invention for detecting a defect such as a foreign particle.

The A/D converter 401 converts signals output by the detectors 205 and 206 each implemented typically a TDI image sensor into a digital signal representing a pixel signal. The A/D converter 401 can be placed on the same substrate as the detection signal processing system 400 or at a location in close proximity to the detectors 205 and 206 each implemented typically a TDI image sensor in the detection optical system 200. If the A/D converter 401 is at a location in close proximity to the detectors 205 and 206, the effect of noise is reduced due to digitization upon transmission but, on the other hand, there is a demerit of an increased number of signal transmission cables.

The following description explains signal processing carried out by the threshold-value setting circuit 424 with reference to FIG. 27. FIG. 27(a) is a diagram showing a typical layout of chips 71 and 72 and other devices on the wafer 1. In most of LSI fabrications, the same chips are created on the wafer repetitively. In some cases, a plurality of chips, for example, 2 to 4 chips, are created at the same time at a one-time exposure. Thus, at the locations of the chips, the same patterns are created. As a result, detection signals generated at the positions of the chips are naturally identical with each other.

Let notation $s(i, j, f, g)$ denote a signal of a pixel $(i, j)$ in a chip $(f, g)$. As described above, a signal level of a pixel in a chip should match a signal level of the corresponding pixel in another chip.

In actuality, however, there are variations in pixel detection signal s among chips which are caused by subtle differences among processes but do not indicate a defect, and noise observed in the detection. In addition, even in the same chip, the variation at a location with a pattern structure is different from the variation at another location with another pattern structure.

The threshold values Th(H) and Th(L) are found from the variation (or the standard deviation $\sigma(s, f, g)$) of the detection signal $s(i, j, f, g)$ between a location in a chip and a corresponding location in another chip in accordance with Eq. (8) as follows:

$$Th(H)=\mu(s,f,g)+m1\times\sigma(s(i,j,f,g),f,g)$$

$$Th(L)=\mu(s,f,g)-m1\times\sigma(s(i,j,f,g),f,g) \quad (8)$$

where notations Th(H) and Th(L) denote the positive and negative threshold values set by the positive-threshold-value computing circuit 412 and the negative-threshold-value computing circuit 413 respectively whereas notation $\mu(s, f, g)$ denotes the average of the values of the signal for different values of f and g. The average is computed by using Eq. (9) as follows:

$$\mu(s,f,g)=(\Sigma s)/n \quad (9)$$

where $\Sigma s(i, j, f, g)$ is computed by the signal-level computing circuit 407 for computing the signal level s and the signal-level integrating circuit 410 for integrating the signal level s whereas n is computed by the sample counting circuit 408 and the sample-count computing circuit 411.

Computed in accordance with Eq. (10) below, $\sigma(s, f, g)$ is a standard deviation of the signal s for different values of f and g. m1 denotes a multiplier (coefficient).

$$\sigma(s,f,g)=\sqrt{(\Sigma s^2/n - \Sigma s/n)} \quad (10)$$

where $\Sigma s(i, j, f, g)^2$ is computed by the square computing circuit 406 for computing the square of a signal level s and the square integrating circuit 409 for integrating the square of the signal level s.

As described above, the threshold values are found by using a value obtained as a result of multiplication of the standard deviation $\sigma(s, f, g)$ by a multiplier m1. Normally, it is considered to be desirable to set the value of the multiplier m1 at about 6. This is because the probability of generation of a value of at least 6σ is about $1\times10^{-11}$. At this probability, the number of pixels detected from a wafer with a diameter of 300 mm for pixel dimensions of 2×2 μm is $7\times10^{10}$. Thus, the value 6 of the multiplier m1 is found from the fact that areas on the entire surface of the wafer generating detection signals exceeding the threshold values (or the so-called false information) are statistically smaller in size than 1 pixel. Of course, the value of the multiplier m1 does not have to be set at 6. In other words, it is needless to say that another value can be selected in order to display the effect of the present invention. Also from the fact that the number of pieces of false information does not have to be smaller than 1, it is quite within the bounds of possibility that another value of the multiplier m1 can be selected.

FIG. 4 is a diagram showing a second embodiment implementing the image-signal processing unit 400. The second embodiment is different from the first embodiment in that an image signal of 1 chip is delayed by the data memory 402 and a difference processing circuit 403 extracts a difference in image signal between chips $\Delta s=\{s(i, j, f, g)-s(i, j, f+1, g)\}$. Thus, the comparison circuits 414 and 415 extract signals each indicating a defect such as a foreign particle as a result of comparison of this differential signal $\Delta s=\{s(i, j, f, g)-s(i, j, f+1, g)\}$ with the upper threshold value Th(H) and the lower threshold value Th(L) expressed by Eq. (11) below.

Thus, the threshold-value setting circuit comprising the components 406 to 413 sets the upper threshold value Th(H) and the lower threshold value Th(L) based on Eq. (11) as follows:

$$Th(H)=+m1\times\sigma(s(i,j,f,g)-s(i,j,f+1,g),f,g)$$

$$Th(L)=-m1\times\sigma(s(i,j,f,g)-s(i,j,f+1,g),f,g) \quad (11)$$

It should be noted that the standard deviation $\sigma(\Delta s, f, g)$ of the differential image between adjacent chips is computed by using Eq. (12) as follows.

$$\sigma(\Delta s,f,g)=\sqrt{(\Sigma\Delta s^2/n - \Sigma\Delta s/n)} \quad (12)$$

where $\Sigma\Delta s$ is computed by the signal-level computing circuit 407 for computing the signal level $\Delta s$ and the signal-level integrating circuit 410 for integrating the signal level Δs whereas n is computed by the sample counting circuit 408 and the sample-count computing circuit 411. ΣΔs² is computed by the square computing circuit 406 for computing the square of a signal level Δs and the square integrating circuit 409 for integrating the square of the signal level Δs.

By using the differential image Δs between adjacent chips in this way, the standard deviation σ is small even if the detected image signal in the chip exhibits distribution. As a result, a defect such as a foreign particle can be detected with a higher degree of sensitivity.

Assume that the process condition varies stage by stage from area to area starting from the center toward the outermost circumference of a wafer. In this case, the signal level also changes stage by stage from area to area starting from the center toward the outermost circumference of the wafer. As a result, the variation (or the standard deviation σ(s, f, g)) used in the computation of the threshold values based on Eq. (8) increases. However, the difference in signal between only adjacent chips (or the standard deviation σ(Δs, f, g)) is actually not so large as that used in Eq. (8), making it possible to detect a defect by using threshold values which are smaller. Thus, the computations using Eqs. (11) and (12) which are based on the differential value Δs allow threshold values of lower levels to be resulted in.

As an improved technique, threshold values can also be computed by using Eq. (13) as follows.

$$Th = m1 \times \sigma(|s(i,j,f,g) - s(i, j, f+1, g)|, f, g) \quad (13)$$

where notation |Δs| denotes the absolute value of the differential signal Δs.

In order to compute threshold values by using Eq. (13), the difference processing circuit 403 is replaced by an absolute-difference processing circuit 403' to provide image-signal processing units 400 shown in FIGS. 29 and 30. A threshold-value computing circuit 423 computes a threshold absolute value Th and a comparison circuit 414 compares the absolute value of a differential signal with the threshold value Th to extract a signal indicating a defect such as a foreign particle.

It should be noted that, in this case, the standard deviation σ(|Δs|, f, g) of a difference in image between adjacent images is computed by using Eq. (14) as follows:

$$\sigma(|\Delta s|, f, g) = \sqrt{(\Sigma \Delta s^2/n - \Sigma |\Delta s|/n)} \quad (14)$$

where Σ|Δs| is computed by the signal-level computing circuit 407 for computing the signal level |Δs| and the signal-level integrating circuit 410 for integrating the signal level |Δs|.

Figure 29:
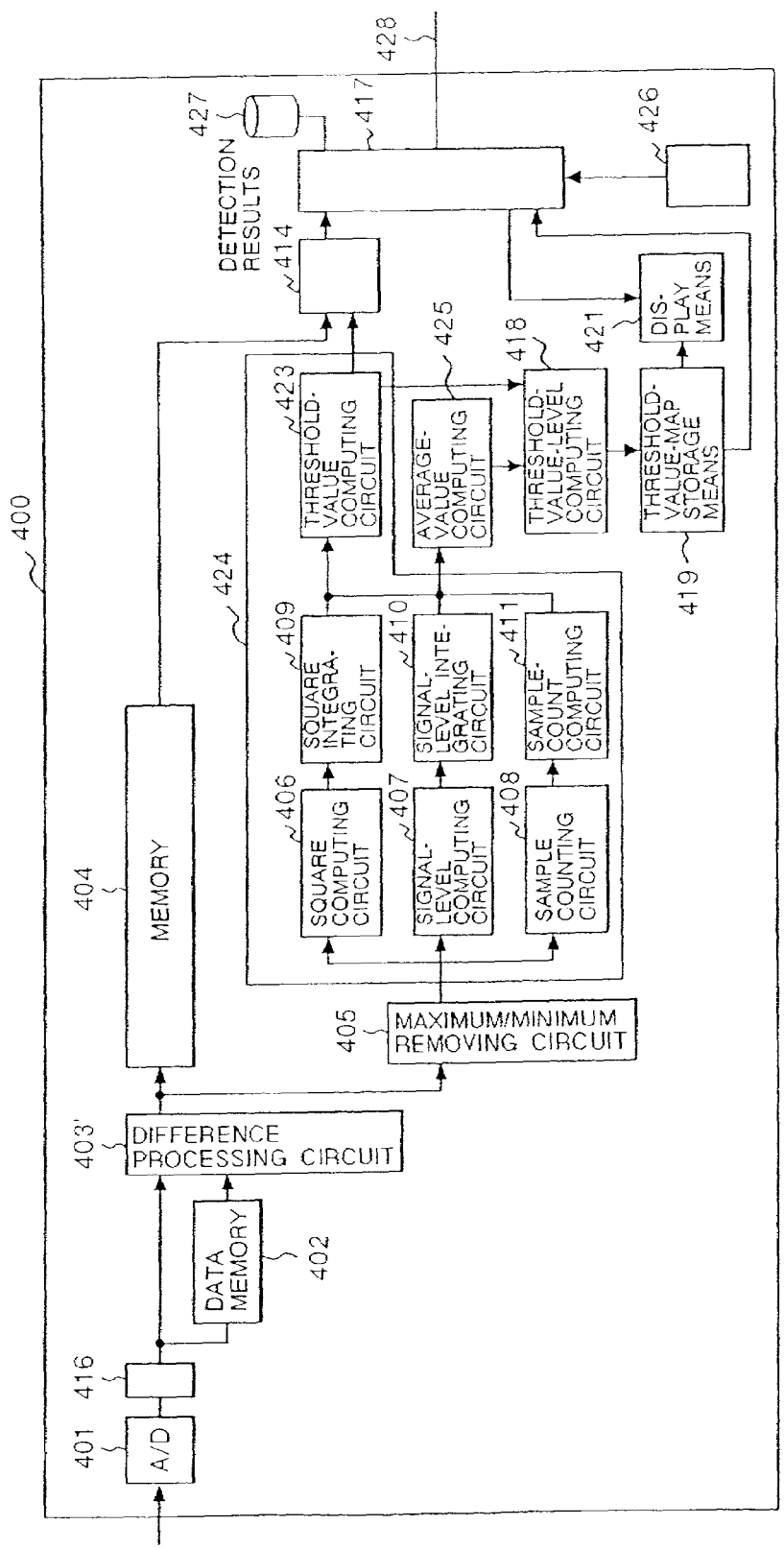
FIG. 29 is a block diagram showing a third embodiment of the image-signal processing unit provided by the present invention.
Figure 30:
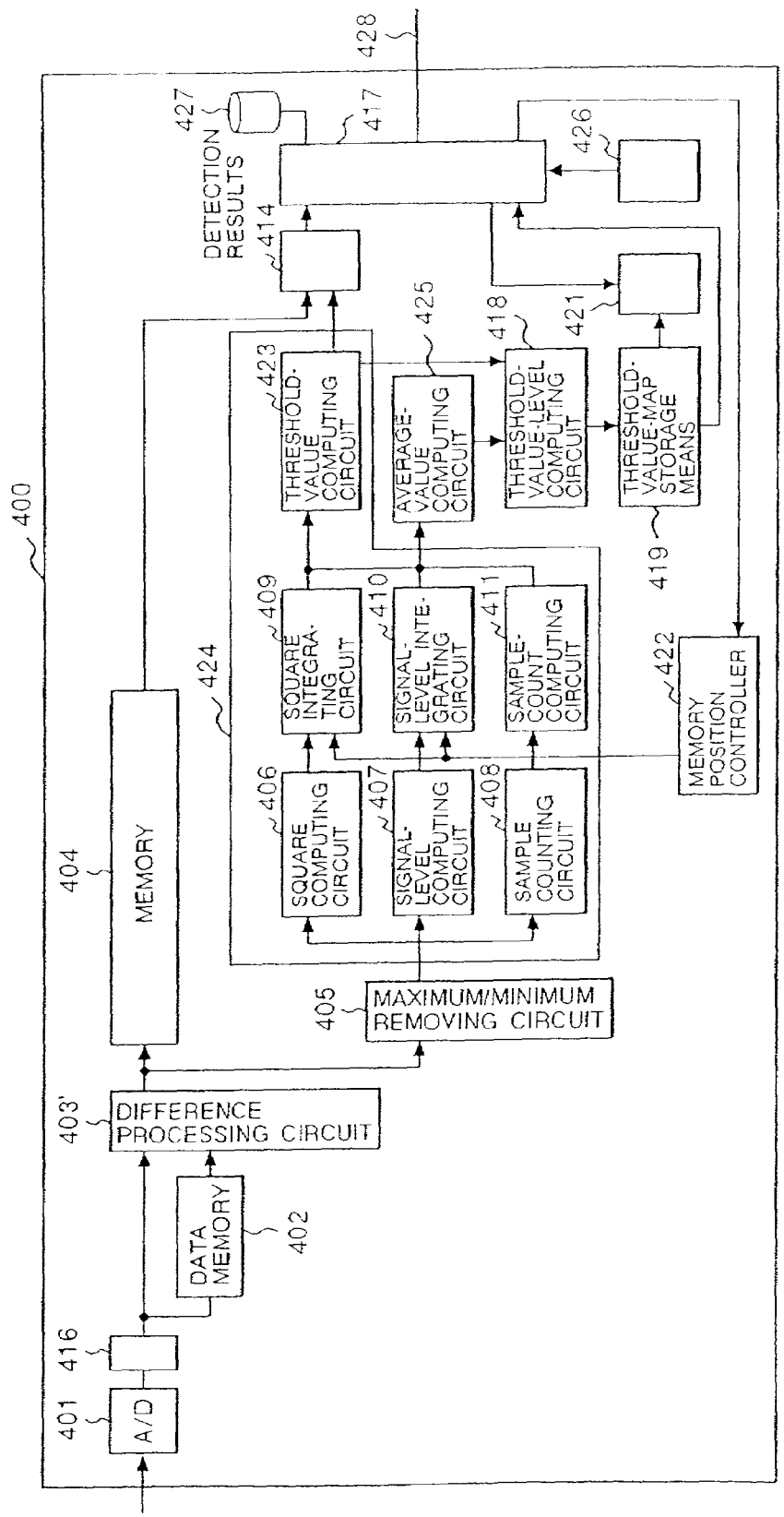
FIG. 30 is a block diagram showing a fourth embodiment of the image-signal processing unit provided by the present invention.

By the way, in comparison with the third embodiment shown in FIG. 29, the fourth embodiment shown in FIG. 30 has an additional memory position controller 422. The memory position controller 422 specifies coordinates of the detection signal s or the differential signal Δs on the wafer. That is to say, coordinates of pixels on the wafer, for which a standard deviation σ between chips is found, can be specified arbitrarily. In addition, since coordinates on the wafer can be specified arbitrarily, a standard deviation σ can also be found from areas surrounding target pixels on chips.

In the case of the third embodiment shown in FIG. 29, positional coordinates on the wafer are found from a result of counting the number of signals. This technique of finding positional coordinates is good for a case in which a standard deviation σ is found from chips laid out on a horizontal array. However, this technique can not be used to find a standard deviation σ from chips on different arrays.

In order to solve this problem, the memory position controller 422 computes positional coordinates of an incoming detection signal s or an incoming differential signal Δs from signals of the stage coordinate system and the like which are obtained from the stage controller 305 as is the case with the third embodiment. The computed positional coordinates are then supplied to the square integrating circuit 409, the signal-level integrating circuit 410 and the sample-count computing circuit 411 which each have a memory function. In this way, data produced by the square integrating circuit 409, the signal-level integrating circuit 410 and the sample-count computing circuit 411 can be stored in the storage destination, that is, at the coordinates of the detection signal With such a configuration, the number of samples for computing a standard deviation can be increased even in the case of a wafer periphery at which the number of chips on an array is small. As a result, the threshold-value computing circuit 423 is capable of computing stable threshold values.

By letting the absolute-difference processing circuit 403 compute the absolute value of a difference as described above, there is exhibited an effect of, among others, a reduced storage size of the data memory 404 since data to be stored therein does not have a sign. In addition, from a result of computation of an absolute value, a calculated standard deviation σ can be made smaller than a calculation result obtained from a differential value. In order to obtain a generation probability of 1×10⁻¹¹, or to get a '6σ' on the normal distribution, a magnification of about 10 which is about 1.66 times '6' is required. That is to say, it can be considered that a calculated standard deviation σ can be reduced to a value equal to 0.6 times a calculation result obtained from a differential value.

In addition, with this technique, a threshold value for a signal level s is not left, raising a problem in process control and failure analyses. In order to solve this problem, there is provided a circuit 418 for computing the level of a threshold value for a position (i, j) in a chip as a threshold-value map as shown in FIGS. 29 and 30. In this circuit 418, a threshold-value map is computed from a sum (σ×m1+Σ|Δs|/n) in which the product σ×m1 is calculated by the threshold-value computing circuit 423 in accordance with Eq. (14) where the symbol σ denotes a standard deviation and the symbol m1 denotes a multiplier, and the average Σ|Δs|/n of the absolute values of differential signals is computed by the average-value computing circuit 425. The result of the computation by the circuit 418 for each positional data (i, j) computed from the positions of the stages 301 and 302 as well as the sensors 205 and 206 is stored in a threshold-value-map storage means 419 which has a memory for each pixel (i, j) on the entire chip. The threshold-value map can be displayed on a threshold-value map output means such as a display means 421 as requested by the user. In addition, a threshold-value map and outputs each indicating a defect such as a foreign particle extracted from the comparison circuit 414 are also displayed on the display means 421, allowing the user to form a judgment as to whether or not the threshold values are proper. Furthermore, by supplying information of the threshold-value map to the detection-result output means 417, it is possible to output a threshold-value map and pieces of data each indicating a defect such as a foreign particle extracted from the comparison circuit 414.

Related to the condition of an underlying layer, the threshold-value level corresponds to information indicating whether or not the underlying layer is a repetitive-pattern area, an area including a terribly poor spot, a thin-film area or an area with small pattern dimensions. It is thus important to analyze which threshold-value level a detected foreign particle has been detected with respect to. Therefore, it will be meaningful to output a threshold value at a position of a detected foreign particle as data of the detected foreign particle added to the signal level of the foreign particle by displaying the threshold value on the display means 421. For this reason, the computed threshold-value map is required.

By the way, instead of the signal level s of a foreign particle which is 'a differential value+a threshold value', it can be considered to be the use of the differential value Δs.

In addition, as underlying data at the position of a detected foreign particle, information derived from design data can also be used in addition to the threshold-value level described above. Examples of such information are information on an area in a chip such as a memory area, a logic-circuit area, a power-supply area and a wireless area. In order to make such information available, a map of areas in a chip is made from the design data, then an information or a phrase being similar to threshold-value data which is coded from coordinates of the made area map may be output by being displayed in an operation to display a detected foreign particle.

Furthermore, it is possible to output by displaying underlying area data of any of the types described above, in the form of a foreign particle map for each type of underlying data or in the form of a foreign particle count for each type of underlying data.

As described above, according to the basic concept of the present invention, the magnitude of the variation of a signal is found and a threshold value is determined in accordance with the found magnitude of the variation of the signal. In a typical configuration of the present invention, the threshold-value setting circuit 424 computes a threshold value for each of corresponding pixels in chips from data of the chips acquired in advance. Threshold values are computed in advance for the same processes of LSIs of the same type. The computed threshold values are typically stored in a threshold-value memory employed in the threshold-value setting circuit 424 to be compared by the comparison circuits 414 and 415 with sequentially incoming signal levels. Data used in the computation of threshold values can be found once for a lot which normally comprises 13 to 25 wafers or found for each wafer.

It should be noted that, in the present invention, since a threshold-value level varies in dependence on the condition of an underlying layer as described above, the threshold-value level represents the condition of the underlying layer. That is to say, the CPU as an output means 417 is capable of knowing what underlying layer a defect such as a foreign particle exists on or is attached to, provided that signals each indicating a defect such as a foreign particle are classified by threshold-value levels obtained from the threshold-value-map storage means 419. The condition of an underlying layer, for example, indicates that the underlying layer is an area with no pattern, an area of cells or an area of peripheral patterns. As an alternative, the CPU 417 can be inputted CAD information from a CAD system by way of an input means 426 which is typically implemented by a network or storage media. In this case, the CPU 417 produces area data in a chip like the ones shown in FIGS. 1 and 2 on basis of the inputted CAD information and is capable of further knowing directly the condition of an underlying layer being existed a defect such as a foreign particle by using the area data in a chip.

The technique of inferring the condition of an underlying layer from a signal level or a threshold-value level of the underlying layer without using area data exhibits an effect that it is not necessary to set areas in a chip in advance. In this case, the CPU 417 is capable of classifying signal levels of the underlying layer as areas such as cell units from the magnitudes of threshold-value levels of the entire chip found once from a threshold-value map stored in threshold-value-map storage means 419. In this case, a judgment for an area can be formed by comparing the threshold-value level with a difference Δs in signal level between adjacent chips or the signal level itself. After knowing the condition of the underlying layer, the CPU 417 is capable of detecting, outputting and controlling a defect or a foreign particle only, for example, on a cell unit.

Figure 31:
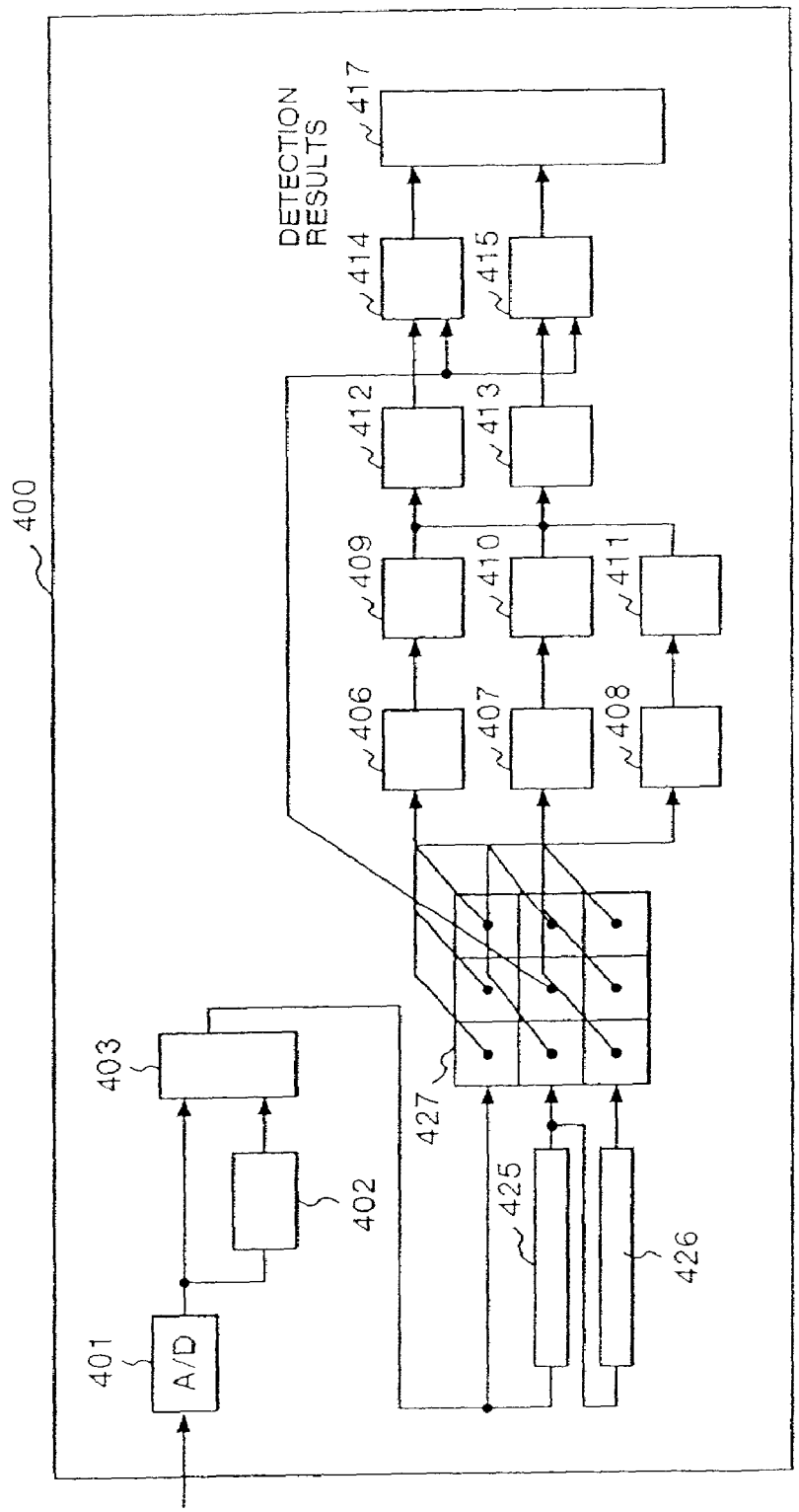
FIG. 31 is a block diagram showing a fifth embodiment of the image-signal processing unit provided by the present invention.

Next, a fifth embodiment implementing the central processing unit 400 is explained by referring to FIG. 31. The fifth embodiment computes a difference Δs in detection signals (or data) between adjacent chips and then finds a variation (or a standard deviation σ(Δs, f, g)) of data surrounding a target pixel.

The fifth embodiment includes delay memories 425 and 426 and a window opening circuit 427 to form the so-called pipeline processing system. Components 406 to 413 compute the variation σ(Δs, f, g) from periphery pixels' differential values Δs(i+1, j+1, f, g), Δs(i+1, j, f, g), Δs(i+1, j−1, f, g), Δs(i, j−1, f, g), Δs(i−1, j−1, f, g), Δs(i−1, j, f, g), Δs(i−1, j+1, f, g) and Δs(i, j+1, f, g) of a window excluding a central differential value Δs(i, j, f, g) of the window in accordance with Eq. (15) given below. Then, the threshold values Th(H) and Th(L) are computed in the basis of the computed standard deviation σ.

$$\sigma(\Delta s, f, g) = \sqrt{(\Sigma \Delta s^2/8 - \Sigma s/8)} \qquad (15)$$

The comparison means 414 and 415 compare the central differential value Δs(i, j, f, g) of the window cited above with the computed threshold values Th(H) and Th(L) respectively to extract a defect such as a foreign particle. The dimensions of the window do not have to be 3×3 as shown in the figure. Instead, they can be 4×4, 5×5 or 7×7. As an alternative, the computation can be applied to a plurality of window sizes. In addition, the object of inspection is not necessarily the central differential value. Instead, the object of inspection can be any differential value in the window. As another alternative, the object of inspection can be another value such as an average or a sum of differential values of a plurality of pixels on the window. The size of the window should be determined in accordance with the size of a foreign particle to be detected or the shape of a background pattern.

The following description explains a sixth embodiment implementing the central processing unit 400 wherein a threshold value of the absolute sensitivity is set. By setting a threshold value of the absolute sensitivity based on Eq. (13) given above, the control size of a foreign particle or a defeat in LSI fabrication processes can be made uniform for all the processes.

The CPU 417 of the detection signal processing circuit 400 corrects a signal level or preferably a differential signal level ss which is received as a result of detection in addition to coordinates of a foreign particle.

To put it concretely, the differential signal level ss is corrected into a differential signal level ss' in accordance with Eq. (16) as follows:

$$ss' = ss/(P1 \times ND \times k \times rb \times k(t)) \qquad (16)$$

where the symbol P1 denotes the power of a laser generated during inspection, the symbol ND denotes the ND of the ND filter expressed in terms of %, the symbol k denotes a constant indicating whether or not a polarization plane exists, the symbol rb denotes the reflectance of the underlying layer and the symbol k(t) denotes a correction coefficient dependent on the thickness t of the oxide film. A value of 1 of the constant k indicates that a polarization plane exists while the constant k is desirably set at around 10 to indicate that a polarization plane does not exist. It should be noted that, since the laser power P1 exhibits a distribution characteristic P1(x) known as the so-called shading over illumination positions along the x axis, the value of P1(x) can be substituted for P1 in Eq. (16) to give a better result.

The size d of a foreign particle or a defect is a function df(ss) of differential signal level ss obtained in advance. In actuality, the size d of a foreign particle or a defect displayed on the display means 421 is found by substituting the corrected differential signal level ss' for the differential signal level ss in the function df(ss) as follows:

$$d=df(ss') \quad (17)$$

In particular, for a small foreign particle, according to Mie's scattering theory, the corrected differential signal level ss' is proportional to the (−6)th power of the size d of the foreign particle. Thus, the size d of the foreign particle can also be found from this proportional relation.

The following description explains an embodiment implementing the central processing unit 400 wherein a judgment on the existence of a defect is based on a high S/N ratio for of course an infinitesimal foreign particle and a large foreign particle having a spreading shape. By the way, it is necessary not only to detect an infinitesimal foreign particle but also not to miss a large foreign particle or a foreign particle having a thin-film shape spread over a range of several microns by using the comparison circuits 414 and 415 employed in the central processing unit 400 for forming a judgment on the existence of a defect. Since a high-level detection signal is not always generated by such a large foreign particle, however, the S/N ratio of a detection signal of a pixel unit is low, causing such a large foreign particle to be neglected.

Let the symbol S denotes an average detection signal level of 1 pixel and notation σ/n denotes an average variation. By convolution for an extracted unit having dimensions of n pixels×n pixels which correspond to the size of a large foreign particle, the level of the detection signal is found to be $n^2S$, the variation is found to be nσ and the S/N ratio is found to be nS/σ. If a large foreign particle is detected in pixel units, on the other hand, the level of the detection signal is found to be S, the variation is found to be σ and the S/N ratio is found to be S/σ. Thus, by convolution for an extracted unit having dimensions of n pixels×n pixels which correspond to the size of a large foreign particle, the S/N ratio is increased by n times.

As for an infinitesimal foreign particle with a size of about 1 pixel, the level of a detection signal detected for a 1-pixel unit is found to be S, the variation is found to be σ and the S/N ratio is found to be S/σ. By convolution for an extracted unit having dimensions of n pixels×n pixels in the case of an infinitesimal foreign particle with a size of about 1 pixel, on the other hand, the level of the detection signal is found to be $S/n^2$, the variation is found to be nσ and the S/N ratio is found to be S/nσ. Thus, for an infinitesimal foreign particle with a size of about 1 pixel, by keeping the signal of a pixel unit as it is, the S/N ratio can be increased.

Figure 52:
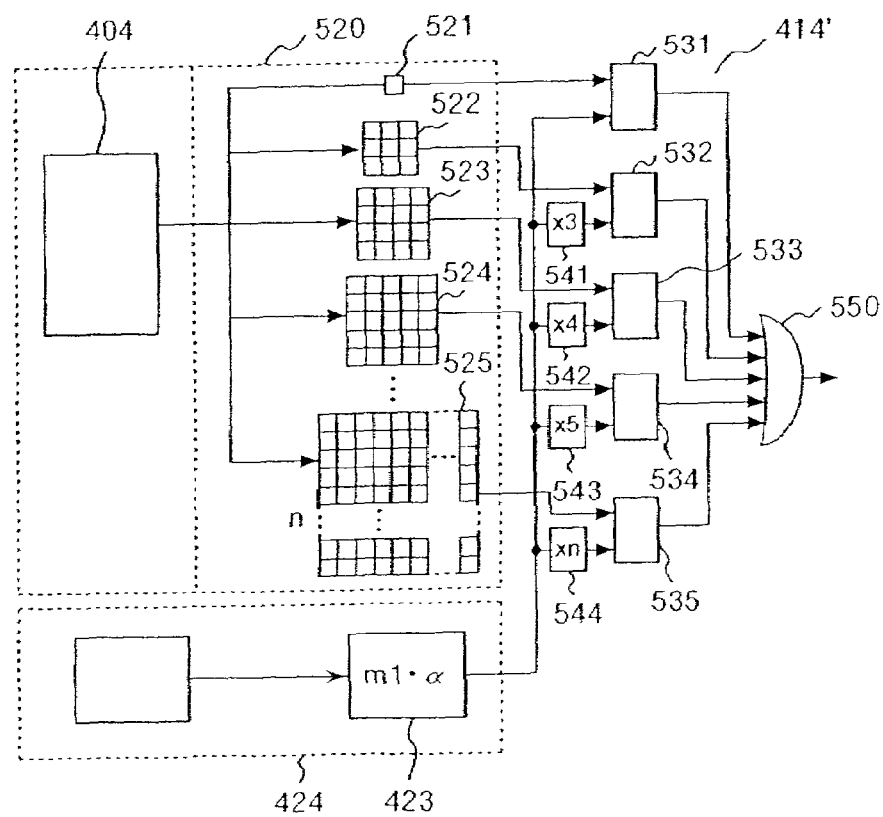
FIG. 52 is a diagram showing the configuration of a defect inspecting apparatus provided by the present invention which is capable of forming a judgment as to whether or not a defect exists at high S/N ratios for foreign particles ranging from an infinitesimal defect to a defect exhibiting a spreading characteristic.

It is thus obvious from the description given above that, by convolution of an image signal obtained from the data memory 404 for each extracted operator 520, a gray scale image signal with different levels is output from pixels at the center. There are a plurality of operators 520 with different dimensions expressed in terms of pixel units for detection of a defect. As shown in FIG. 52, examples of the operators 520 are an operator 521 extracted as 1 pixel unit, an operator 522 extracted as a unit of 3 pixels×3 pixels, an operator 523 extracted as a unit of 4 pixels×4 pixels, an operator 524 extracted as a unit of 5 pixels×5 pixels and an operator 525 extracted as a unit of n pixels×n pixels. In this case, the levels of the gray scale image signal are S, 9S, 16S, 25S and $n^2S$ for the operators 521, 522, 523, 524 and 525 respectively where the symbol S denotes an average detection signal level of 1 pixel. On the other hand, multiplication circuits 541, 542, 543 and 544 multiply a threshold value m1×σ output by a threshold-value circuit 423 employed in the threshold-value setting circuit 424 by approximation threshold-value coefficients 3, 4, 5 and n respectively. These approximation threshold-value coefficients 3, 4, 5 and n are inferred from the central limit theorem. Comparison circuits 531, 532, 533, 534 and 535 constitute a comparator 414'. In the comparison circuit 531, the gray scale image signal obtained as a result of the convolution at the operator 521 is compared with the threshold value m1×σ in order to form a judgment on the existence of a defect such as a foreign particle and to output a signal indicating a foreign particle in accordance with the outcome of the judgment. In the comparison circuit 532, on the other hand, the gray scale image signal obtained as a result of the convolution at the operator 522 is compared with a threshold value obtained as a product of the threshold value m1×σ and the approximation threshold-value coefficient 3 in order to form a judgment on the existence of a defect such as a foreign particle and to output a signal indicating a foreign particle in accordance with the outcome of the judgment. Likewise, in the comparison circuit 533, the gray scale image signal obtained as a result of the convolution at the operator 523 is compared with a threshold value obtained as a product of the threshold value m1×σ and the approximation threshold-value coefficient 4 in order to form a judgment on the existence of a defect such as a foreign particle and to output a signal indicating a foreign particle in accordance with the outcome of the judgment. Similarly, in the comparison circuit 534, the gray scale image signal obtained as a result of the convolution at the operator 524 is compared with a threshold value obtained as a product of the threshold value m1×σ and the approximation threshold-value coefficient 5 in order to form a judgment on the existence of a defect such as a foreign particle and to output a signal indicating a foreign particle in accordance with the outcome of the judgment. Similarly, in the comparison circuit 535, the gray scale image signal obtained as a result of the convolution at the operator 525 is compared with a threshold value obtained as a product of the threshold value m1×σ and the approximation threshold-value coefficient n in order to form a judgment on the existence of a defect such as a foreign particle and to output a signal indicating a foreign particle in accordance with the outcome of the judgment. That is to say, the comparison circuit 531 detects an infinitesimal foreign particle with a size of about 1 pixel. On the other hand, the comparison circuit 532 detects a foreign particle with dimensions of about 3 pixels×3 pixels. Similarly, the comparison circuit 533 detects a foreign particle with dimensions of about 4 pixels×4 pixels. Likewise, the comparison circuit 534 detects a foreign particle with dimensions of about 5 pixels×5 pixels. Similarly, the comparison circuit 535 detects a foreign particle with dimensions of about n pixels×n pixels. A logical-sum circuit 550 computes a logical sum of the signals output by the comparison circuits 531 to 535 each to indicate a foreign particle. Thus, signals indicating foreign particles with different dimensions can be detected each at a high S/N ratio. As a result, the degree of complementation can be raised for a large foreign particle generating a low detection-signal level and having a spread shape.

It should be noted that, by providing operators with different dimensions expressed in terms of pixels for forming a judgment on the existence of a defect such as a foreign particle after the difference processing circuit 403' and a pixel signal is integrated to generate an output each time the dimensions expressed in terms of pixels are changed, the comparator 414 is made capable of detecting a signal indicating a foreign particle with a size matching the changed dimensions expressed in terms of pixels. In this case, however, it is necessary to carry out the inspection a plurality of times by changing the dimensions expressed in terms of pixels. Nevertheless, an accurate value is set as a threshold value. In addition, if operators with different dimensions expressed in terms of pixels for forming a judgment on the existence of a defect such as a foreign particle are provided after the difference processing circuit 403', an image memory 404 with a storage capacity increased by a plurality of times is required. However, it is not necessary to provide more than one threshold-setting circuit 424. In addition, a threshold value $m1 \times \sigma$ output by a threshold-value circuit 423 employed in the threshold-value setting circuit 424 can be multiplied by an approximation threshold-value coefficient to find a final threshold value.

As described above, by adjusting dimensions expressed in terms of pixels for formation of a judgment on the existence of a defect such as a foreign particle by integration or convolution of a rectangular function to the size of a foreign particle to be detected in the comparator 414', it is possible to catch a large foreign particle generating a low detection-signal level and having a spread shape.

Figure 42:
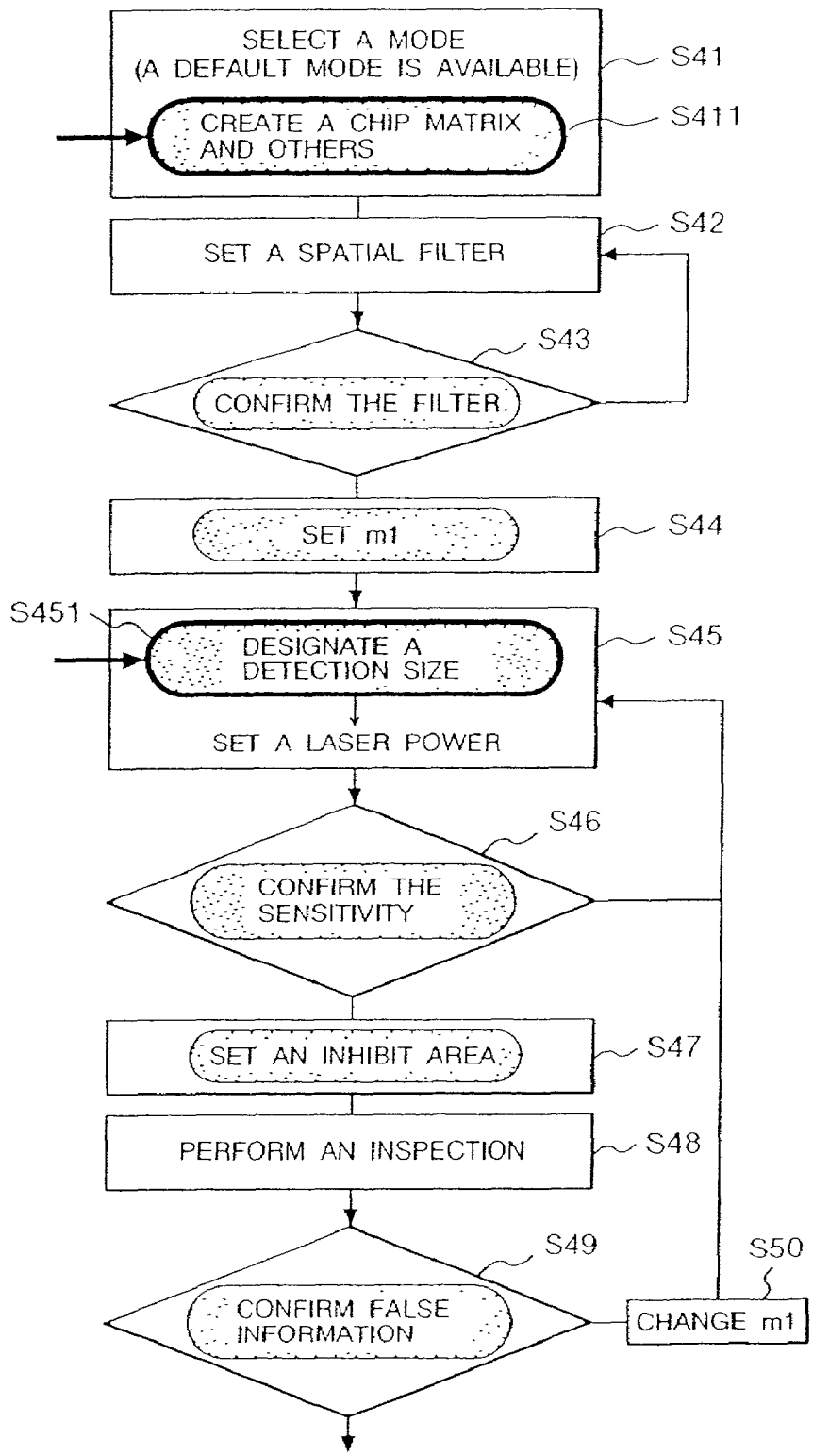
FIG. 42 is a diagram showing an embodiment of a sequence of condition specifying processes in a defect inspecting apparatus provided by the present invention.

The next description explains embodiments implementing a technique of specifying conditions adopted in the defect inspecting apparatus provided by the present invention for detecting a defect such as a foreign particle by referring to FIGS. 42 to 46. FIG. 42 is a diagram showing a sequence of specifying conditions followed by the defect inspecting apparatus provided by the present invention for detecting a defect such as a foreign particle. Inspection of a substrate for a defect is carried out under conditions set in this sequence.

Figure 43:
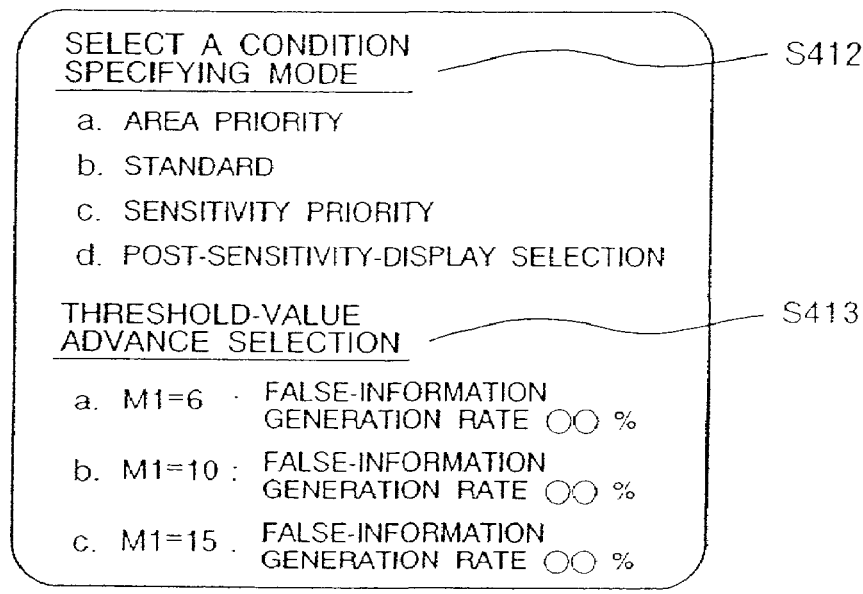
FIG. 43 is a diagram showing a screen displayed on a display means and used for selecting a condition specifying mode and selecting a threshold value in advance.
Figure 44:
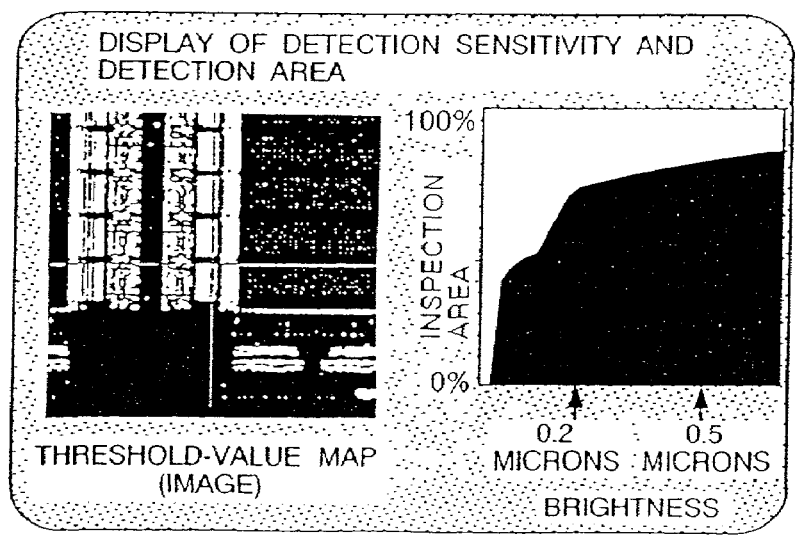
FIG. 44 is a diagram showing a screen appearing on a display means to show detection sensitivities and detection areas.

As shown in FIG. 42, the sequence begins with a step S41 at which the CPU 417 displays a screen for selecting one of a variety of modes like ones shown in FIG. 43 on the display means 421. By using an input means 426 such as a keyboard or a mouse, the user is allowed to select an item in each mode. Typical modes include a chip matrix S411 on a wafer, a condition specifying mode S412 and a threshold-value advance selection mode S413. Selectable items of the chip matrix S411 are items related to chip layout data such as the size of the chip, the start coordinates of the chip and information indicating non-existence of a chip. As shown in FIG. 43, selectable items of the condition specifying mode S412 are: a. Area priority; b. Standard; c. Sensitivity priority; and d. Post-sensitivity-display selection. On the other hand, selectable items of the threshold-value advance selection mode S413 are: a. m1=6: False-information generation rate of OO%; b. m1=10: False-information generation rate of OO %; and c. m1=15: False-information generation rate of OO %.

Figure 45:
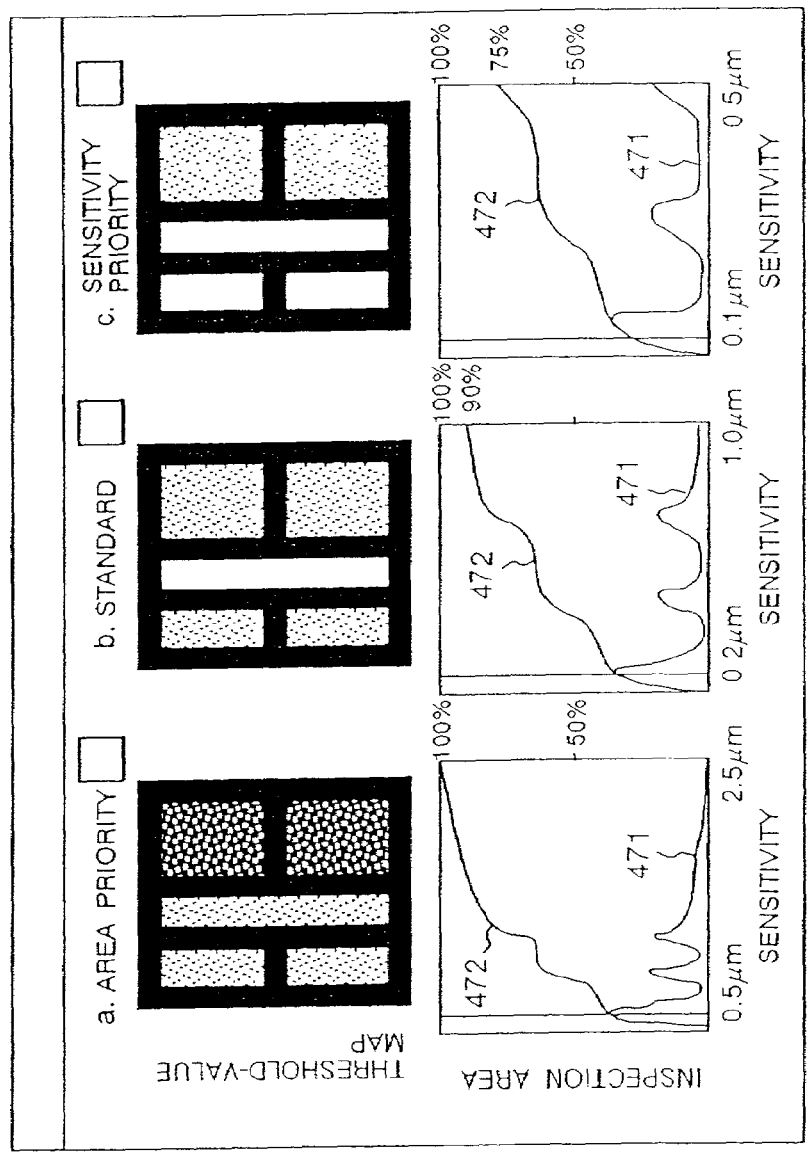
FIG. 45 is a diagram showing a screen appearing on a display means to show threshold value maps for area-priority, standard and sensitivity-priority modes as well as relations between the sensitivity and the inspection area.

The 'a. Area priority' of the condition specifying mode S411 is an inspection-condition mode which allows a relatively large foreign particle in an area larger than the standard mode to be detected by typically weakening the power of the illumination beam. An area with a saturated background level is virtually an uninspectable area. In the area-priority mode, however, the size of an uninspectable area can be made 5% or smaller. FIG. 45 is a diagram showing a case in which the area-priority mode allows a foreign particle having a size of about 2.5 µm to be detected from the entire area.

The 'b. Standard' of the condition specifying mode S412 is an inspection-condition mode which allows a foreign particle to be detected at a standard sensitivity. FIG. 45 is a diagram showing a case in which the standard mode allows a foreign particle having a size of about 1.0 µm to be detected from about 90% of the entire inspection area and furthermore to a foreign particle having a size of about 0.2 µm to be detected.

The 'c. Sensitivity priority' of the condition specifying mode S412 is a mode with the sensitivity set at such a high value that a foreign particle more infinitesimal than that of the standard mode can be detected, or an inspection-condition mode set to allow a specified detection sensitivity to be preserved. FIG. 45 is a diagram showing a case in which the sensitivity-priority mode allows a foreign particle having a size of about 0.5 µm to be detected from about 75% of the entire inspection area and furthermore to a foreign particle having a size of 0.1 µm to be detected. To put it concretely, by increasing the power of the illumination light, the power of the illumination light is set at a level capable of assuring an inspection condition allowing a foreign particle smaller in size than a foreign particle indicated by a specified detection size or assuring a specified detection sensitivity. In the examples shown in FIG. 45, the inspection condition allows a foreign particle having a size of about 0.1 µm to be detected or the specified detection sensitivity allows a foreign particle having a size of about 0.5 µm to be detected from at least 75% of the inspection area.

The 'd. Post-sensitivity-display selection' of the condition specifying mode S412 is a mode displaying results of inspection obtained in one of the 3 modes described above, or a map of threshold values in a chip or a relation between the size (the sensitivity corresponding to the threshold value) and the inspection area (a threshold-value histogram) and allowing the user to select an appropriate item among what are displayed.

In the area-priority mode, the power of the illumination light is lowest and the dynamic range is wide. When the defect inspecting apparatus is switched from the area-priority mode to the standard mode, the power of the illumination light is increased while the dynamic range is reduced. The same holds true when the defect inspecting apparatus is switched from the standard mode to the sensitivity-priority mode. Thus, in the case of the area-priority mode, in the threshold-value map, there are only few uninspectable areas from which a foreign particle can not be detected, but only foreign particles with a size of up to about 0.5 µm can be detected. In the standard mode, there are many saturated uninspectable areas from which a foreign particle shown in a white color in FIG. 45 can not be detected. However, foreign particles with a size of up to about 0.2 µm can be detected. In the case of the sensitivity-priority mode, there are even more saturated uninspectable areas from which a foreign particle shown in a white color in FIG. 45 can not be detected. However, foreign particles with a size of up to about 0.1 µm can be detected. In the threshold-value histograms, reference numeral 471 denotes a relation between the sensitivity and the inspection area rate, whereas reference numeral 472 denotes a relation between the sensitivity and the integration value of the inspection area. It should be noted that a threshold-value histogram can also show only one of the relations 471 and 472.

An item in the threshold-value advance selection mode S413 can be selected in accordance with an allowable probability of generation of false information by checking this allowable probability with the displayed probabilities of generation of false information (the generation frequencies) OO %. This is because, as described earlier, since a threshold value is set from the variation σ of the level of a detected image-picture signal, the probability of generation of false information OO % can be automatically computed for a display from the multiplier m1 on the basis of the theory of statistics. Thus, the threshold value setting and the multiplier m1 for the probability of generation of false information can be displayed with ease.

Figure 46:
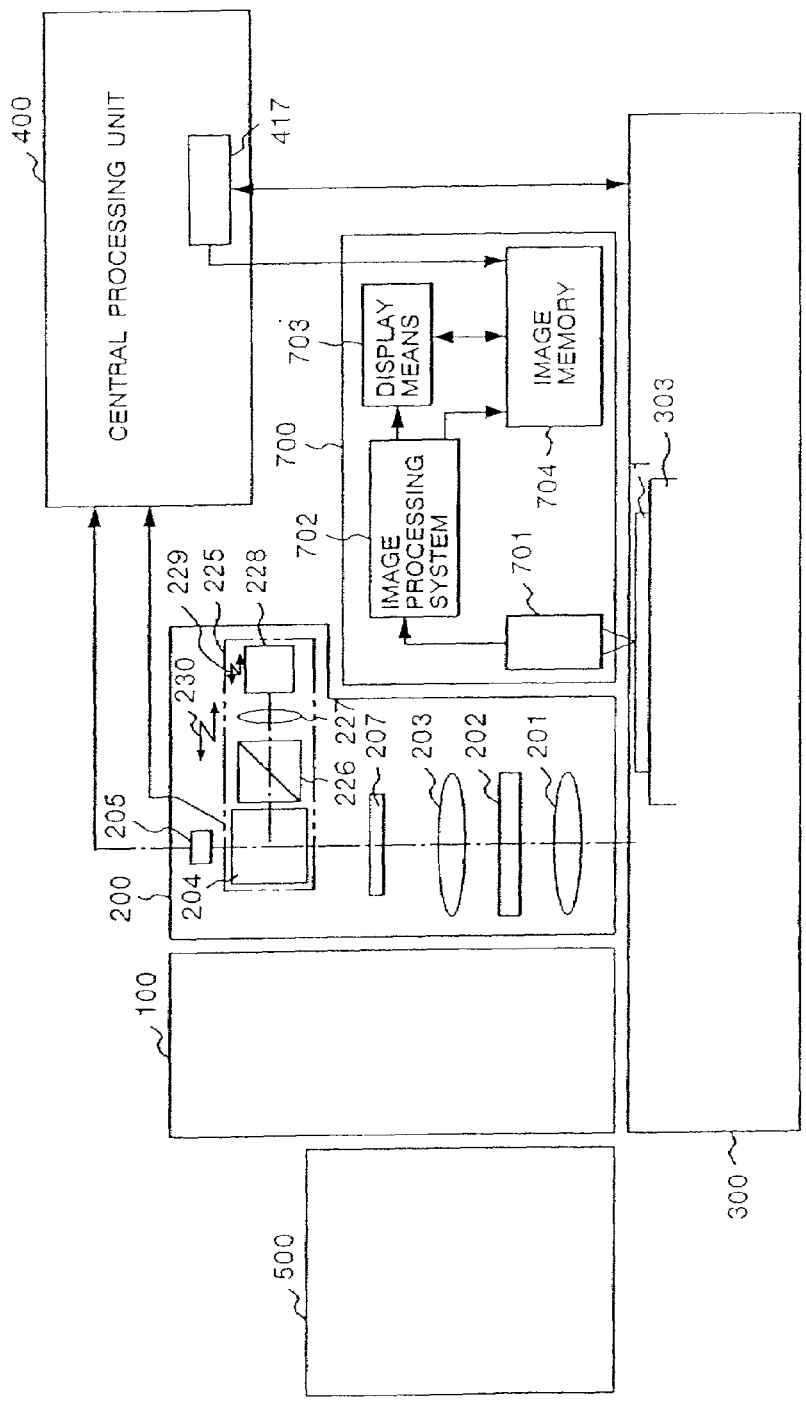
FIG. 46 is a diagram showing an embodiment implementing a defect inspecting apparatus including a detection optical system having an optical subsystem for observing a shielded-light pattern of a spatial filter and an optical-observation microscope.

The CPU 417 then goes on to the next step S42 of the flow of the sequence shown in FIG. 42. At the step S42, the spatial filter 202 is set either manually or automatically in accordance with the structure of a circuit pattern on a selected wafer. The CPU 417 then proceeds to a step S43 at which an image formed by the spatial filter 202 is confirmed either by visual observation or automatically by using an image formed by a TV camera 228 and the image-formation optical system 227, a focus of which is adjusted to the position of the filter as shown in FIG. 46. If the image is not confirmed, the CPU 417 then goes back to the step S42 to again set the spatial filter 202. If the image is confirmed, on the other hand, the CPU 417 goes on to the next step. The spatial filter 202 has a configuration wherein the pitch and the phase of its optical shielding pattern can be changed. As shown in FIG. 46, a single assembly 225 comprises a beam splitter 204 and a spatial-filter observation optical system which comprises a half mirror 226, the image-formation lens 227 and the TV camera 228. The internal structure of the assembly 225 can be changed as shown by an arrow 230. To be more specific, in an operation to detect an ordinary foreign particle, the beam splitter 204 is placed on the detection optical axis 204. In a spatial-filter observation, on the other hand, it is the half mirror 226 that is placed on the detection optical axis. In an automatic operation, by subjecting a diffraction light and an optical shielding pattern detected in the aperture 20a to an image-pickup operation carried out by the TV camera 228 in the same way as that shown in FIG. 19(b), the pitch and the phase of the optical shielding pattern can be adjusted so that the diffraction light is shielded. In addition, by shifting the position of the TV camera 228 in a direction indicated by an arrow 229 in FIG. 46, it is also possible to adjust the directivity of the optical shielding pattern while observing also the image of a circuit pattern on the substrate being inspected.

Then, the flow of the sequence goes on to a step S44 at which the CPU 417 inputs a value of the magnification (coefficient) m1 in the range around 6 to 15 for the standard deviation σ for setting a threshold value Th from the input means 426. The flow of the sequence then goes on to a step S45 at which the CPU 417 inputs a detection size of a foreign particle from the input means 426 in size specification S451. The detection size of a foreign particle is used for computing a laser power which can be used to detect a foreign particle having the specified size. The laser-beam source 101 is then controlled by a control signal 430 to generate a laser beam having the computed laser power.

Then, the CPU 417 goes on to a step S46 at which, in order to set threshold values for a partial area or the entire area of a chip, the wafer is scanned and inspected and a threshold-value map computed by the threshold-value computing means 418 is stored in the threshold-value-map storage means 419. Then, the threshold-value map (or a threshold-value image) like the one shown in FIG. 44 or threshold-value histograms like the ones shown in FIG. 45 are displayed on the display means 421. The histograms shown in FIG. 45 each represent a relation between the sensitivity and the inspection area having the sensitivity with the sensitivity represented typically by the horizontal axis. Each of the histograms shown in FIG. 45 also represents a relation between the sensitivity and the integration value of the inspection area. The user is then allowed to check the sensitivity on the basis of typically the displayed threshold-value map to confirm whether the threshold value is at a desired level (the size of a foreign particle to be detected). If such a threshold value is not confirmed, the flow of the sequence goes back to the step S45. If such a threshold value is confirmed, on the other hand, the flow of the sequence goes on to the next step S47.

As described above, the CPU 417 goes on to the step S47 at which the entire area of the wafer is inspected. If an area generating false information exists, such an area may be set as a non-inspection area (an inhibit area) on the basis of CAD information in the chip or information included in the threshold-value map. The flow of the sequence then goes on to a step S48 at which the CPU 417 issues a command to inspect the substrate 1 for a defect such as a foreign particle. If the central processing unit 400 determines that a defect such as a foreign particle exists, the level of the detection signal and detection coordinates of the defect are stored in a storage unit 427.

Finally, the flow of the sequence goes on to a step S49 at which the actual inspected substrate 1 is optically observed by using an optical-observation microscope 700 implemented typically by an ultraviolet-ray microscope or a common-focus microscope installed besides the defect inspecting apparatus in order to confirm whether a result of the inspection indicates a defect such as a foreign particle or is false information. With this confirmation, it is possible to confirm whether a condition specification has been set properly for the first time. In particular, if an area including an infinitesimal and complicated circuit pattern coexists with an area causing color nonuniformity in a chip on the inspected substrate 1, it is necessary to finally confirm the condition specification by using the optical-observation microscope 700. If the result of the confirmation of false information done at the step S49 is NO, the flow of the sequence goes on to a step S50 at which the magnification (coefficient) m1 for setting a threshold value is increased or decreased in some cases. The flow of the sequence then goes back to the step S45 at which the laser power is changed if necessary. In the case of a YES result, on the other hand, the condition specifying sequence is ended.

It should be noted that the objective can be achieved even if only part of the procedure described above is adopted or if the flow of the sequence is changed.

As described above, it is possible to specify conditions optimum for a desired size (sensitivity) of a foreign particle with ease and within a short period of time.

It should be noted that, in the optical observation carried out at the step S49, the detected foreign particle (including that false information) on the inspected substrate 1 can be moved to the position of a detection optical system 701 employed in the optical-observation microscope 700 shown in FIG. 46 by moving the stages 301 and 302 so as to allow the inspector to observe the image thereof. In the case of the detection optical system 200, the image-formation optical subsystem thereof has a high resolution and, in addition, coordinates of a point of observation are changed during a movement of the object of inspection with a high degree of precision. In particular, the dark-visual-field illumination optical system comprising the components 102 to 105 allows a foreign particle with a size smaller than the resolution limit of the detection optical system 200 to be detected. Thus, with an ordinary microscope, observation is impossible in many cases. For this reason, the optical-observation microscope 700 is employed. As the optical-observation microscope 700, it is desirable to employ typically a common-focus optical system with an extremely high resolution or an optical system with a short wave illumination light such as ultraviolet rays or deep ultraviolet rays with a typical wavelength of 248 nm, 365 nm or 266 nm or a wavelength close thereto. That is to say, for a wavelength of about 200 nm, the optical-observation microscope 700 is capable of producing an image close to an image formed by an electron microscope as well as allows the size of a defect such as a foreign particle to be found with a high degree of precision attributes including shapes of defects such as foreign particles to be classified. It should be noted that FIG. 46 shows the configuration of the optical-observation microscope 700. As shown in FIG. 41, the optical-observation microscope 700 comprises: the aforementioned detection optical system 701 having a bright-visual-field or dark-visual-field ultraviolet-ray illumination optical subsystem and a TDI image sensor of FIG. 41 capable of detecting an ultraviolet ray; an image-signal processing unit 702 for carrying out processing such as A/D conversion of an image detected by the TDI image sensor of the detection optical system 701; an image memory 704 for storing an image completing the A/D conversion in the image-signal processing unit 702 at an address based on coordinate data of a foreign particle (or that considered to be false information) detected by the central processing unit 400; and a display means 703 for displaying an image. Thus, by controlling the stages 301 and 302 in accordance with coordinate data of a foreign particle (or that considered to be false information) detected by the central processing unit 400 to display an image considered to be false information on the display means 703 for observation by the inspector, the inspector is capable of confirming the false information by using the optical-observation microscope 700. To put it in detail, the stages 301 and 302 are moved to take the position indicated by detection coordinates stored in the storage unit 427 to the visual field of the optical-observation microscope 700, and the optical-observation microscope 700 detects an image in the visual field and displays on the display means 703 or stores the image in the image memory 704 as numerical image data. This stored data can be redisplayed when necessary. In addition, data stored in the image memory 704 can be supplied to the CPU 417 of the central processing unit 400 and observed later along with image data transferred from another defect inspecting apparatus. Anyway, as the optical-observation optical system 700, a bright-visual-field microscope having a high resolution, a dark-visual-field microscope having the illumination optical system 100 described above, a dark-visual-field microscope having incoherent illumination, a phase-differential microscope or a common-focus microscope can be employed.

In the condition specifying sequence described above, the specification of conditions can be completed by merely making a chip matrix at the step S41 and entering the size of a foreign particle to be detected at the step S45. That is to say, a chip matrix and the size of a foreign particle (or a sensitivity corresponding to the size of a foreign particle) are conditions that absolutely need to be specified.

In other words, the confirmation of the filter at the step S43, the setting of the multiplier m1 at the step S44, the confirmation of a sensitivity at the step S46, the setting of an inhibit area (a non-inspection area) at the step S47 and the confirmation of false information at the step S49 are optional condition setting steps.

In addition, in setting of a threshold value, the use of a threshold value on the stable side (a large threshold value) suppresses generation of false information. By decreasing the threshold value, on the other hand, a foreign particle can be detected with a high degree of sensitivity even if false information is generated to a certain degree. The former technique is suitable for quality control of a wafer processing apparatus and therefore used for detecting an abnormality. The latter technique is on the other hand suitable for an analysis of a state of generation of a failure and a defect, and thus used for classifying defects and foreign particles in determining a cause of generation of a failure.

Figure 47:
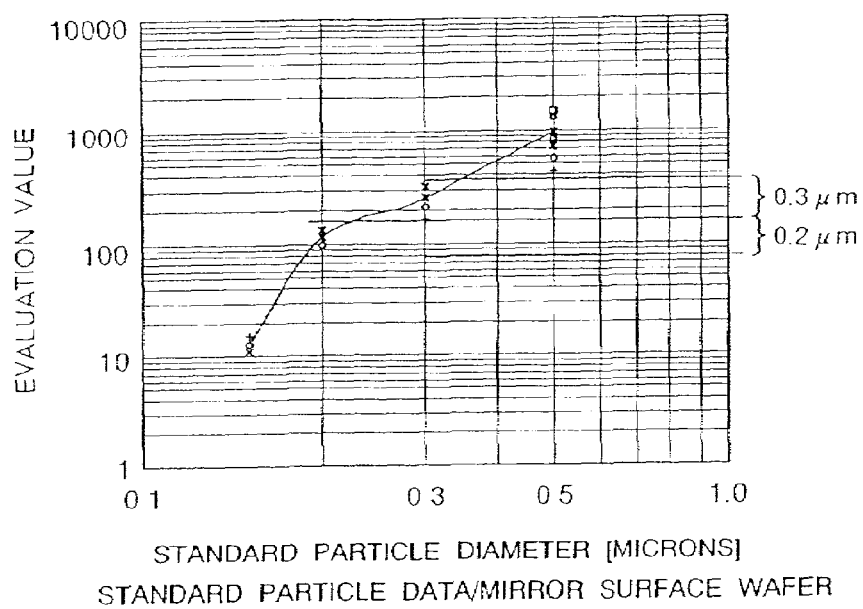
FIG. 47 is a diagram showing a relation based on empirical data between an evaluation value (a level of a detection signal of scattered lights) and a standard diameter of particles on a reflecting-surface wafer used in the present invention.

The following description explains inference of the diameter of a foreign particle carried out by the CPU 417 from a scattered-light image stored in the image memory 404 as a result of processing comprising detection by the image sensors 205 and 206 and A/D conversion by the A/D-conversion unit 401 by referring to FIG. 47. The level of a signal representing a scattered light or, the more desirable differential value ss, varies in accordance with the size of a particle or a defect such as an injury which generates the scattered light. The CPU 417 corrects the detection signal ss by multiplying the signal ss by a correction coefficient k(t) to produce a corrected detection signal ss'. In this case, the correction coefficient k(t) is calculated in accordance with conditions including the power of the laser beam, the polarization plane 208 on the inspection, the spatial filter 202 and the illumination angles $\phi 1$ and $\alpha 1$ in such a way that the corrected detection signal ss' can be made representative of the size d of an external material or a defect such as an injury. The CPU 417 uses information on the size of a foreign particle or a defect calculated in this way as a size to be normally specified in the detection-size specification at the step S45 of the condition specifying sequence described earlier.

As described earlier, an image representing a foreign particle is detected by the TDI image sensors 205a and 206a and stored in the image memory 404. A relation between the size of the image (or the number of pixels showing the spread of the image of the foreign particle) and the dimensions of the foreign particle exhibits a certain trend as shown in FIG. 47. Thus, the CPU 417 is capable of inferring the diameter of the foreign particle by computing the number of pixels showing the foreign particle with such pixels obtained from a detected image stored in the image memory 404. Particularly, in the case of a foreign particle having a size in the range around 0.13 to 0.2 μm, a correlation between the size and the dimensions of the image of the foreign particle can be found out. As a result, the size of a foreign particle or the diameter of a foreign particle can be inferred.

Figure 48A:
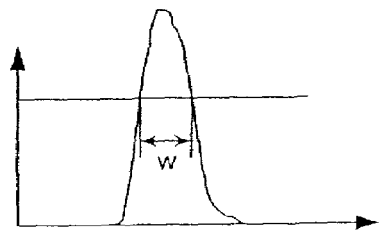
FIGS. 48(*a*) and 48(*b*) are explanatory diagrams used for describing an embodiment for inferring the size of a foreign particle from a detected image signal.
Figure 48B:
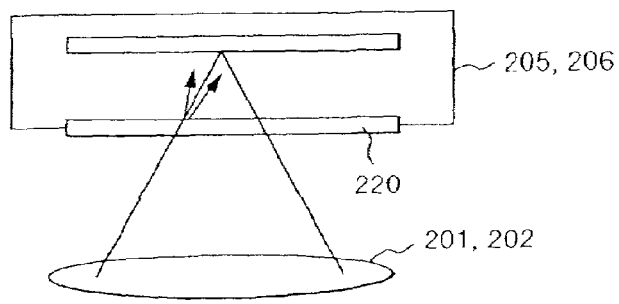

In addition, in the case of a foreign particle size accommodatable in one pixel and a signal level exceeding the dynamic range of the image sensors 205 and 206, the size of the foreign particle can be inferred by using the following technique. Even if the size of a foreign particle can be accommodated in one pixel, an image exhibiting a spread as shown in FIG. 48(a) is formed. From the width between the rise and the fall of this spread, that is, from the width W of the threshold value, the intensity of a signal exceeding a peak level or the dynamic range can be inferred. In this case, as shown in FIG. 48(b), the surface condition of the cover glasses 220 of the image sensors 205 and 206 is set at a specific surface roughness to let the cover glasses 220 cause scattering and produce a spreading forcibly. In this way, the size of a foreign particle can be inferred more easily from a detection image.

Next, a plurality of inspections by the defect inspecting apparatus provided by the present invention are explained. In the inspections, in order to provide a dynamic range, for example, the surface of the inspected substrate 1 is inspected in the area-priority mode, the standard mode and the sensitivity-priority mode, that is, under a condition of an increasing power of the illumination light, and in the standard mode or in a condition of a reduced power of the illumination light. Results of the inspections are then supplied to the CPU 417. The results of the inspections can be simply integrated into an inspection-result map. The inspection-result map is a drawing showing plotted defect marks at positional coordinates at which defects such as foreign particles have been detected. The CPU 417 may also produce a list of coordinates of foreign particles or a list/map showing detection-signal levels of foreign particles in place of such an inspection-result map.

In addition, a plurality of inspections are carried out not only to provide a dynamic range, but carried out also in order to allow detection of a defect such as an infinitesimal injury or foreign particle by changing typically the travel times of the stages 301 and 302. Furthermore, the inspections are also carried out by changing conditions such as the directions $\alpha1$, $\phi1$ (including 0) and $\phi2$ (including 0) of the illumination set by the illumination optical system 100, the presence/absence of the polarization plane 208 and the use of the white-color illumination 500 and the laser illumination 100.

Figure 49:
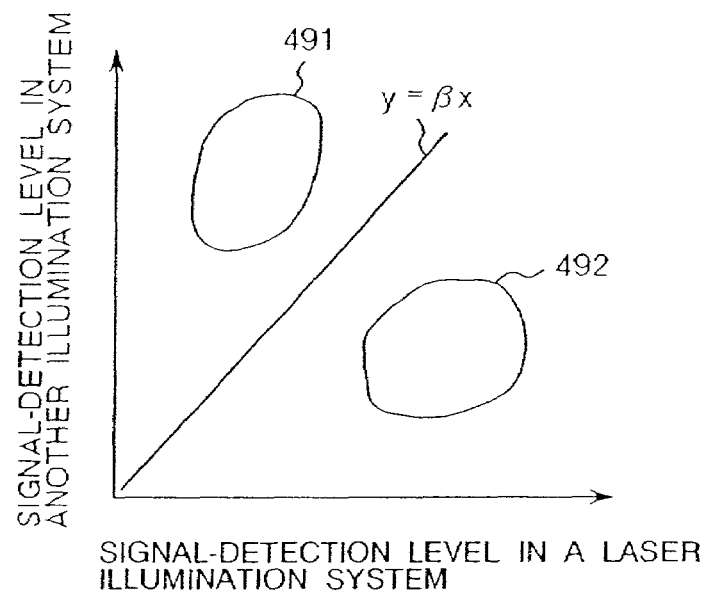
FIG. 49 is an explanatory diagram used for describing an embodiment capable of classifying the types of defects from the level of a signal detected by a laser radiating system and the level of a signal detected by another radiation system.

In addition, as a technique of processing adopted by the CPU 417, the corrected detection-signal level ss' of a defect detected under a plurality of inspection conditions is mapped onto a space of multi dimensions such as the power of the illumination light, the illumination directions, the presence/absence of the polarization plane, the white-color illumination and the laser illumination to produce classified results from a distance in the space with the class portion separated. For example, as shown in FIG. 49, curves are each plotted to show a relation between the level ss' of a detection signal produced by the laser-illumination optical system 100 on the x axis and the level ss' of a detection signal produced by another illumination optical system such as the white-color illumination system 500 and the illumination system shown in FIG. 50 on the y axis. The curves are plotted in 2 areas separated by a straight line represented by $y=\beta x$ set in advance. The classification of the relations into these 2 areas allows a characteristic of a defect to be identified. As described above, the illumination system shown in FIG. 50 can be used as another illumination system. In this case, results of experiments have verified that a defect such as a foreign particle with a relation thereof plotted in the area represented by $y>\beta x$ is an injury or a flat foreign particle 491 which is not much illuminated by an illumination light in a slanting direction. On the other hand, a defect such as a foreign particle with a relation thereof plotted in the area represented by $y<\beta x$ is a foreign particle 492 with a relatively large height. The boundary line between the 2 areas does not have to be a straight line. That is to say, the boundary line can also be a curve for example. As a matter of fact, a plurality of straight and/or curved lines can serve as boundaries between areas. In addition, a space for finding these distances can have a plurality of dimensions. Further, these inspections can be carried out by using the detectors 205 and 206 at the same time.

Figure 50:
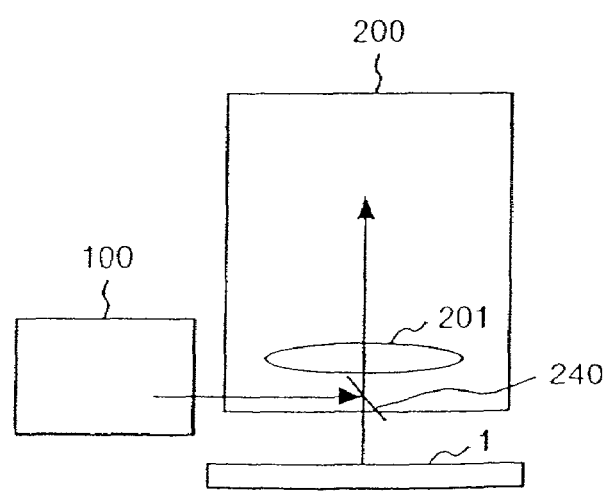
FIG. 50 is a diagram showing the configuration of a defect inspecting apparatus of the present invention including a detection optical system and an illumination optical system for radiating a beam by adoption of a bright visual field technique by means of a straight-line-shaped fine mirror.

Instead of radiating the laser beams 10, 11 and 12 as shown in FIG. 3 in slanting illumination directions, the illumination system shown in FIG. 50 radiates a laser beam 3 to the inspected substrate 1 in a direction substantially perpendicular to the surface of the substrate 1 by reflecting the laser beam 10 using a straight-line-shaped fine mirror 240 which is inserted between the objective lens 201 and the inspected substrate 1. Thus, a 0th-order diffraction light (a regularly reflected light) is shield ed by the straight-line-shaped fine mirror 240 while a first-order diffraction light and higher-order diffraction lights pass through the objective lens 201. Note that it is desirable to design the straight-line-shaped fine mirror 240 into a band of a sufficiently fine straight-line shape so that, on the surface of the spatial filter 202, the functions of the spatial filter 202 can be executed.

Next, connection of the defect inspecting apparatus provided by the present invention to external equipment is explained. As described above, the CPU 471 controls the entire defect inspecting apparatus provided by the present invention. For this reason, data such as results of inspection and conditions for inspection such as particularly a threshold-value map is stored in the storage unit 427 connected to the CPU 417. It is also desirable to communicate the results of inspection and conditions for inspection stored in the storage unit 427 to another computer through a local area network 428 or a modem. In particular, by connecting the defect inspecting apparatus to the Internet, information such as improvements of the conditions for inspection and states of problems encountered in the defect inspecting apparatus can be exchanged between the user utilizing the defect inspecting apparatus and the manufacturer of the apparatus. If information exchanged between the user and the manufacturer of the defect inspecting apparatus is encrypted by using an encryption key known by both the user and the manufacturer, security of data can be protected. In addition, information such as improvements of the conditions for processing and states of problems encountered in the processing apparatus based on results of inspection of substrate for a defect such as a foreign particle produced by the defect inspecting apparatus can also be exchanged between the user utilizing the processing apparatus and the manufacturer of the apparatus.

Further, by designing the image-signal processing unit 400 as a programmable system, algorithms adopted by the units 400 shown in FIGS. 4, 28, 29, 30 and 31 can each be implemented as a program which can be executed by the system. These algorithms each keep up with partial fluctuations in signal intensity caused by interference of typically an oxide film on the surface of a wafer. It is thus possible to implement an algorithm for dealing with the so-called color irregularities.

Figure 32:
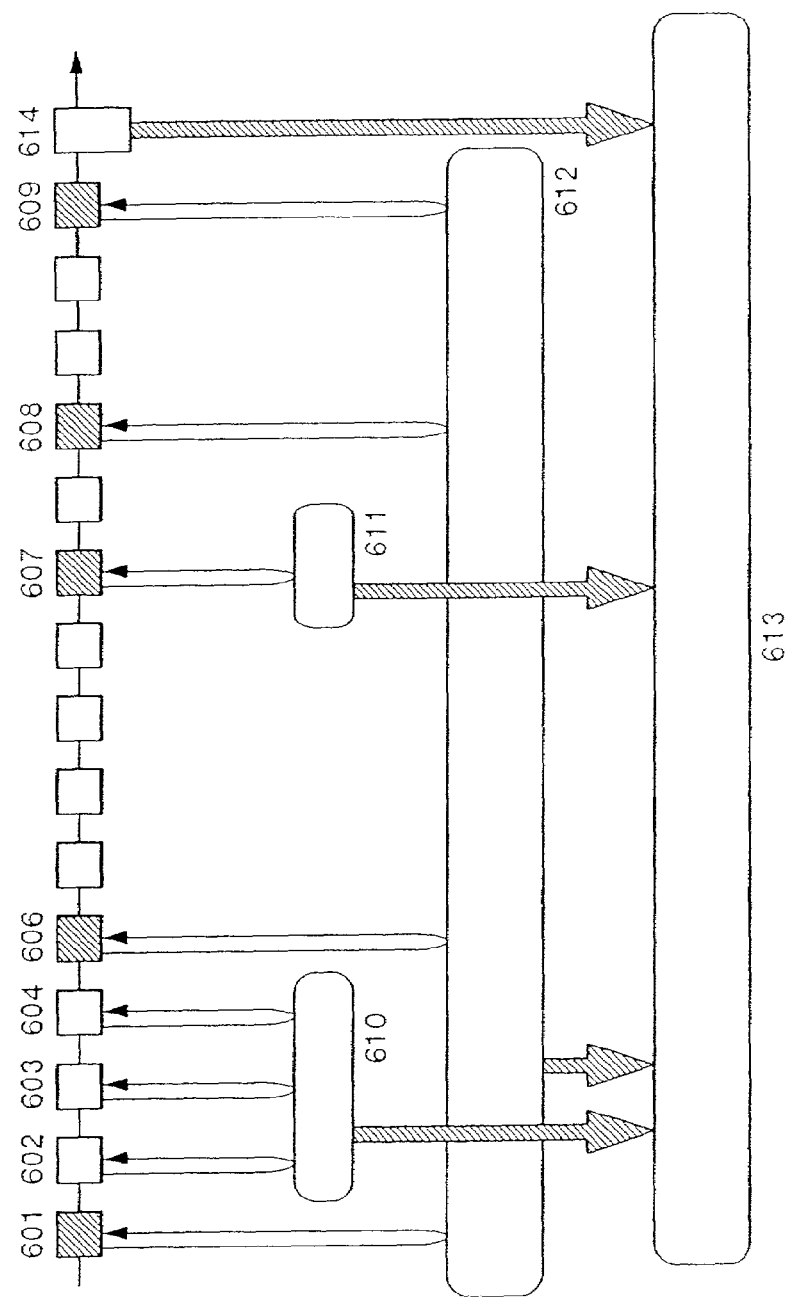
FIG. 32 is a diagram showing the configuration of a semiconductor fabrication line along which apparatuses for detecting defects such as foreign particles are installed.
Figure 33:
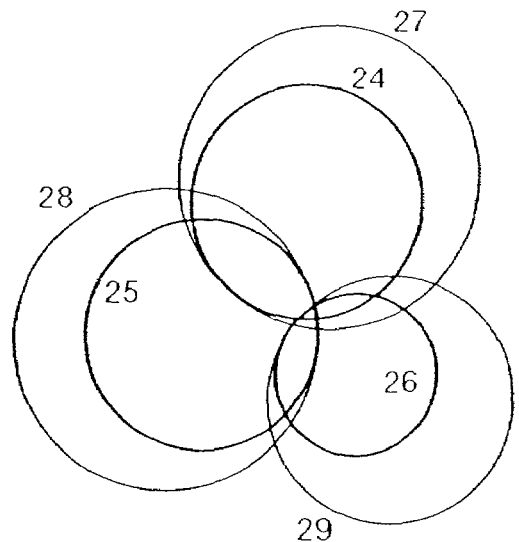
FIG. 33 is an explanatory diagram used for describing the fact that, by increasing the number of various defect inspecting apparatuses which are installed along a semiconductor fabrication line and capable of detecting a variety of foreign particles, it is possible to construct a system displaying a high performance as a whole.
Figure 34:
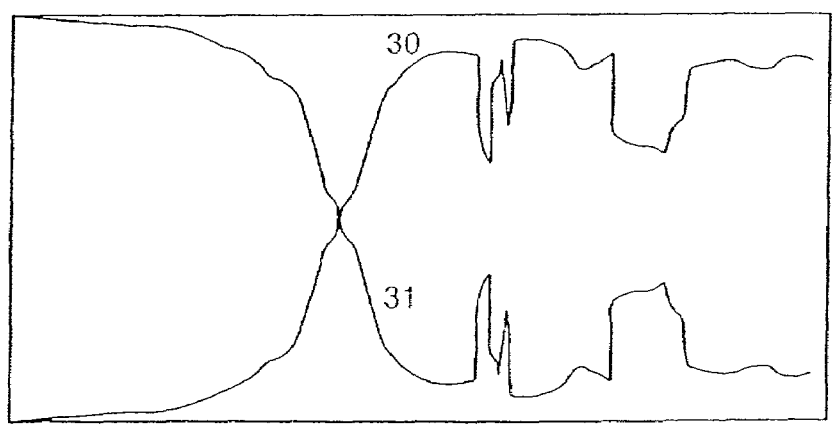
FIG. 34 is a diagram showing changes in yield and defect count that are observed during a build-up period of mass production.

The following description explains lines and methods using the defect inspecting apparatus provided by the present invention as described so far to fabricate semiconductors by referring to FIGS. 32 to 34.

As shown in FIG. 32, a line using the defect inspecting apparatus provided by the present invention to fabricate semiconductors comprises fabrication processes 601 to 609, defect inspecting apparatuses 610 to 613, a probe inspection process 614 and a data analyzing system 613.

Having a big effect on or greatly affecting the yield, the fabrication processes 601, 605, 608 and 609 are monitored all the time by the defect inspecting apparatus 612 such as the one provided by the present invention. If an abnormality is detected between the fabrication processes 601 and 606 by this monitoring, the fabrication processes 602, 603 and 604 are monitored by the defect inspecting apparatus 610 to determine the abnormality or to identify the failing piece of equipment. The particularly important fabrication process 607 is monitored dedicatedly by the defect inspecting apparatus 611.

By the way, in order to allow only a desired process to be inspected for a foreign particle or an outermost surface in the desired process to be inspected for a defect such as a foreign particle attached thereto with a high degree of precision, an inspection for a defect such as a foreign particle is implemented by using the defect inspecting apparatus 612 provided by the present invention before and after the desired process and, then, a result of the pre-process defect inspection is compared with a result of the post-process defect inspection to find a logical difference. In a judgment on the existence of a defect such as a foreign particle based on the logical difference, a foreign particle generated before the process must not be incorrectly interpreted as a defect introduced during the process. A pre-process defect should rather be ignored. This is because a pre-process defect leads to a measure to prevent a defect based on a wrong judgment.

By merely using the logical difference described above, however, it is not always possible to detect only a defect such as a foreign particle generated in the process in question due to the following reasons.

For example, a film is created in a film formation process on a surface having a defect such a foreign particle. Thus, the size of the defect such as a foreign particle increases, raising the inspection sensitivity. As a result, a defect that has been existing since a time prior to the film formation process is detected after the process. That is to say, the defect that has been existing since a time prior to the film formation process was not detected before the process but is found after the process and is incorrectly regarded as a defect generated during the process.

Figure 51:
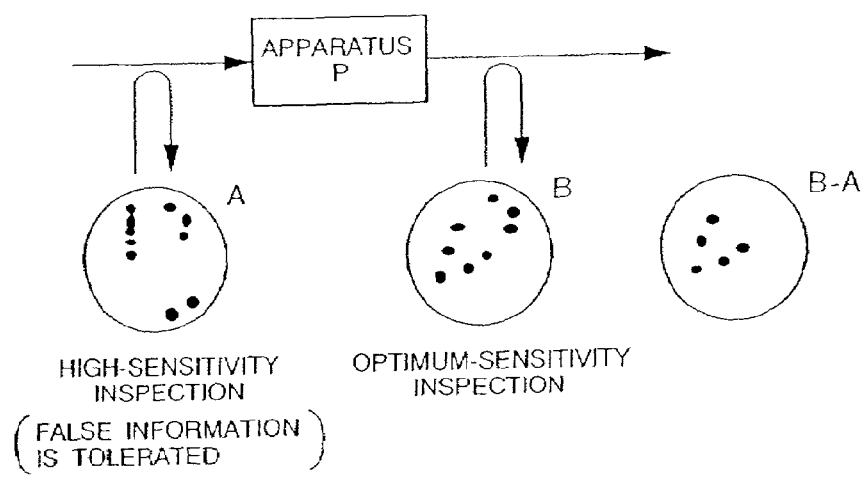
FIG. 51 is a diagram showing an embodiment wherein a substrate is inspected for a defect at a high sensitivity prior to processing by a process performing apparatus P to produce a pre-processing result A, the surface is inspected for a defect after the processing to produce a post-processing result B and a logic difference (B–A) is found.

In order to solve this problem, in an inspection prior to the film formation process, the multiplier m1 is typically reduced to decrease a threshold value and to increase the inspection sensitivity. In this way, a defect that has been existing since a time prior to the film formation process can be detected and an incorrect judgment can be avoided. If the inspection sensitivity prior to the film formation process is increased as described above, however, the number of incorrect detection cases each generating false information also increases. By computing a logical difference (B−A) between results obtained before and after a process as shown in FIG. 51, nevertheless, this problem can be solved.

However, conditions of a surface before and after a process may vary from area to area in a chip of the inspected substrate 1. For this reason, even if threshold values are decreased entirely before the process, the background level increases. As a result, the threshold values increase and there is introduced an area which is in fact in an uninspectable state or a low-sensitivity state. An infinitesimal defect existing in an area in such a state can not be detected.

In order to solve the problem described above, the CPU 417 of the central processing unit 400 of the defect inspecting apparatus 612 judges a defect to have been generated in a process P only if, for $Ib<Tb$, $Ia>Tha$ is detected and $Ia>\kappa \times Thb$. That is to say, a defect is judged to have been generated during a process P only when no defect is detected in an inspection prior to the process P even at a highest possible inspection sensitivity but the defect is detected in an inspection after the process P even if the inspection sensitivity is reduced and the threshold value is increased. If no defect is detected in an inspection after the process P when the inspection sensitivity is reduced and the threshold value is increased by $\kappa$ times, processing to ignore defects is carried out to avoid an incorrect judgment, because the possibility in which a defect is judged to have been generated during the process P is reduced. Of course, if $Ib \geq Thb$, the CPU can judge a defect to have been generated before the process P.

The symbol Ia denotes the level of a detection signal of a defect detected in an inspection after the process P and the symbol Ib denotes the level of a detection signal of a defect detected in an inspection prior to the process P. The symbol Tha denotes the level of a threshold value obtained from the threshold-value-map storage means 419 after the process P and the symbol Thb denotes the level of a threshold value obtained from the threshold-value-map storage means 419 prior to the process P at a lowest possible inspection. The symbol $\kappa$ denotes a coefficient which is greater than 1 and determined in accordance with Thb. It should be noted that the comparison circuit 414 employed in the image-signal processing unit 400 of the defect inspecting apparatus compares Ia with Tha and Ib with Thb.

Thus, the aforementioned processing to form a judgment on the existence of a defect such as a foreign particle carried out by the CPU 417 needs threshold-value levels (a threshold-value image) of all chip areas or conforming areas prior to the process (in some cases, after the process) which have been obtained from the threshold-value-map storage means 419 and stored in the storage unit 427. The CPU 417 also needs defect-detection signals before and after the process which have also been obtained from the memory 404 and stored in the storage unit 427. What is important here is the fact that information of a threshold-value map for inspections before a process is stored in the storage unit 427 in advance and that the coefficient $\kappa$ is determined to be used in determination of a threshold value ($\kappa \times Tha$) for an inspection after the process by using the information of the threshold-value map. As a matter of course, Tha is computed by the threshold-value computing means 418 in an inspection after the process.

The following description explains monitoring techniques adopted by the defect inspecting apparatus 612 to monitor the fabrication processes 602, 603 and 604. According to a first monitoring technique, attention is paid to a particular wafer in a lot and the wafer is monitored for changes in state of attachment of a defect such as a foreign particle to the wafer every time the wafer goes through each or the processes. According to a second monitoring technique, attention is paid to a particular piece of fabrication equipment or a particular fabrication process and, by monitoring the states of a wafer before and after the particular process, the state of the particular piece of fabrication equipment or the particular fabrication process can be monitored. A point common to the two monitoring techniques is that the state of a fabrication process is monitored. However, it is an object of the first monitoring technique to compare fabrication processes with each other, while it is an object of the second fabrication technique to compare changes of a fabrication process with time with each other. That is to say, it is an object of the second fabrication technique to monitor an accident such as a sudden generation of a foreign particle or to evaluate an effect obtained as a result of implementation of some measures to reduce the number of defects such as foreign particles.

The defect inspecting apparatus 612, in particular, control to pay attention to a specific fabrication process or a specific piece of fabrication equipment for the process, allows the user to know how the number of defects generated in the process can be increased or reduced. In addition, from the size of a detected foreign particle, the control particularly determines the fatality of the inspected wafer caused by the foreign particle in the fabrication process, hence, allowing the importance of a measure taken for the foreign particle and a motive for implementation of the measure to be known. The control is thus very effective. That is to say, by knowing the scale of an effect of a measure taken for a defect such as a foreign particle, the user becomes more strongly conscious of awareness of the measure, being led to an action taken to implement the measure.

As described above, data obtained from the monitoring is supplied to the data analyzing system 613 for analyzing, among other things, generation of an abnormality, its correlation with data received from the probe inspection process 614 and its correlation with the yield.

In addition, as the defect inspecting apparatuses 610, 611 and 612 described above, defect inspecting apparatuses adopting optical bright visual-field inspection and SEM inspection techniques can be employed besides the defect inspecting apparatus provided by the present invention. These defect inspecting apparatuses have their own characteristics so that foreign particles that can be detected by these apparatuses are different from each other. Thus, by combining these defect inspecting apparatuses, the total reliability of the defect inspection can be increased. In addition, these defect inspecting apparatuses have different inspection times or inspection throughputs due to differences in detection principle. While the laser scattering technique adopted by a defect inspecting system for a high throughput is suitable for inspection of an inspected object for an infinitesimal particle, the complementation rate during the inspection is low due to laser interference. On the other hand, while the optical bright visual-field inspection technique has a high complementation rate, its throughput is low due to the fact that a high resolution is required in a sampling operation for comparison inspection. In the case of an inspection technique using an electron beam, it is difficult to increase the inspection speed since the SN ratio is low. However, this technique is suitable for high-resolution inspection of an object for a defect such as a bad electrical conduction.

In an LSI fabrication process, systemization of these defect inspecting apparatuses is required along with a need for consideration of the sensitivity, the throughput and detectable objects.

By increasing the number of defects such as foreign particles that can be detected by each of the defect inspecting apparatuses from a domain 24 to a domain 27, from a domain 25 to a domain 28 and from a domain 26 to a domain 29 as shown in FIG. 33, the total number of detection cases of the system can be raised. As a result, it is possible to construct a system having a high performance as a whole.

FIG. 34 is a diagram showing a curve 30 representing changes in yield which are obtained during a build-up time of a mass production. The diagram also shows a curve 31 representing changes in detected-defect count. As shown in the figure, as the yield increases, the number of detected defects decreases. Even in a build-up state of the yield, however, the number of detected defects may increase all of a sudden, decreasing the yield. In such a case, the generation of the defects is recognized quickly and production based on fabrication processes causing the defects needs to be halted temporarily in order to determine a countermeasure for causes of the generation of the defects. That is why the defect inspecting apparatus provided by the present invention is required.

As described above, according to the present invention, the efficiency of illumination can be increased and the intensity of a diffraction light generated by a pattern on a substrate such as an LSI pattern can be reduced by using a spatial filter and adjusting the direction of the illumination. In addition, it is possible to decrease a threshold value at each of positions on a chip with variations different from each other. As a result, there is exhibited an effect of a capability of inspecting a substrate such as an LSI wafer for a foreign particle or a defect existing on the substrate with a high degree of sensitivity at a high throughput.

In addition, according to the present invention, by using an ordinary TDI image sensor with a high sensitivity, there is exhibited an effect of a capability of detecting an infinitesimal foreign particle and a defect existing on an inspected substrate, on which repetitive and non-repetitive patterns coexist with each other, with a high degree of sensitivity at a high speed.

What is claimed is:

1. A defect inspecting apparatus comprising:
a stage used for mounting a substrate serving as an object of inspection and having circuit patterns created thereon, said stage enabling movement of said substrate;
an illumination optical system for radiating an illumination beam to said substrate;
a detection optical system for receiving scattered light reflected from said substrate illuminated by said illumination optical system and for converting said received light into detection image signals by using an image sensor; and
an image-signal processing unit including a variation computation unit which computes a variation of said detection image signals at corresponding locations including corresponding adjacent locations between areas where circuit patterns with substantially identical shapes are naturally repeated on said inspected substrate, a criterion setting unit which sets a criterion on the basis of said variation computed by said variation computation unit, and a signal extracting unit which extracts a signal indicating a defect such as a foreign particle whether said detection image signal is exceeded by said criterion set by said criterion setting unit.

2. A defect inspecting apparatus according to claim 1, wherein said illumination optical system is constructed so as to irradiate a slit-shaped beam as said illumination beam from a light source to said substrate in a direction inclined at a predetermined gradient related to a direction of a line normal to said inspected with a longitudinal direction thereof being oriented substantially perpendicularly to a movement of said stage.

3. A defect inspecting apparatus according to claim 1, wherein said signal extracting unit has a unit for which said criterion is set for each of a variety of areas constituting said circuit pattern.

4. A defect inspecting apparatus according to claim 1, wherein in said illumination optical system, said light source is a laser light source.

5. A defect inspecting apparatus according to claim 1, wherein a spatial filter is provided in said detection optical system.

6. A defect inspecting apparatus according to claim 1, wherein said criterion setting unit sets said criterion on the basis of a value which is multiplied by a magnification m1 according to a false-information generation rate to said variation.

7. A defect inspecting apparatus according to claim 1, wherein in said image-signal processing unit, said variation computation unit computes said variation of said detection signals at corresponding locations including corresponding adjacent locations between areas as a variation of differential detection signals at corresponding locations between adjacent areas, said detection signals being differential detection signals at said corresponding locations between said adjacent areas.

8. A defect inspecting apparatus according to claim 1, wherein said image-signal processing unit has an output unit which outputs pieces of data representing a result inspection extracted by said signal extracting unit and said criterion set by said criterion setting unit.

9. A defect inspecting apparatus according to claim 1, wherein said image-signal processing unit has a display unit which displays map information on said area as said criterion or an image of said criterion used in said signal extracting unit.

10. A defect inspecting apparatus according to claim 1, wherein said illumination optical system has a control unit which controls power of the illumination beam in accordance with an area priority mode, a standard mode and a sensitivity priority mode.

11. A defect inspecting apparatus according to claim 1, wherein said image-signal processing unit has a display unit which displays a relation between said criterion and an index about sensitivity corresponding to said criterion.

12. A defect inspecting apparatus according to claim 1, wherein said image-signal processing unit has a display unit which displays sensitivity information for said area corresponding to said criterion.

13. A defect inspecting apparatus according to claim 1, wherein said illumination beam radiated by said illumination optical system is a Deep Ultra-Violet beam.

14. A defect inspecting apparatus comprising:
an illumination optical system for radiating an illumination beam to a substrate serving as an object of inspection;
a detection optical system including a beam splitting optical system for splitting a light beam reflected by said substrate into reflected beams with one of said reflected beams having an intensity which is different from an intensity of another of said reflected beams, and a plurality of image sensors for receiving said reflected beams output by said beam splitting optical system; and
an image-signal processing unit for processing said detection signals output by each of image sensors so as to extract a signal indicating a defect.

15. A defect inspecting apparatus according to claim 14, wherein in said beam splitting optical system, a ratio of intensity difference of said reflected beams is about 1/100.

16. A defect inspecting apparatus according to claim 14, wherein an optical axis in said detection optical system is inclined with respect to a line normal to said substrate.

17. A defect inspecting apparatus comprising:
an illumination optical system for radiating an illumination beam to a substrate serving as an object of inspection;
a detection optical system having an optical axis inclined with respect to a line normal to said substrate so as to receive light obtained through a spatial filter from scattered light reflected from said substrate illuminated by said illumination optical system, said spatial filter enabling shielding of a Fourier-transmission image formed by a diffraction light generated from at least repetitive patterns in circuit pattern existing on said substrate, and an image sensor for converting received light into detection image signals; and
an image-signal processing unit for processing said detection image signals to extract a signal indicating a defect such as a foreign particle, by using criteria set on the basis of variation of said detection image signals.

18. A defect inspecting apparatus comprising:
a stage used for mounting a substrate serving as an object of inspection and having circuit patterns created thereon, said stage enabling movement of said substrate;
an illumination optical system for radiating an illumination beam to said substrate;
a detection optical system for receiving scattered light reflected from said substrate illuminated by said illumination optical system and for converting said received light into detection image signals by using an image sensor; and
an image-signal processing unit including an image memory which memorizes said detection image signals in a pixel unit converted by said image sensor;
a plurality of operators having different dimensions changed by size of pixel unit to each other in order to judge defects for which sizes differ, the detection image signals obtained from said image memory by each of different dimensions in each if said operators being extracted and being outputted as gradation image signals of predetermined level from a central pixel by convolution of said extracted image signals; and
a comparison circuit which compares gradation image signals outputted from each of said operators with predetermined threshold values in order to judge said defects such as foreign particles for which sizes differ.

* * * * *